(12) United States Patent
Liu et al.

(10) Patent No.: US 8,394,604 B2
(45) Date of Patent: Mar. 12, 2013

(54) PROTEIN SPLICING USING SHORT TERMINAL SPLIT INTEINS

(75) Inventors: Paul Xiang-Qin Liu, Halifax (CA); Kaisong Zhou, Halifax (CA); Gerrit Volkmann, Halifax (CA)

(73) Assignee: Paul Xiang-Qin Liu, Halifax, Nova Scotia (CA)

( * ) Notice: Subject to any disclaimer, the term of this patent is extended or adjusted under 35 U.S.C. 154(b) by 31 days.

(21) Appl. No.: 12/990,402

(22) PCT Filed: Apr. 30, 2009

(86) PCT No.: PCT/CA2009/000582
§ 371 (c)(1), (2), (4) Date: Oct. 29, 2010

(87) PCT Pub. No.: WO2009/132455
PCT Pub. Date: Nov. 5, 2009

(65) Prior Publication Data
US 2011/0172391 A1    Jul. 14, 2011

Related U.S. Application Data

(60) Provisional application No. 61/049,328, filed on Apr. 30, 2008.

(51) Int. Cl.
*C12P 21/06* (2006.01)
(52) U.S. Cl. ................................. 435/68.1
(58) Field of Classification Search ........... None
See application file for complete search history.

(56) References Cited

PUBLICATIONS

Amitai, G et al., The Journal of Biological Chemistry. Jan. 30, 2004, vol. 279, No. 5, pp. 3121-3131.
Ando, T., et al., (2007) Chem Commun (Camb), 4995-4997.
Appleby, J.H., et al., (2009) J Biol Chem, 284, 6194-6199.
Caspi, J., et al. (2003) Mol Microbiol 50, 1569-1577.
Chong, S., et al., (1997) Gene 192, 271-281.
Ciechanover, A., et al., (1983) J Biol Chem, 258, 9681.
Cui, C., et al., (2006) Protein Expr Purif 50, 74-81.
Dalgaard, J. Z., et al. (1997) J Comput Biol 4, 193-214.
Dautry-Varsat, A., et al., (1983) Proc Natl Acad Sci U.S.A. 80, 2258.
David, R. et al., Eur. J. Biochem. 271, (2004) p. 663-677.
Derbyshire, V., et al. (1997) Proc Natl Acad Sci U S A 94, 11466-11471.
Ding, Y., et al. (2003) J Biol Chem 278, 39133-39142.
Duan, X., et al. (1997) Cell 89, 555-564.
Evans, T.C., Jr., et al. (2000) J Biol Chem 275, 9091-9094.
Evans, T.C., Jr., et al., (1998) Protein Sci 7, 2256-2264.
Evans, T.C., Jr., et al., (1999) J Biol Chem 274, 18359-18363.
Foley, T.L., et al. (2007) Curr Opin Chem Biol. 11, 12-9.
Guignet, E. G., et al., (2004) Nat Biotechnol 22, 440-444.
Ichiyanagi, K., et al. (2000) J Mol Biol 300, 889-901.
Klabunde, T., et al. (1998) Nat Struct Biol 5, 31-36.
Kwon, Y. et al., (2006) Angew Chem Int Ed 45, 1726-1729.
Lew, B.M., et al., (1999) Biopolymers 51, 355-362.
Liu, X. Q. (2000) Annu Rev Genet 34, 61-76.
Liu, X. Q., et al. (2003) J Biol Chem 278, 26315-26318.
Ludwig, C., et al. (2006) Angew Chem Int Ed 45, 5218-5221.
Martin, D. D., et al. (2001) Biochemistry 40, 1393-1402.
Mathys, S., et al., (1999) Gene 231, 1-13.
McCann, C.M., et al., (2005) Biotechniques 38, 945-952.
Miller, L.W., et al., (2005) Curr Opin Chem Biol. 9, 56-61.
Mills, K. V., et al. (1998) Proc Natl Acad Sci U S A 95, 3543-3548.
Muir, T.W., (2003) Annu Rev Biochem, 72, 249-289.
Muir, T.W., (2008) Biopolymers. 90, 743-750.
Muralidharan, V., et al. (2006) Nat Methods 3, 429-38.
O'Hare, H.M., et al., (2007) Curr Opin Struct Biol. 17, 488-494.
Paulus, H. (2000) Annu Rev Biochem 69, 447-496.
Pellois, J.P., et al., (2006) Curr Opin Chem Biol. 10, 487-91.
Perler, F. B. (2002) Nucleic Acids Res 30, 383-384.
Perler, F. B., et al., (1994) Nucleic Acids Res 22, 1125-1127.
Pietrokovski, S. (1998) Protein Sci 7, 64-71.
Saleh, L., et al. (2006) Chem Rec 6, 183-193.
Scott, C.P., et al., (1999) Proc Natl Acad Sci U.S.A. 96, 13638-13643.
Southworth, M. W., et al. (1998) Embo J 17, 918-926.
Sun, W., et al. (2004) J Biol Chem 279, 35281-35286.
Telenti, A., et al. (1997) J Bacteriol 179, 6378-6382.
Walsh, C.T., et al., (2005) Angew Chem Int Ed Engl. 44, 7342-7372.
Wu, H., et al. (1998) Proc Natl Acad Sci U S A 95, 9226-9231.
Wu, H., Xu, M. Q., et al. (1998) Biochim Biophys Acta 1387, 422-432.
Xie, J., et al., (2005) Curr Opin Chem Biol. 9, 548-554.
Xu, M. Q., et al. (1996) Embo J 15, 5146-5153.
Xu, M.Q., et al., (2001) Methods 24, 257-277.
Yang, J., et al. (2004) Mol Microbiol 51, 1185-1192.

*Primary Examiner* — Suzanne M Noakes

(57) ABSTRACT

The invention provides methods of producing functional split inteins having small N-intein and/or small C-intein. Using these split inteins with their protein trans-splicing and cleavage activities, we provide new and more effective methods of manipulating proteins. They include site-specific addition of synthetic peptides at protein's terminal and internal locations, ligation of synthetic and/or expressed polypeptides, controllable cyclization of synthetic and/or expressed polypeptides, and controllable cleavages of recombinant proteins. These methods have numerous utilities including but not limited to protein fluorescence labeling, fixation on microchips, site-specific PEGylation, and linkage with pharmaceutical molecules.

26 Claims, 19 Drawing Sheets

Contiguous intein: 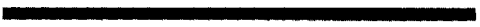

Conventional split intein: 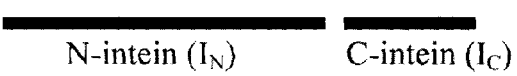
N-intein ($I_N$)  C-intein ($I_C$)

Small C-intein (SCI) split intein: 
$I_N$                              $I_C$ Small N-intein (SNI) split intein: 
$I_N$   $I_C$ 3-piece split intein: 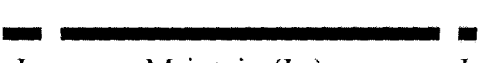
$I_N$   M-intein ($I_M$)   $I_C$

```
Ssp  GyrB    CFSGDTLVALTD//----------------------------GRSVSFEQLVEEEKQGK-QNFCYT
Ssp  DnaX    CLTGDSQV-LTR//----------------------------NGLMSIDNPQIKGRE----VLSYN
Ter  DnaE3   CLTYE//TEIMTV-----------------------------EYGPLPIGKIVEYRIE--CTVYTVD
Ter  ThyX    CLSGNTKVRFRY//SSSSQEAKYYEETIEKLANLWHYGSKNQYTSKDAKCMQENISSRNIFTLD
Rma  DnaB    CLAGDTLITLA//-----------------------------DGRVPIRELVSQQNF--SVWALNP
Ssp  DnaB    CISGDSLISLA//-----------------------------STGKRVSIKDLLDEKD---FEIWAIN
             β1   β2                                   β3              β4

Ssp  GyrB    IRHDGSIGVEKIINARKTKTNAKVIKVTLDNGESIICTPDHKFMLRDGSYKCAMDLTLDDSLMP
Ssp  DnaX    ETLQQWEYKKVLRWLDRGE-KQTLSIKTKN-S-TVRCTANHLIRTEQGWTRAENITPGMKILSP
Ter  DnaE3   KNG-YIYTQPIAQWHNRGM-QEVYEYSLEDGT-VIRATPEHKFMTEDGQMLPIDEIFERNLDLK
Ter  ThyX    TQTNQIVSSKITNIYINGE-KETYTIKTVSGK-EIRATLEHQFWTNQGWKRLKDFSTQLCEVQL
Rma  DnaB    QTYRLERAR--VSRAFCTGIKP VYRLTTRLGRSIRATANHRFLTPQGWKRVDELQPGDYLALP
Ssp  DnaB    EQTMKLESAKVSRVFCTGK-KLVYILKTRLGR-TIKATANHRFLTIDGWKRLDELSLKEHIALP

Ssp  GyrB    LHRKISTTEDSGH-*MEAVLNYNHRIVNIEAVSETIDVYDIEVPHTHNFALAS//GVFVHNS
Ssp  DnaX    AS-----------*PSPQWHTNFEEVESVTKGQVEKVYDLEVED-NHNFVAN//GLLVHNC
Ter  DnaE3   CLGTLELE-----------*FVKIVSRKLAKTENVYDIGVTKDHNFVLAN//GLIASNC
Ter  ThyX    AANK----------*DNSGVFVEIESIEKFGKEITYDLEVEHPEHNFIAN//GLVVHNS
Rma  DnaB    RRIP-----------*AQSDVYWDPIVSIEPDGVEEVFDLTVPGP-HNFVAN--DIIAHNS
Ssp  DnaB    RKLESSSLQ*SPEIEKLSQSDIYWDSIVSITETGVEEVFDLTVPGP-HNFVAN--DIIVHNS
                                          β10           β11       β12
```

FIG. 1

C-terminal Peptide Splicing:
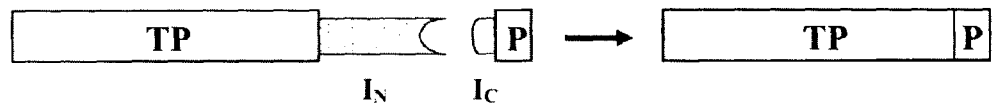
N-terminal Peptide Splicing:
Internal Peptide Splicing:
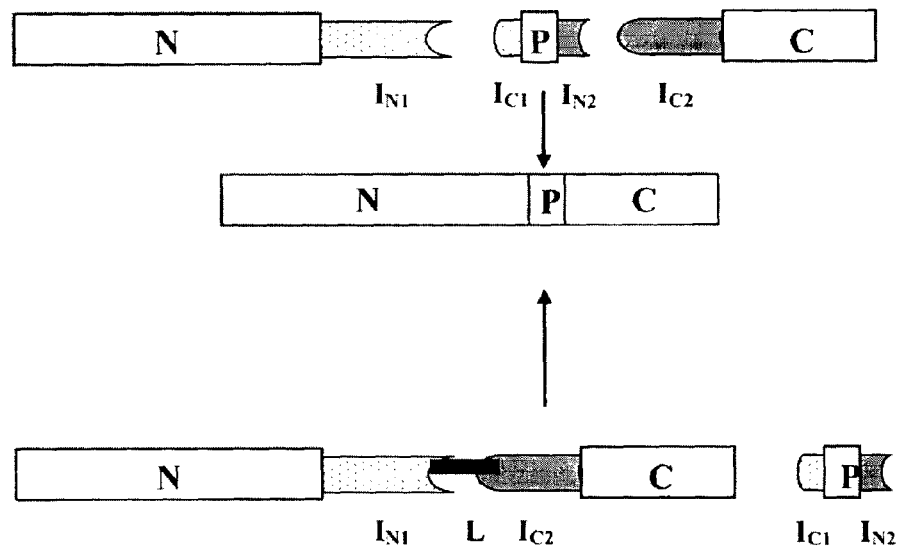
FIG. 2

Two-peptide splicing:
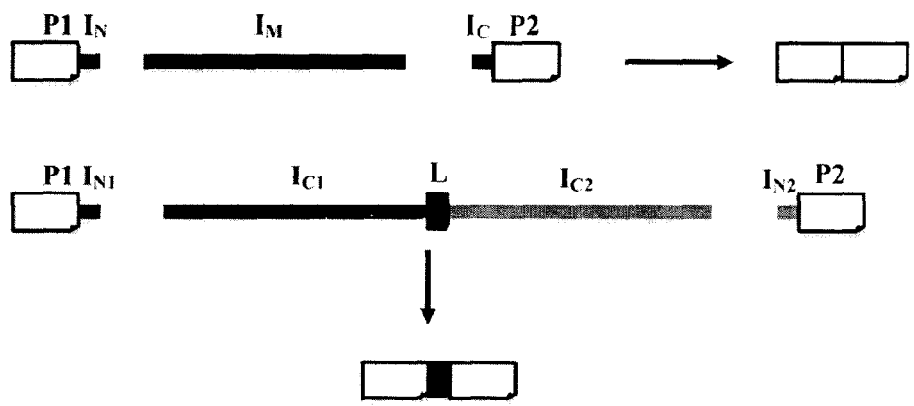
Peptide and protein cyclization:
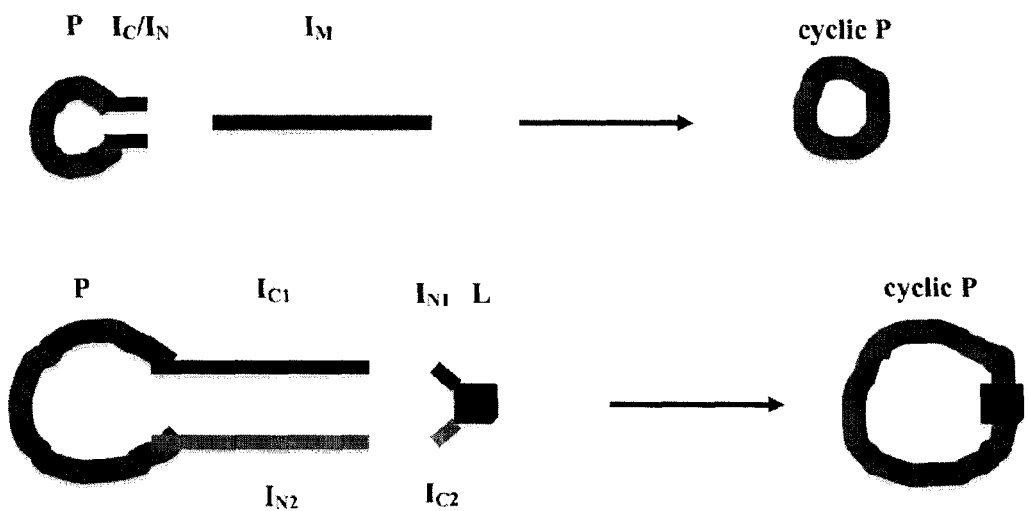
FIG. 3

A.
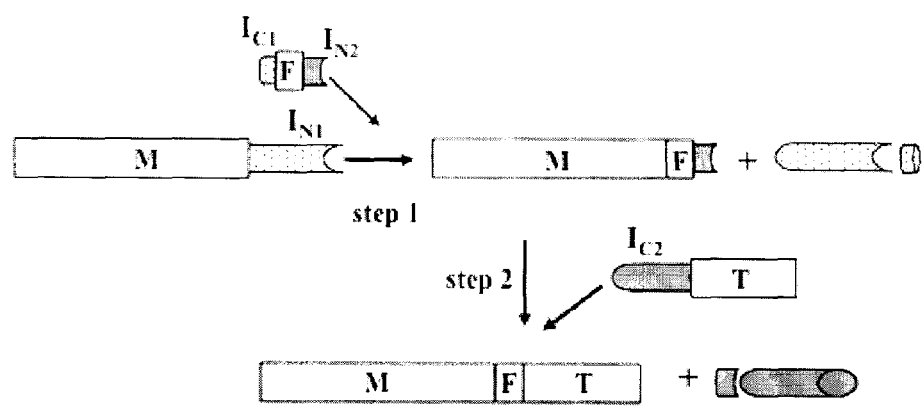
B.
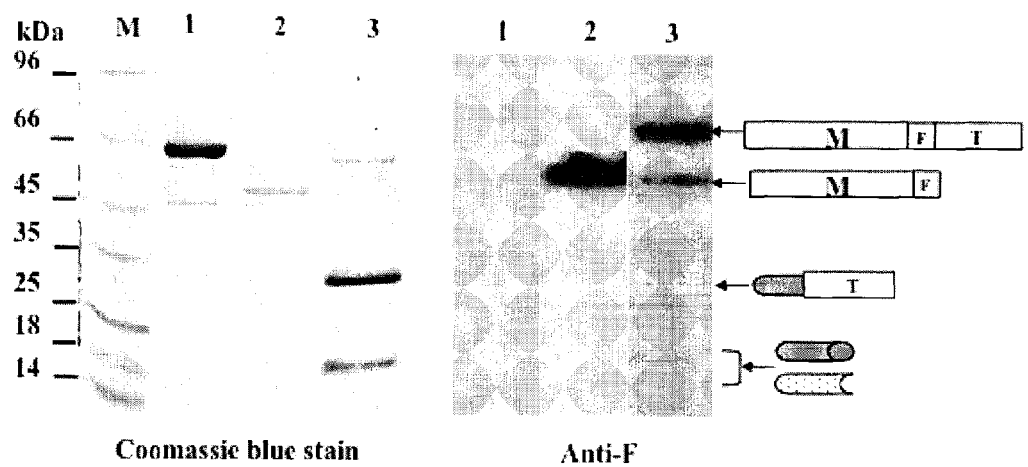
FIG. 6

A.
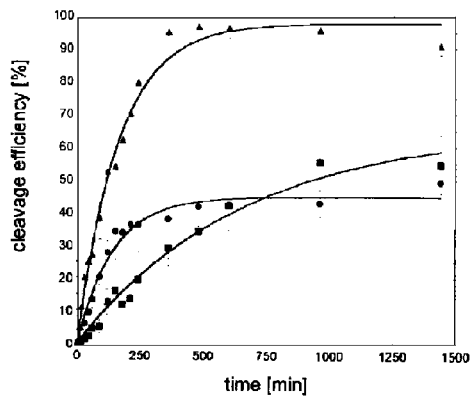
B.
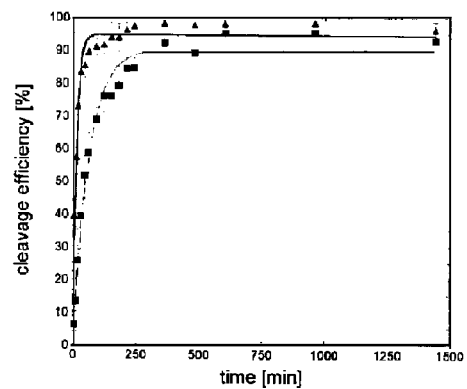
C.
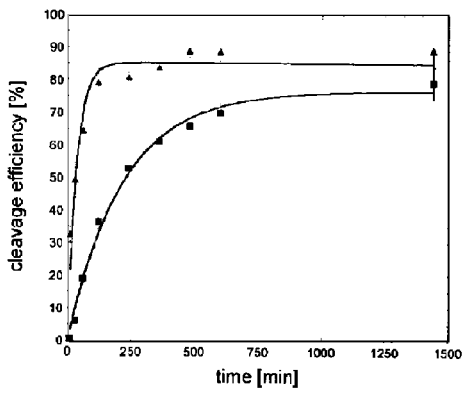
D.
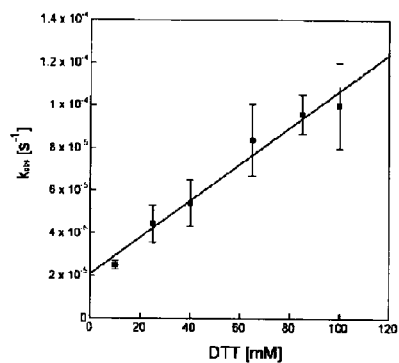
FIG. 14

PROTEIN SPLICING USING SHORT TERMINAL SPLIT INTEINS

REFERENCE TO RELATED APPLICATIONS

This application claims the benefit of U.S. Provisional Application No. 61/049,328 filed Apr. 30, 2008, the content of which is herein incorporated by reference.

FIELD OF INVENTION

The invention relates to the use of inteins for protein splicing; specifically, to methods and tools relating to split inteins for manipulating polypeptides.

BACKGROUND OF THE INVENTION

Inteins are internal protein sequences that catalyze a protein-splicing reaction, which precisely excise the intein sequence and join the flanking sequences with a peptide bond. Inteins are embedded within a variety of host proteins termed exteins. Over 350 inteins have been identified in various proteins from bacteria, archaea, and eukaryotes. In a 2006 review (Saleh et al 2006 The Chemical Record 6:183-193), the authors state at page 189: "Most naturally or artificially split inteins are fragmented between motifs B and F (the position where the EN domain is found) yielding C-terminal intein fragments (IC) that are ~25-40 aa, well within the scope of solid phase protein synthesis (SPPS), and N-terminal intein fragments (IN)>100 aa. Not all fragmentation positions in this region yield functional pairs. The Ssp DnaB mini-intein can also be reassembled from three pieces, including an In of only 11 aa. Fragmentation positions within the two long Ssp DnaB intein β-strands (β5 and β10) that form the backbone of the horseshoe structure yielded inactive intein fragments." [internal citations omitted]

Inteins split into an N-terminal portion (N-inteins) and a C-terminal portion (C-inteins), which can reassociate non-covalently to form a functional intein, occur in nature and have also been engineered from contiguous inteins. Sun et al 2004 J Biol Chem 279(34):35281-35286 [42] reported an unsuccessful attempt to produce a small (6-amino acid) C-terminal intein from Ssp DnaB.

SUMMARY OF THE INVENTION

We describe here an invention based in part on, but is not limited to, our discovery that small terminal inteins are functional in splicing reactions. Specifically, this is the first time that small C-terminal inteins are shown to have splicing function. Accordingly, the invention relates to methods of making and using functional split inteins having C-intein (Ic) and/or N-intein (In), either or both of which maybe small (sometimes referred to herein as SCI and SNI). The invention further relates to protein manipulations using split inteins.

The invention provides, in various aspects, small C-terminal split inteins, small split N-inteins, and 3-piece split inteins. The SCI sequences correspond to contiguous sequences near the C-terminus of natural inteins and may be constructed by splitting contiguous intein sequences at a site near the C-terminus. Similarly, The SNI sequences correspond to contiguous sequences near the N-terminus of natural inteins and may be constructed by splitting contiguous intein sequences at a site near the N-terminus. 3-piece split inteins comprise small C-terminal split inteins, small N-terminal split inteins, and a remainder or middle intein (sometimes referred to herein as M-intein or IM).

Described herein are methods of protein manipulations using split inteins. Such methods include C-terminal peptide splicing, N-terminal peptide splicing, and internal peptide splicing. These methods are useful for addition of a variety of desired chemical moieties to proteins of interest site-specifically at either terminal or internal locations through an enzymatic (trans-splicing) reaction. For example, C-terminal peptide splicing using an SCI can add a desired peptide to the C-terminus of a target protein. Similarly, N-terminal peptide splicing using an SNI can add a desired peptide to the N-terminus of a target protein. Both C-terminal and N-terminal peptide splicing reactions may be carried out on affinity beads or column to automatically release the protein product in a purified form. C-terminal and N-terminal peptide splicing may also be carried out with the target protein immobilized on other surfaces, for example, cell membranes or phage surfaces, or in solution or within cells. Internal peptide splicing using both SCI and SNI may insert a desired peptide into an internal location of a target protein.

One application of the invention is to site-specifically add to a target protein any desired and available chemical moieties, which include among others, fluorescence groups, biotin, polyethylene glycol (PEG), amino acid analogs, unnatural amino acids, phosphate groups, glycosyl groups, radioisotope labels, pharmaceutical molecules, and chemically reactive groups (e.g. ketone, aldehyde, Cys, and Lys) to which other chemical moieties can be linked site-specifically. The above methods are aimed at any target protein of interest, non-limiting examples of which include enzymes, antibodies, antibody fragments, and pharmaceutical proteins. The above methods may be used in any combination among themselves and with other methods to introduce multiple and/or different modifications to a target protein.

One application of the invention is fluorescence labeling of proteins that can be useful for monitoring protein structure, folding, and cellular trafficking. Another object of the invention is biotin labeling of proteins that can be useful for protein fixation on surfaces including, but not limited to, streptavidin-coated microchips.

The invention further provides methods of protein manipulation including two-peptide splicing and controllable protein or peptide cyclization. One method uses a 3-piece split intein. Another method uses a combination of SNI and SCI to join two synthetic or expressed polypeptides with a third or linker sequence.

In the above methods, the synthetic peptides may contain any desired and available chemical moieties to be added to the target protein, which include among others, fluorescence groups, biotin, polyethylene glycol (PEG), amino acid analogs, unnatural amino acids, phosphate groups, glycosyl groups, radioisotope labels, pharmaceutical molecules, and chemically reactive groups (e.g. ketone, aldehyde, Cys, and Lys) to which other chemical moieties can be linked site-specifically.

The invention also provides methods of controllable peptide or protein cyclization, which joins the two ends of a peptide or protein with a peptide bond or a linker in a controllable way. One method uses a 3-piece split intein, while another method uses a SNI split intein and a SCI split intein together and introduces a third or linker sequence. One application of cyclization is to produce a mutant library of cyclized polypeptides that can be subjected to functional or genetic screening or selection for desired functional entities such as protein aptamers.

The invention also provides methods of controllable and site-specific cleavages of recombinant proteins. One method uses SCI to achieve N-cleavage at the N-terminus of In of a precursor protein (e.g. TP-IN-B consisting of a target protein TP, the N-intein In, and an affinity binder B; see for example FIG. 12). The N-cleavage may be triggered by the addition of the small Ic peptide and/or a thiol, such as DTT. Another method uses SNI to achieve C-cleavage at the C-terminus of Ic of a precursor protein (e.g. B-IC-TP in FIG. 12), using the small In peptide as a trigger. Still another method uses SNI to achieve N-cleavage at the N-terminus of In of a precursor protein (e.g. TP-IN-B in FIG. 12), using the larger Ic protein as a trigger. The target protein may be any polypeptide of interest. Non-limiting examples of target proteins include enzymes, antibodies, antibody fragments, and pharmaceutical proteins. The cleavage methods may be useful to cleave an affinity binder from a protein. The affinity binder may be, but is not limited to, a His-tag (6 histidines), a chitin binding domain, a maltose binding protein, and a glutathione-S-transferase. The cleavage reactions may be carried out with the precursor protein being in solution, bound to affinity beads or column, anchored to cell membrane or phage surface, and inside or outside cells. One application of the invention is to have the precursor protein in a cell lysate bound to affinity beads or column, so that the cleavage reaction simultaneously releases the target protein from the beads or column in a purified form. Another application of the invention is to carry out the N-cleavage and the C-cleavage together on a single target protein to permit tandem purifications of the precursor protein using two different affinity binders sequentially and to generate a precise terminus on both ends of the target protein. Another application of the invention is to carry out the cleavage methods in the presence of the thiol compound MESNA to generate a thioester on the C-terminus of the released target protein suitable for expressed protein ligation.

Accordingly, one aspect of our invention relates to a method for covalently linking the N-terminus of a peptide to the C-terminus of a peptide. The method comprises the step of providing a C-terminus of a peptide, the C-terminus being covalently linked via a peptide bond to an N-terminal split intein (In); providing an N-terminus of a peptide, the N-terminus being covalently linked via a peptide bond to a C-terminal split intein (Ic); and contacting the In-linked C-terminus with the Ic-linked N-terminus in the presence of an intein-splicing polypeptide (ISP) under conditions allowing splicing of the In and the Ic and linking of the C-terminus to the N-terminus. The Ic is from 4 to 7 contiguous amino acids, at least 4 of which are from the last beta-strand of the C-terminal region of an intein. The Ic is derived (split) from the intein at a site between the penultimate beta-strand and the last beta-strand of the C-terminal region of an intein. The In, the Ic and the ISP are of the same or cross-reacting intein (I). The intein-splicing polypeptide (ISP) refers to a part of the natural intein from which Ic and In are derived which, when together with Ic and In, results in splicing activity. ISP may be a part of In or may be the remainder or middle intein (IM). Embodiments of the various splicing schemes are illustrated in FIGS. 2 and 3. As used herein, "contacting" means bringing the components of the method together in any environment in which peptide splicing may occur, which includes intracellularly, extracellularly, on affinity beads, on the surface of cells, on the surface of phages, or in solution. Moreover, one or more components of the methods may be immobilized while the other components are in solution.

Not all small C-terminal fragments of inteins are functional for splicing. However, once the inventors have discovered that certain SCIs do have activity, further intein fragments may be assayed for activity. Accordingly it is contemplated that the SCIs of the invention show a splicing efficiency of at least 50% when tested in a trans-splicing activity assay. The assay comprises the steps of: linking the Ic to the N-terminus of a first reporter polypeptide via a peptide bond; exposing the Ic-linked first reporter polypeptide to an N-precursor polypeptide, the N-precursor polypeptide comprising a second reporter polypeptide linked via a peptide bond at its C-terminus to a corresponding N-terminal split intein, under conditions that permit splicing of the Ic-linked first reporter polypeptide and the N-precursor polypeptide, resulting in a fusion of the second reporter polypeptide to the first reporter polypeptide; and detecting the presence of the fusion of the second reporter polypeptide to the first reporter polypeptide.

In certain embodiments, the SCI is from an intein selected from the group consisting of Ssp GyrB, Ssp DnaX, Ter DnaE3, and Ter ThyX. In other embodiments, the Ic is 6 contiguous amino acids. Specifically, the Ic may have the sequence GVFVHN (SEQ ID NO:63), GLLVHN (SEQ ID NO:64), GLIASN (SEQ ID NO:65), or GLVVHN (SEQ ID NO:66).

As illustrations of the method described above, when the N-terminus and the C-terminus belong to separate peptides, the splicing reaction results in a fusion peptide (see e.g. FIGS. 2A and 3A). When the N-terminus and the C-terminus belong to the same peptide, the splicing reaction results in a cyclic peptide. As described previously, the In may comprises the ISP so that when In and Ic are together in a reaction, splicing occurs (see e.g. FIG. 2A). ISP may also be provided as a separate entity, e.g. the middle intein IM, when both In and Ic are small, so that when Ic, In and IM are together in a reaction, splicing occurs (see e.g. FIGS. 3A and 3C).

In various embodiments of the invention, the In is from 3 to 20 contiguous amino acids of the N-terminal region of the intein (I); and is split from the intein (I) at a site next to the first or the second beta-strand.

The invention also relates to methods whereby a peptide is inserted in a target peptide by assembling the pieces using inteins. This is sometimes referred to herein as internal peptide splicing. For illustrative examples, see FIGS. 2C and 3B. The method is based on the basic splicing method described above, comprising the step of providing a first peptide covalently linked at its C-terminus via a peptide bond to an N-terminal split intein (In); providing a second peptide covalently linked at its N-terminus via a peptide bond to a C-terminal split intein (Ic); and contacting the In-linked peptide with the Ic-linked peptide in the presence of an intein-splicing polypeptide (ISP) under conditions allowing splicing of the In and the Ic and linking of the C-terminus to the N-terminus. The Ic is from 4 to 7 contiguous amino acids, at least 4 of which are from the last beta-strand of the C-terminal region of an intein. The Ic is derived (split) from the intein at a site between the penultimate beta-strand and the last beta-strand of the C-terminal region of an intein. The In, the Ic and the ISP are of the same or cross-reacting intein (I). However, for internal peptide splicing, the second peptide is also covalently linked at its C-terminus via a peptide bond to another N-terminal split intein (In2). The method further comprises the step of providing a third peptide covalently linked at its N-terminus via a peptide bond to a second C-terminal split intein (Ic2); and contacting the Ic-linked and In2-linked second peptide with the Ic2-linked third peptide in the presence of a second intein-splicing domain (ISP2) under conditions allowing splicing of the In2 and the Ic2 and linking of the second peptide to the third peptide to produce a fusion of the first peptide, the second peptide and the third peptide. The In2, the Ic2 and the ISP2 are of the same or cross-reacting intein (I2). The split inteins of I1 and I2 should not cross-react, so I2 should be different from I1. In one embodiment of the internal peptide splicing method, the In-linked first peptide is covalently linked to the Ic2-linked third peptide via a peptide linker, before being placed in contact with the Ic-linked and In2-linked second peptide. For an illustrative example, see FIG. 2D. In some embodiments, the In2 is from 3 to 20 contiguous amino acids of the N-terminal region of the intein (I2); and is split from the intein (I2) at a site next to the first or the second beta-strand. For an illustrative example, see FIG. 2C.

Internal peptide splicing is also applicable as a method for splicing two peptides to form a cyclic peptide. The method is based on the basic splicing method described above, comprising the step of providing a first peptide covalently linked at its C-terminus via a peptide bond to an N-terminal split intein (In); providing a second peptide covalently linked at its N-terminus via a peptide bond to a C-terminal split intein (Ic); and contacting the In-linked peptide with the Ic-linked peptide in the presence of an intein-splicing polypeptide (ISP) under conditions allowing splicing of the In and the Ic and linking of the C-terminus to the N-terminus. The Ic is from 4 to 7 contiguous amino acids, at least 4 of which are from the last beta-strand of the C-terminal region of an intein. The Ic is derived (split) from the intein at a site between the penultimate beta-strand and the last beta-strand of the C-terminal region of an intein. The In, the Ic and the ISP are of the same or cross-reacting intein (I). However, for splicing the two peptides to form a cyclic fusion peptide, the first peptide is also covalently linked at its N-terminus via a peptide bond to another C-terminal split intein (Ic2), and the second peptide is also covalently linked at its C-terminus via a peptide bond to another N-terminal split intein (In2). The method further comprises the step of contacting the Ic2-linked and In-linked first peptide with the In2-linked and Ic-linked second peptide in the presence of another intein-splicing domain (ISP2) under conditions allowing splicing of the In2 and the Ic2 to produce a cyclic fusion of the first peptide and the second peptide. The In2, the Ic2 and the ISP2 are of the same or cross-reacting intein (I2). The split inteins of I1 and I2 should not cross-react, so I2 should be different from I1. For an illustrative example, see FIG. 3D. In some embodiments, the In2 is from 3 to 20 contiguous amino acids of the N-terminal region of the intein (I2); and is split from the intein (I2) at a site next to the first or the second beta-strand.

The precursor polypeptides comprising the target polypeptide and the Ic and In may be synthesized recombinantly, e.g. the peptide having the Ic-linked N-terminus, or the peptide having the In-linked C-terminus, or the Ic-linked and In2-linked second peptide, or the Ic2-linked third peptide may be expressed from a nucleic acid encoding them in a cell or in a cell-free translation system as is well-known in the art. The splicing reaction may occur in vivo, with the various precursor peptides being expressed in a cell, or in vitro with the precursor peptides in cell lysates or in purified form, in solution or immobilized. In certain embodiments, the precursor polypeptides comprising the target polypeptide and the SCI and SNI are sufficiently small that they may be chemically synthesized as a practical and economical option. It is contemplated that the peptide having the Ic-linked N-terminus, or the peptide having the In-linked C-terminus, or the Ic-linked and In2-linked second peptide, or the Ic2-linked third peptide, is 5-100 amino acids, preferably 5-50 amino acids, 10-40 amino acids, 10-30 amino acids, or 10-20 amino acids.

Another aspect of our invention relates to a method for site-specifically cleaving a peptide. The method comprises contacting a precursor peptide with a C-terminal split intein (Ic). The precursor peptide comprises a target peptide covalently linked at its C-terminus via a peptide bond to an N-terminal split intein (In). The In and the Ic are of the same or cross-reacting intein (I); the Ic is from 4 to 7 contiguous amino acids, at least 4 of which are from the last beta-strand of the C-terminal region of an intein; the Ic is split from the intein at a site between the penultimate beta-strand and the last beta-strand of the C-terminal region of an intein; and the C-terminal Asn residue of the Ic is mutated to block transesterification. The reaction takes place under conditions allowing cleavage of the target peptide from the precursor peptide. Site specific cleavage may be done similarly by contacting a precursor peptide with an N-terminal split intein (In). The precursor peptide comprises a target peptide covalently linked at its N-terminus via a peptide bond to a C-terminal split intein (Ic), under conditions allowing cleavage of the target peptide from the precursor peptide. The In and the Ic are of the same or cross-reacting intein (I); the Ic is from 4 to 7 contiguous amino acids, at least 4 of which are from the last beta-strand of the C-terminal region of an intein; the Ic is split from the intein at a site between the penultimate beta-strand and the last beta-strand of the C-terminal region of an intein; and the C-terminal Asn residue of the Ic is mutated to block transesterification. In one embodiment, the precursor peptide comprises a further peptide which is covalently linked to the C-terminus of the In or is covalently linked to the N-terminus of the Ic. The further peptide may be an affinity binding peptide. In certain embodiments, the Ic is a small Ic (i.e. an SCI) from an intein selected from the group consisting of Ssp GyrB, Ssp DnaX, Ter DnaE3, and Ter ThyX. In other embodiments, the Ic is 6 contiguous amino acids. Specifically, the Ic may have the sequence GVFVHN (SEQ ID NO:63), GLLVHN (SEQ ID NO:64), GLIASN (SEQ ID NO:65), or GLVVHN (SEQ ID NO:66) in which the terminal Asn is mutated to block transesterification. Specifically the terminal Asn may be mutated to Alanine. In some embodiments, the cleavage of the target peptide from the precursor peptide is performed under reducing reaction conditions.

BRIEF DESCRIPTION OF THE DRAWINGS

Certain illustrative aspects of the invention are described herein in connection with the following description and drawings. These aspects are indicative of some of the ways in which the principles of the invention can be employed. The subject invention is intended to include all such aspects and their equivalents. Other advantages and novel features will become apparent from the following detailed description of the invention when considered in conjunction with the drawings.

FIG. 1 illustrates the SCI and SNI split inteins of this invention: construction schemes (top part) and sequence comparisons (bottom part). Conventional (previously known) split inteins have their split sites located near the middle of their corresponding contiguous intein sequences. This invention broke intein sequences at sites near the N- and/or C-termini, through recombinant DNA, and produced the SCI, SNI, and 3-piece split inteins. The sequence comparison includes examples of the split inteins of this invention. The six intein sequences (e.g. one named Ssp GyrB) are aligned by similarities, with the symbol "–" representing gaps introduced to maximize the alignment, the symbol "*" representing extra (optional) sequences that were deleted, and the symbol "//" representing splits in the intein sequence. In the Ssp DnaB intein, whose crystal structure is known, some of its β-strands are underlined. Three arrows point to split sites that were used in this invention to produce the split inteins. They include the S2 (before β2), S1 (after β2), and S11 (after β11) split sites that were used to produce the S2, S1, and S11 split inteins, respectively.

FIGS. 2A, 2B, 2C & 2D illustrate schemes of protein-peptide trans-splicing using the SCI and SNI split inteins. The C-terminal peptide splicing is designed to add a desired peptide (P) to the C-terminus of a target protein (TP), using a SCI split intein (e.g. the S11 split intein). It includes the production of a recombinant fusion protein (TP-$I_N$) and a synthetic peptide ($I_C$-P). The In and Ic together catalyzes a trans-splicing reaction, which excises the intein sequences and joins TP and P with a peptide bond. The N-terminal peptide splicing is designed to add P to the N-terminus of TP, using a SNI split intein (e.g. the S1 and S2 split inteins). The internal peptide splicing is designed to add P to an internal location of a target protein having an N-terminal part (N) and a C-terminal part (C). It uses both a SCI split intein (consisting of $I_{N1}$ and $I_{C1}$) and a SNI split intein (consisting of $I_{N2}$ and $I_{C2}$), with the small $I_{C1}$ and $I_{N2}$ flanking P in the synthetic peptide. The N and C can be in two separate recombinant proteins (N—$I_{N1}$ and $I_{C2}$-C), or they can be in a single recombinant protein (N-$I_{N1}$-L-$I_{C2}$-C) having a linker sequence (L) between $I_{N1}$ and $I_{C2}$.

FIGS. 3A, 3B, 3C & 3D illustrate schemes of polypeptide ligation and cyclization using the SCI, SNI, and 3-piece split inteins. The two-peptide splicing is designed to join two polypeptides (P1 and P2) with a peptide bond. One scheme use a 3-piece split intein consisting of a small In fused to P1, a small Ic fused to P2, and a larger middle-intein ($I_M$). Another scheme uses a SNI split intein (consisting of $I_{N1}$ and $I_{C1}$) together with a SCI split intein (consisting of $I_{N2}$ and $I_{C2}$), and a desired linker sequence (L) between $I_{C1}$ and $I_{N2}$ is incorporated into the ligated product. The peptide and protein cyclization is designed to join the two ends of a peptide or protein with a peptide bond in a controllable way. One scheme uses a 3-piece split intein (consisting of Ic, In, and IM), with the small Ic and In fused to the N- and C-terminus of the peptide or protein (P), respectively. The cyclization reaction is initiated only when the IM is added. Another scheme uses a SNI and a SCI split inteins, with the target protein (P) being flanked by $I_{C1}$ at the N-terminus and $I_{N2}$ at the C-terminus, and with a linker sequence (L) connecting the small $I_{C2}$ and $I_{N1}$ in a synthetic peptide. The cyclization reaction is initiated only when the synthetic peptide is added, and L is incorporated into the cyclized product.

FIG. 6 is a demonstration of internal peptide splicing in vitro. A, schematic illustration of the trans-splicing reactions, which were carried out in two steps as indicated. The split inteins and target proteins were same as in FIG. 5, but the two precursor proteins were separately expressed and purified, and the small peptide ($I_{C1}$-F-$I_{N2}$) contained the FLAG tag sequence (F). B, observation of the trans-spliced protein (M-F-T) and other products, through SDS-PAGE followed by Coomassie blue stain or Western blots using antibodies against the FLAG-tag (anti-F). Lanes 1, 2, and 3 show the partially purified precursor protein (M-$I_{N1}$) before splicing, after step 1 splicing, and after step 2 splicing, respectively.

FIG. 14 is a kinetic analysis of the N-cleavage of FIG. 13. The cleavage efficiency was calculated as the percentage of the precursor protein that had been converted to the cleavage product. A. Cleavage reactions in the presence of either Ic peptide (●), 10 mM DTT (■), or 100 mM DTT (▲). B. Cleavage reactions in the presence of either IC peptide +10 mM DTT (■), or IC peptide +100 mM DTT (▲). C. Cleavage reactions in the presence of a shorter IC peptide (sequence: GVFVHN) plus 10 mM (■) or 100 mM DTT (▲). D. The pseudo-first order rate constants of the N-cleavage plotted against the various DTT concentrations. Results from triplicate measurements are shown with error bars indicating standard deviations.

DETAILED DESCRIPTION OF EMBODIMENTS

Figure 4:
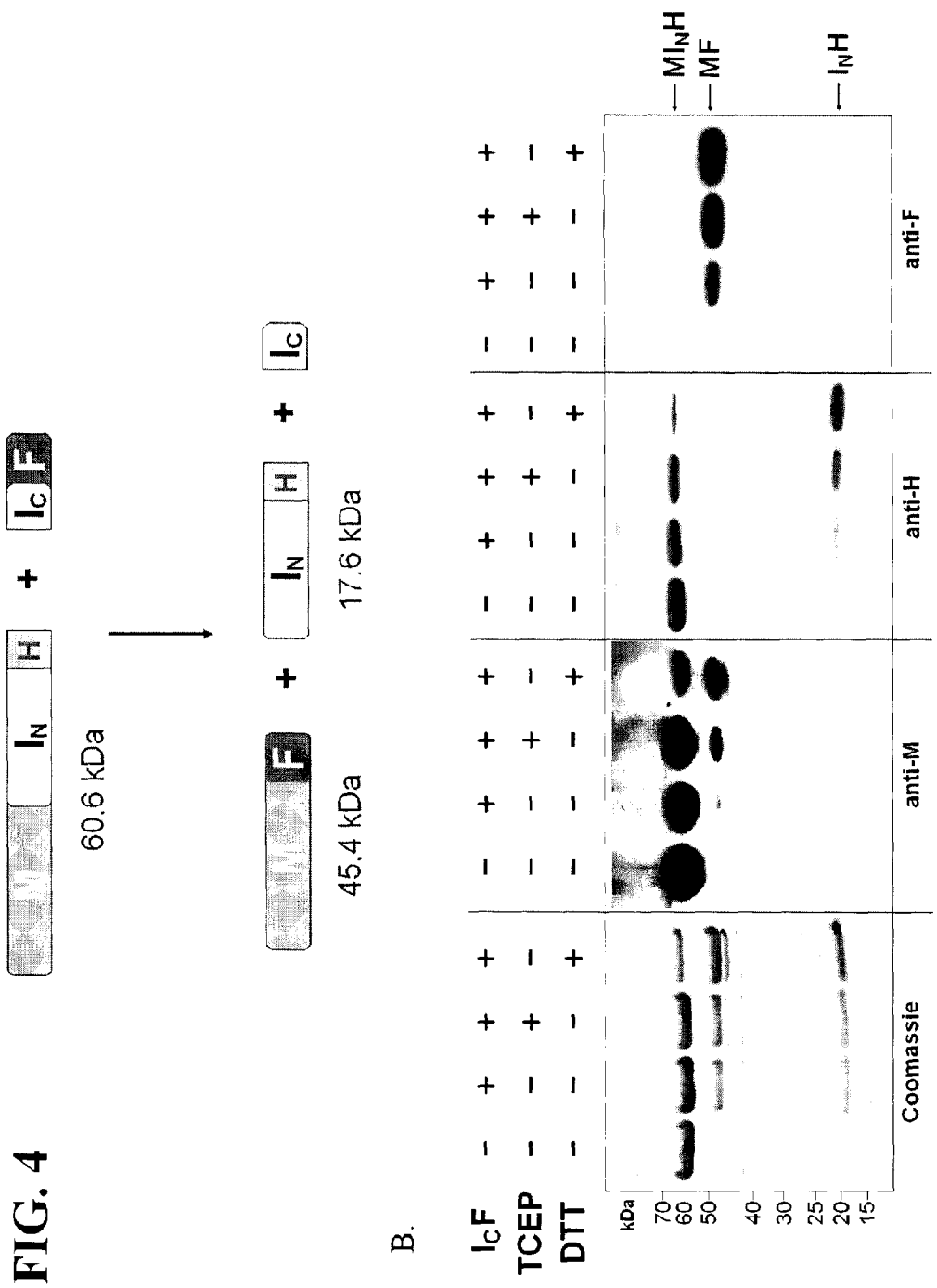
FIG. 4 is a demonstration of C-terminal peptide splicing using a SCI split intein (the Ssp GyrB S11 split intein). The top part shows A) schematic illustration of the trans-splicing reaction and B) analysis of the splicing products. The recombinant precursor protein (MI$_N$H) consisted of a maltose binding protein (M) as the target protein, the N-intein ($I_N$), and a His-tag (H, a 6-hisidine sequence) for affinity purification of the precursor protein. The synthetic peptide ($I_C$F) consisted of the small (6 aa) C-intein (Ic) and a sequence containing the FLAG tag (F). The MI$_N$H protein was incubated with or without the $I_C$F peptide and a reducing agent (DTT or TCEP) as indicated. The protein products were analyzed by SDS-PAGE, followed by staining with Coomassie blue, or by Western blotting using antibodies against the maltose binding protein (anti-M), the His-tag (anti-H), or the FLAG-tag (anti-F), as indicated. Positions of the precursor protein (MI$_N$H), the trans-spliced protein (MF), and the excised I$_N$H fragment are marked, while the excised Ic fragment is too small to be seen.

Intein-based methods of protein modification and ligation have been developed. An intein is an internal protein sequence capable of catalyzing a protein splicing reaction that excises the intein sequence from a precursor protein and joins the flanking sequences (N- and C-exteins) with a peptide bond [17]. Hundreds of intein and intein-like sequences have been found in a wide variety of organisms and proteins [18-19], they are typically 350-550 amino acids in size and also contain a homing endonuclease domain, but mini-inteins having only the ~140-aa splicing domain are sufficient for protein splicing [20-24]. The conserved crystal structure of mini-inteins (or the protein splicing domain) consists of ~12 beta-strands that form a disk-like structure with the two splicing junctions located in a central cleft [25-28].

The mechanism of protein splicing typically has four steps [29-30]: 1) an N—S or N—O acyl shift at the intein N-terminus, which breaks the upstream peptide bond and forms an ester bond between the N-extein and the side chain of the intein's first amino acid (Cys or Ser); 2) a transesterification relocating the N-extein to the intein C-terminus, forming a new ester bond linking the N-extein to the side chain of the C-extein's first amino acid (Cys, Ser, or Thr); 3) Asn cyclization breaking the peptide bond between the intein and the C-extein; and 4) a S—N or O—N acyl shift that replaces the ester bond with a peptide bond between the N-extein and C-extein.

Protein trans-splicing, catalyzed by split inteins, provides an entirely enzymatic method for protein ligation [31]. A split-intein is essentially a contiguous intein (e.g. a mini-intein) split into two pieces named N-intein and C-intein, respectively. The N-intein and C-intein of a split intein can associate non-covalently to form an active intein and catalyze the splicing reaction essentially in same way as a contiguous intein does. Split inteins have been found in nature and also engineered in laboratories [31-35]. As used herein, the term "split intein" refers to any intein in which one or more peptide bond breaks exists between the N-terminal and C-terminal amino acid sequences such that the N-terminal and C-terminal sequences become separate molecules that can non-covalently reassociate, or reconstitute, into an intein that is functional for trans-splicing reactions. Any catalytically active intein, or fragment thereof, may be used to derive a split intein for use in the methods of the invention. For example, in one aspect the split intein may be derived from a eukaryotic intein. In another aspect, the split intein may be derived from a bacterial intein. In another aspect, the split intein may be derived from an archaeal intein. Preferably, the split intein so-derived will possess only the amino acid sequences essential for catalyzing trans-splicing reactions.

As used herein, the "N-terminal split intein (In)" refers to any intein sequence that comprises an N-terminal amino acid sequence that is functional for trans-splicing reactions. An In thus also comprises a sequence that is spliced out when trans-splicing occurs. An In can comprise a sequence that is a modification of the N-terminal portion of a naturally occurring intein sequence. For example, an In can comprise additional amino acid residues and/or mutated residues so long as the inclusion of such additional and/or mutated residues does not render the In non-functional in trans-splicing. Preferably, the inclusion of the additional and/or mutated residues improves or enhances the trans-splicing activity of the In.

As used herein, the "C-terminal split intein (Ic)" refers to any intein sequence that comprises a C-terminal amino acid sequence that is functional for trans-splicing reactions. In one aspect, the Ic comprises 4 to 7 contiguous amino acid residues, at least 4 amino acids of which are from the last β-strand of the intein from which it was derived. An Ic thus also comprises a sequence that is spliced out when trans-splicing occurs. An Ic can comprise a sequence that is a modification of the C-terminal portion of a naturally occurring intein sequence. For example, an Ic can comprise additional amino acid residues and/or mutated residues so long as the inclusion of such additional and/or mutated residues does not render the In non-functional in trans-splicing. Preferably, the inclusion of the additional and/or mutated residues improves or enhances the trans-splicing activity of the Ic.

In some embodiments of the invention, a peptide linked to an Ic or an In can comprise an additional chemical moiety including, among others, fluorescence groups, biotin, polyethylene glycol (PEG), amino acid analogs, unnatural amino acids, phosphate groups, glycosyl groups, radioisotope labels, and pharmaceutical molecules. In other embodiments, a peptide linked to an Ic can comprise one or more chemically reactive groups including, among others, ketone, aldehyde, Cys residues and Lys residues.

The N-intein and C-intein of a split intein can associate non-covalently to form an active intein and catalyze the splicing reaction when an "intein-splicing polypeptide (ISP)" is present. As used herein, "intein-splicing polypeptide (ISP)" refers to the portion of the amino acid sequence of a split intein that remains when the Ic, In, or both, are removed from the split intein. In certain embodiments, the In comprises the ISP. In another embodiment, the Ic comprises the ISP. In yet another embodiment, the ISP is a separate peptide that is not covalently linked to In nor to Ic.

Split inteins may be created from contiguous inteins by engineering one or more split sites in the unstructured loop or intervening amino acid sequence between the ~12 conserved beta-strands found in the structure of mini-inteins [25-28]. Some flexibility in the position of the split site within regions between the beta-strands may exist, provided that creation of the split will not disrupt the structure of the intein, the structured beta-strands in particular, to a sufficient degree that protein splicing activity is lost.

In protein trans-splicing, one precursor protein consists of an N-extein part followed by the N-intein, another precursor protein consists of the C-intein followed by a C-extein part, and a trans-splicing reaction (catalyzed by the N- and C-inteins together) excises the two intein sequences and links the two extein sequences with a peptide bond. Protein trans-splicing, being an enzymatic reaction, can work with very low (e.g. micromolar) concentrations of proteins and can be carried out under physiological conditions.

Split-inteins have many practical uses including the production of recombinant proteins from fragments, the circularization of recombinant proteins, and the fixation of proteins on protein chips [15-16, 36, 49]. However, conventional split inteins are not suitable for ligation of peptides, because the ~110 amino acid N-intein and the ~35 amino acid C-intein are too large to be incorporated into synthetic peptides easily and economically. One previously reported split intein having a small (11 amino acid) N-intein has been found to be useful for adding a synthetic peptide to the N-terminus of target proteins [47-48]. However this split intein is not suitable for adding synthetic peptides to the C-terminus and internal positions of target proteins, which is the main reason for this invention.

Inteins can also be modified to carry out site-specific protein cleavages instead of splicing [14, 37-38], with cleavages at the N-terminus and the C-terminus of intein named N-cleavage and C-cleavage, respectively. Such modifications involve mutation of a conserved Asn residue at or near the C-terminus of the intein sequence to another amino acid, such as Ala, so as to inhibit the second step of the four-step splicing mechanism, namely the transesterification relocating the N-extein to the intein C-terminus, forming a new ester bond linking the N-extein to the side chain of the C-extein's first amino acid (Cys, Ser, or Thr).

Advantages of intein-based protein cleavage methods, compared to others such as protease-based methods, have been noted previously [16], and our methods using intein fragments retained many of these advantages. For example, the N-cleavage method may be used to generate an activated thioester at the C-terminus of a target protein, so that the target protein can be joined with another protein or peptide having an N-terminal Cys residue, using the expressed protein ligation method [12, 15, 39]. Unlike protease-based methods that cleave on the C-terminal side of specific recognition sequences, our intein-based N-cleavage method cleaves on the N-terminal side of the recognition sequence ($I_N$) and thus allows removal of the affinity purification domain (or tag) placed on the C-terminus of the target protein.

The intein-based N- and C-cleavage methods may also be used together on a single target protein to produce precise and tag-free ends at both the N- and the C-termini, or to achieve cyclization of the target protein (ligation of the N- and C-termini) using the expressed protein ligation approach.

We have demonstrated that the C-cleavage method could be used to generate an N-terminal Cys residue on a target protein, which is needed for the expressed protein ligation, although the Ssp DnaB intein is followed naturally with a Ser residue. These intein-based methods also have minimal if any risk of non-specific cleavages at unintended places, which is another advantage compared to some protease-based methods. Compared to previous methods that used contiguous inteins and often showed undesirable spontaneous cleavages, this invention uses intein fragments and completely avoids spontaneous cleavages.

Figure 12:
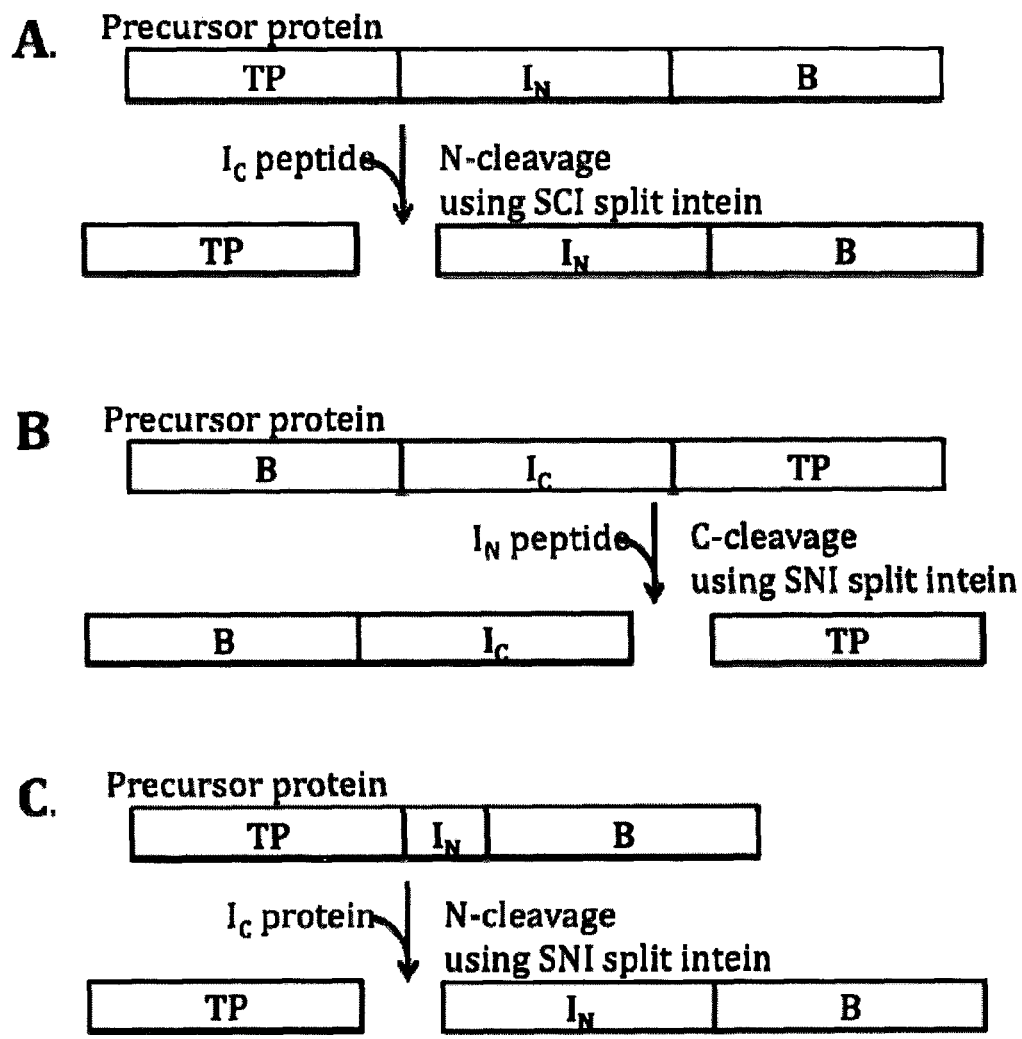
FIG. 12 illustrates schemes of controllable protein cleavages using the SCI and SNI split inteins. A recombinant precursor protein typically consists of a target protein (TP), an N-intein ($I_N$) or C-intein (Ic), and an optional affinity binder (B) for easy purification of the precursor protein, as indicated. N-cleavage at the intein's N-terminus, or C-cleavage at the intein's C-terminus, can be triggered by the addition of the complementing Ic or In as indicated.

Generally, the invention provides methods of construction of functional split inteins having small C-intein and/or small N-intein (see FIG. 1), and further provides methods of protein manipulations using the above split inteins (see FIGS. 2, 3, and 12). Compared to previously reported inteins, the small C- and N-inteins of this invention can be more easily produced in forms of, or as a part of, synthetic peptides, which permits new and improved intein-based methods of protein manipulations. The split inteins of this invention, compared to conventional split inteins, may also confer higher protein stability and solubility.

Split inteins having a small C-intein are sometimes referred to herein as SCI split inteins. Their sequences are derived by splitting contiguous intein sequences at a site near the C-terminus, which results in a small C-terminal piece called a C-intein (Ic) and the remaining N-terminal piece called a N-intein or In. Ic comprises amino acids from the C-terminal region of an intein and has splicing activity when in the presence of the remainder of the intein. The small C-intein is generally less than 15 amino acids, preferably smaller e.g. 12, 10, 8, 4 amino acids, and specifically 6 amino acids in the SCI split inteins demonstrated in this invention. A range of 4 to 7 amino acid small C-intein is contemplated which includes the 4-amino acid C-terminal beta strand, the C-terminal Asn, and the 2 residues defining the loop sequence between the β-strands. For comparison, previously reported C-inteins are larger than 30 amino acids.

Split inteins having a small N-intein are sometimes referred to herein as SNI split inteins. Their sequences are derived by splitting contiguous intein sequences at a site near the N-terminus, which results in a small N-terminal piece called a N-intein (In) and the remaining C-terminal piece called a C-intein (Ic). In comprises amino acids from the N-terminal region of an intein and has splicing activity when in the presence of the remainder of the intein. The resulting small N-intein is generally less than 20 amino acids, preferably smaller e.g. 18, 15, 12, 10, 5, 3 amino acids, and specifically 11-12 amino acids in the SNI S1 split inteins or 5 amino acids in the SNI S2 split inteins demonstrated in this invention. It is noted that, as shown for a few exemplified split inteins at the bottom of FIG. 1, the first beta-strand can consist of only the second and third amino acids and is not always apparent in intein structures. For comparison, previously reported N-inteins are generally larger than 100 amino acids. This invention provides multiple SNI split intein having small N-inteins, which permits new and improved methods of protein manipulations especially when used together with the SCI split inteins of this invention.

A 3-piece split intein is constructed by splitting an intein sequence both at a site near the N-terminus and at a site near the C-terminus, which results in a small N-intein as described above, a small C-intein as described above, and the remaining middle piece called a M-intein (IM). Specific examples of 3-piece split inteins having an 11-12 amino acid N-intein and a 6 amino acid C-intein are demonstrated in this invention. For comparison, the single previously reported 3-piece split intein has a 11 amino acid N-intein but a larger (>30 amino acid) C-intein.

In construction of the above split inteins, selecting the split sites can be done with the aid of intein sequence alignments and structural features, as illustrated for example in FIG. 1. Preferably, the split sites are located in less structured or loop sequences between the more structured or β-strands. Additional amino acids or sequences (e.g. an affinity tag) may be added at the split site and present on the resulting C-intein and/or N-intein, if this leads to desirable features such as easy purification, higher expression, and increased stability of the inteins and intein-containing proteins.

For construction of the above split inteins, the original intein sequences can be from either natural inteins or artificial inteins derived in laboratories. The original intein can be a bi-functional intein having a homing endonuclease domain additional to the splicing domain, a mini-intein lacking a complete homing endonuclease domain, or a split intein consisting of two or more intein pieces. The contiguous intein is preferably a mini-intein, in which a homing endonuclease domain is either naturally absent, artificially deleted, or replaced with other sequences. The first position of the intein sequence is preferably but not limited to a nucleophilic amino acid (e.g. Cys or Ser), and the amino acid immediately following the intein sequence (i.e. the first amino acid of the C-extein) is preferably a nucleophilic amino acid (e.g. Cys, Ser, or Thr). In the functional split inteins of this invention, amino acids of the above two positions need not match those of the original inteins, as has been demonstrated in this invention.

The methods of the invention relates to SCIs that have splicing activity when used in conjunction with In and IM. In one aspect, the SCI shows a splicing efficiency of at least 50% when tested in a trans-splicing activity assay in which the SCI is linked to the N-terminus of a first reporter polypeptide via a peptide bond, and then exposed to an N-precursor polypeptide under conditions that permit splicing to occur. The N-precursor polypeptide comprises a second reporter polypeptide linked via a peptide bond at its C-terminus to a corresponding N-terminal split intein. The presence of the second reporter polypeptide fused to the first reporter polypeptide is then detected, thereby indicating whether the SCI is functional. The efficiency of trans-splicing is defined as the percentage completion of the splicing reaction. For example, FIG. 4C illustrates kinetic analysis of spliced product formation for the reaction depicted in FIG. 4A and described in Examples 1 and 2. Preferably, the SCI shows a splicing efficiency of at least 60%, or at least 70%, or at least 80%, or at least 90% when tested in a trans-splicing activity assay.

Optionally, an affinity tag (e.g. His-tag) can be added to the intein sequence to allow affinity purification of the intein or intein-containing fusion proteins, and a marker (e.g. a green fluorescence protein) can be added to the intein sequence to facilitate selection or monitoring of the intein and intein-containing proteins. The affinity tag or marker may be added anywhere in the intein sequence but preferably in less structured loop sequences and in or near a location where a homing endonuclease domain normally resides.

For construction of the above split inteins, splitting the contiguous intein sequence is readily achieved through recombinant DNA and equivalent techniques. Gene expression methods, and chemical synthesis methods when feasible, may be used to produce the N-, M- and C-inteins and intein-containing peptides. In the recombinant methods, genes which express the desired intein or peptide are engineered by inserting a nucleic acid that encodes the intein-containing peptide precursor into an expression vector and expressing the precursor in an appropriate host. Any of a variety of expression vectors known to those of ordinary skill in the art may be employed. Expression may be achieved in any appropriate host cell that has been transformed or transfected with an expression vector containing a DNA molecule which encodes the recombinant intein-containing peptide precursor. Suitable host cells include prokaryotes, yeasts and higher eukaryotic cells. Preferably, the host cells employed are $E.$ $coli$, yeasts or a mammalian cell line such as CHO.

As used herein, the term "peptide" or "protein" or "polypeptide" comprises at least one amino acid when linked to a split intein. When the "peptide" or "protein" or "polypeptide" comprises two or more contiguous amino acids, the two or more contiguous amino acids are covalently linked together by peptide bonds. The terms peptide, polypeptide and protein may be used interchangeably. Peptides may be from any source and may include, for example, fragments or full-length sequences of enzymes, antibodies, antibody fragments, and pharmaceutical proteins. In some embodiments of the invention, a peptide (i.e. a single amino acid or a polymer of two or more amino acids) can comprise an additional chemical moiety including, among others, fluorescence groups, biotin, polyethylene glycol (PEG), amino acid analogs, unnatural amino acids, phosphate groups, glycosyl groups, radioisotope labels, and pharmaceutical molecules. In other embodiments, a peptide can comprise one or more chemically reactive groups including, among others, ketone, aldehyde, Cys residues and Lys residues.

The split inteins may be improved in desirable characteristics including activity, efficiency, generality, and stability. These improvements may be achieved through site-directed mutagenesis or modifications of the intein sequences based on rational design, and they may also be achieved through directed evolution using methods like functional selection, phage display, and ribosome display.

In this invention we have produced more than 13 functional SCI, SNI and 3-piece split inteins, after making and testing more than 50 split intein constructs (see FIG. 1 and Example 1). Previously only a single SNI split intein has been reported. Armed with knowledge of this invention, additional split inteins can readily be produced in similar ways. All of the 13 split inteins have been shown to have protein trans-splicing activities in $E.$ $coli$ cells, using model proteins including maltose binding protein and thioredoxin. Most of these split inteins were shown to do the trans-splicing also in vitro and with different target proteins (N- and C-exteins). Many of these split inteins were found to not cross-react in vivo or in vitro, therefore they may be used in a mixture to trans-splice different target proteins in a specific manner. Most of these split inteins were also found to work with either Cys or Ser as the first amino acid of the C-extein, which expanded their general capabilities. Most of these split inteins were also shown to be capable of controllable site-specific N- and C-cleavages when splicing is prevented, which makes them useful in methods including protein purification and expressed protein ligation.

By "cross-react" is meant that the inteins are sufficiently similar to allow the split inteins derived from them (In, Ic and IM) to be compatible in a trans-splicing reaction. For example, In from intein A may be sufficiently similar to In from intein B such that In from both A and B would function with Ic from A; inteins A and B are said to cross-react. In choosing a particular set of inteins for splicing, the split inteins derived from the same intein (A) or derived from a cross-reacting intein (A') may be used to effect splicing at a specific site X, and the split inteins derived from the same intein (B) or derived from a cross-reacting intein (B') may be used to effect splicing at another specific site Y. Where splicing is to take place at both sites X and Y in the same reaction environment, the inteins A and A' should be chosen as not to cross-react with the inteins B and B'.

The invention provides methods of protein manipulations using the above split inteins. These methods include but not limited to the following three groups. Group 1 includes C-terminal peptide splicing, N-terminal peptide splicing, and internal peptide splicing, as illustrated in FIG. 2. Group 2 includes two-peptide splicing and controllable protein or peptide cyclization, as illustrated in FIG. 3. Group 3 includes controllable protein N- and/or C-cleavages, as illustrated in FIG. 12. All three groups of methods of protein manipulations, or their modified versions, may be used in solution, on a solid surface, outside cells, on cell surface, and inside cells.

The first group of methods is of protein-peptide trans-splicing using the SCI and/or the SNI split inteins (see FIG. 2). These methods are made possible by the small C- and N-inteins of the SCI and SNI split inteins, respectively, because the small C- and N-inteins can be more easily incorporated into small synthetic peptides and are more amenable to chemical synthesis. These methods are useful for addition of a variety of desired chemical moieties to proteins of interest site-specifically at either terminal or internal locations through an enzymatic (trans-splicing) reaction, because the synthetic peptide can be made to contain any chemical moiety available to chemical synthesis.

The C-terminal peptide splicing is designed to add a desired peptide (P) to the C-terminus of a target protein (TP), using a SCI split intein (e.g. the S11 split intein). It includes the production of a recombinant precursor protein (TP-$I_N$) and a synthetic peptide ($I_C$-P). The In and Ic together catalyzes a trans-splicing reaction, which excises the intein sequences and joins TP and P with a peptide bond. The In of the precursor protein may contain additional functional groups at its C-terminus or an internal location, and examples of desirable functional group include an affinity tag and a marker. When the In contains an affinity tag, the precursor protein TP-$I_N$ may be bound to and purified on affinity beads or column, the trans-splicing reaction with $I_C$-P may then be carried out on the beads or column, and the trans-spliced product (TP-P) is automatically released from the beads or column in a purified form.

The N-terminal peptide splicing is designed to add P to the N-terminus of TP, using a SNI split intein (e.g. the S1 and S2 split inteins). It includes the production of a recombinant precursor protein ($I_C$-TP) and a synthetic peptide (P-$I_N$). The In and Ic together catalyzes a trans-splicing reaction, which excises the intein sequences and joins TP and P with a peptide bond. The Ic of the precursor protein may contain additional functional groups at its N-terminus or an internal location, and examples of desirable functional group include an affinity tag and a marker. When the Ic contains an affinity tag, the precursor protein $I_C$-TP may be bound to and purified on affinity beads or column, the trans-splicing reaction with P-$I_N$ may then be carried out on the beads or column, and the trans-spliced product (P-TP) is automatically released from the beads or column in a purified form.

The internal peptide splicing is designed to add P to an internal location of a target protein that has an N-terminal part (N) and a C-terminal part (C). It uses both a SCI split intein (consisting of $I_N$1 and $I_C$1) and a SNI split intein (consisting of $I_N$2 and $I_C$2), with the small $I_C$1 and $I_N$2 flanking P in the synthetic peptide. The N and C can be in two separate recombinant proteins (N-$I_N$1 and $I_C$2-C), or they can be in a single recombinant protein (N-$I_N$1-L-$I_C$2-C) that has a linker sequence (L) between $I_N$1 and $I_C$2. The $I_N$1, $I_C$2, and L sequences may contain functional entities such as an affinity tag for protein purification and a marker for protein monitoring. The trans-splicing reactions may also be carried out on affinity beads or column to simplify purification of the desired protein product.

In the above methods, the synthetic peptides may contain any chemical moieties to be added to the target protein. Examples of chemical moieties include among others, fluorescence groups, biotin, polyethylene glycol (PEG), amino acid analogs, unnatural amino acids, phosphate groups, glycosyl groups, radioisotope labels, and pharmaceutical molecules. The synthetic peptides may also contain one or more chemically reactive groups that are preferably absent in the target protein. Examples of the chemically reactive groups include ketone, aldehyde, Cys, and Lys. After the peptides have been trans-spliced into the target protein, desired chemical moieties can be linked site-specifically to the chemically active groups in a site-specific manner.

In the above methods, the target protein can be any polypeptides of interest. Examples of target proteins include enzymes, antibodies, antibody fragments, and pharmaceutical proteins. The TP, P, N, and C may or may not be or derived from parts of the same protein.

In the above methods, the peptide P may be replaced with an expressed or recombinant polypeptide, which may or may not contain post-translational modifications.

In the above methods, the C-terminal, N-terminal, and internal peptide splicing reactions may be used in any combination or in tandem to add multiple or different Ps to multiple or different locations of one or more TPs or segments of TPs. One or more of these splicing reactions may also be used in combination with other methods of protein manipulations especially the method of expressed protein ligation.

In this invention we provided the first known demonstration of internal peptide splicing (see Example 3), using a model target protein consisting of a maltose binding protein and thioredoxin. An expressed and His-tag-containing polypeptide was successfully spliced into the target protein in E. coli cells, and a synthetic and flag-containing peptide was successfully spliced into the target protein in vitro. We also provided demonstrations of C-terminal peptide splicing using different target proteins including a maltose binding protein, a green fluorescence protein, and a transferrin receptor (see Example 5). The used peptides contained a Flag-tag, a fluorophore, or a biotin. The splicing reactions were carried in solution, on beads or column, and on live mammalian cells. The resulting fluorescence labeling of proteins can be useful for monitoring protein structure, folding, and cellular trafficking. The resulting biotin labeling of proteins can be useful for protein fixation on surfaces including streptavidin-coated microchips.

The second group of methods includes methods of two-peptide splicing (see FIG. 3, top part), which are designed to join two polypeptides (P1 and P2) with a peptide bond. One method uses a 3-piece split intein that consists of a small N-intein (In), a small C-intein (Ic), and a larger middle intein (IM). Two polypeptides (synthetic or expressed), P1-$I_N$ and $I_C$-P2 are incubated with IM to achieve a trans-splicing reaction, which joins P1 and P2 with a peptide bond. Another method uses a combination of a SNI split intein (small $I_N$1, large $I_C$1) and a SCI split intein (large $I_N$2, small $I_C$2). This involves a fusion protein containing a linker sequence L flanked by $I_C$1 and $I_N$2, a polypeptide (synthetic or expressed) P1-In1, and another polypeptide (synthetic or expressed) $I_C$2-P2. These three molecules together undergo two trans-splicing reactions and produce the ligated peptide P1-L-P2. The linker sequence L may contain or be replaced with any other polypeptide sequences of interest to be contained in the spliced product.

In the above methods, the P1 and P2 may be synthetic peptides and contain any chemical moieties including among others, fluorescence groups, biotin, polyethylene glycol (PEG), amino acid analogs, unnatural amino acids, phosphate groups, glycosyl groups, radioisotope labels, and pharmaceutical molecules. The synthetic peptides may also contain one or more chemically reactive groups that are preferably absent in parts of the spliced polypeptide. Examples of the chemically reactive groups include ketone, aldehyde, Cys, and Lys. After the peptides have been trans-spliced into the target protein, desired chemical moieties can be linked site-specifically to the chemically active groups in a site-specific manner.

In the above methods, P1 and/or P2 may be replaced with an expressed or recombinant polypeptide, which may or may not contain post-translational modifications. P1 and/or P2 may be any polypeptides of interest, with examples like enzymes, antibodies, antibody fragments, and pharmaceutical proteins. The P1, P2, and L may or may not be derived from the same protein.

In the above methods, the IM may function as a substrate-specific polypeptide ligase that can catalyze multiple rounds of the splicing reaction. The IM and $I_C$1-L-$I_N$2 proteins may contain additional functional groups such as an affinity tag for protein purification and a marker for protein monitoring.

The above methods may be used in any combination or in tandem to join multiple or different polypeptides. They may also be used in combination with other methods of protein manipulations such as the method of expressed protein ligation.

The second group of methods also includes methods of controllable peptide or protein cyclization (see FIG. 3, bottom part), which are designed to join the two ends of a peptide or protein with a peptide bond or a linker in a controllable way. One scheme uses a 3-piece split intein (consisting of Ic, In, and IM), with the small Ic and In fused to the N- and C-terminus of the peptide or protein (P), respectively. The cyclization reaction is initiated only when the IM is added, which may function as a substrate-specific polypeptide ligase that can catalyze multiple rounds of the splicing reaction. Another scheme uses a SNI and a SCI split inteins together, with the target protein or peptide (P) being flanked by $Ic_1$ at the N-terminus and $I_{N2}$ at the C-terminus in a recombinant protein, and with a linker sequence (L) connecting the small $I_{C2}$ and $I_{N1}$ in a synthetic peptide. The cyclization reaction is initiated only when the synthetic peptide is added, and L is incorporated into the cyclized product. The linker sequence L may contain or be of any polypeptide sequence of interest to be contained in the cyclized product. The L-containing peptide may also be in form of an expressed polypeptide.

In the above methods, the P and/or L sequences may be completely or partially randomized genetically or through chemical synthesis to produce a library of cyclized polypeptides that can be subjected to functional or genetic screening or selection for desired functional entities such as protein aptamers.

In the above methods, the P and/or L as parts of synthetic peptides may be made to contain any chemical moieties including among others, fluorescence groups, biotin, polyethylene glycol (PEG), amino acid analogs, unnatural amino acids, phosphate groups, glycosyl groups, radioisotope labels, and pharmaceutical molecules. The synthetic peptides may also contain one or more chemically reactive groups that are preferably absent in parts of the spliced polypeptide. Examples of the chemically reactive groups include ketone, aldehyde, Cys, and Lys. After the peptides have been trans-spliced into the target protein, desired chemical moieties can be linked site-specifically to the chemically active groups in a site-specific manner.

The third group of methods is for controllable site-specific protein cleavages using the SCI and SNI split inteins (see FIG. 12). In one scheme (FIG. 12A), the recombinant precursor protein (TP-IN-B) consists of a target protein (TP), the N-intein (IN) of a SCI split intein, and an optional affinity binder (B) for easy purification of the precursor protein. The precursor protein is devoid of spontaneous cleavage or splicing during its expression and purification. A site-specific N-cleavage at the N-terminus of In of the precursor protein can be triggered by the addition of the Ic peptide, which releases the target protein. In a second scheme (FIG. 12B), the recombinant precursor protein (B-Ic-TP) consists of a target protein (TP), the C-intein (Ic) of a SNI split intein, and an optional affinity binder (B) for easy purification of the precursor protein. The precursor protein is devoid of spontaneous cleavage or splicing during its expression and purification. A site-specific C-cleavage at the C-terminus of Ic of the precursor protein can be triggered by the addition of the In peptide, which releases the target protein. In a third scheme (FIG. 12C), the recombinant precursor protein (TP-$I_N$-B) consists of a target protein (TP), the N-intein ($I_N$) of a SNI split intein, and an optional affinity binder (B) for easy purification of the precursor protein. The precursor protein is devoid of spontaneous cleavage or splicing during its expression and purification. A site-specific N-cleavage at the N-terminus of 1n of the precursor protein can be triggered by the addition of the Ic protein, which releases the target protein.

In the above cleavage methods, the target protein may be any polypeptides of interest. Examples of target proteins include enzymes, antibodies, antibody fragments, and pharmaceutical proteins.

In the above cleavage methods, the affinity binder may be, but is not limited to, a His-tag (6 histidines), a chitin binding domain, a maltose binding protein, and a glutathione-S-transferase.

In the above cleavage methods, the cleavage reactions may be carried out with the precursor protein being in solution, bound to affinity beads or column, anchored to cell membrane or phage surface, and inside or outside cells.

In the above cleavage methods, the N-cleavage and the C-cleavage may be used together on a single target protein (TP) to permit tandem purifications of the precursor protein (B1-$I_C$1-TP-$I_{N2}$-B2) using two different affinity binders (B1 and B2) sequentially. Then an $I_{N1}$ peptide is used to trigger C-cleavage after $I_d$ of the precursor protein, and $I_{Ce}$ peptide (or protein) is used to trigger N-cleavage before $I_{N2}$ of the precursor protein, simultaneously or sequentially, to generate precise terminus on both ends of the target protein.

In the above cleavage methods, the N-cleavage reactions may be carried out in presence of the thiol compound MESNA or its equivalent to generate a thioester on the C-terminus of the released target protein, which may be useful in subsequent applications such as expressed protein ligation.

In the above cleavage methods, DTT or its equivalent may be used to enhance the cleavage reactions and, in some cases, to trigger the cleavage reactions without the In or Ic peptide.

In the above cleavage methods, the Ic and the In may have exactly the corresponding Ic and In sequences, respectively, but they may also have modifications and additions, provided that the cleavage activities are maintained or enhanced without splicing.

EXAMPLES

The invention is herein further described with reference to the following, non-limiting, examples.

Example 1

Construction of SCI, SNI, and 3-piece Split Inteins Having Trans-splicing Activities SCI and SNI split inteins, unlike conventional split inteins, have a small C-intein and a small N-intein, respectively, as illustrated in FIG. 1. A 3-piece split intein has both a small C-intein and a small N-intein, in addition to an M-intein. To produce these novel split inteins, we designed modifications of more than fifteen selected natural inteins by splitting each contiguous intein sequence at certain designed split sites near the N-terminus and/or the C-terminus of the intein sequence, through recombinant DNA. The resulting split inteins were tested functionally to find ones showing the desired protein trans-splicing activity.

Working from the coding sequence of each intein, the homing endonuclease domain sequence (if present) was either deleted or replaced with a His-tag (6 histidines) sequence to produce a mini-intein, based on previously described domain predictions [18, 40-41]. Each mini-intein sequence was then split at one or more of the following split sites: the S11 site near the C-terminus for producing SCI split intein, the S1 or S2 sites near the N-terminus for producing SNI split intein, or both the S1 and the S11 sites for producing 3-piece split intein. These split sites were designed through protein sequence alignments with inteins of known crystal structures, such that the split sites were located in less structured loop sequences between β-strands. An example of the sequence alignment is shown in FIG. 1, where several mini-intein sequences are aligned to the Ssp DnaB mini-intein that has a known crystal structure [28].

For functional tests in *E. coli* cells and in vitro, each split intein construct was expressed in *E. coli* using the previously described pMST plasmid expression system [42]. In this system, the intein was flanked by a maltose binding protein (Sequence M) in the N-extein and a thioredoxin (Sequence T) in the C-extein, and the gene expression was from an IPTG-inducible Ptac promoter. For a SCI or SNI split inteins, the intein coding sequence was split at the chosen site to create a two-gene operon, by adding a spacer sequence containing sequentially a stop codon, a ribosome binding site (Shine-Dalgarno sequence), and a start codon. In this operon, the first gene encoded the N-precursor protein consisting of the M sequence (N-extein) followed by the N-terminal piece of the intein (N-intein or $I_N$), and the second gene encoded the C-precursor protein consisting of the C-terminal piece of the intein (C-intein or Ic) followed by the T sequence as C-extein. For a 3-piece split intein, the intein coding sequence was split at the two chosen sites to create a 3-gene operon, by adding the above spacer sequence at both split sites. In this operon, the first gene encoded the N-precursor protein consisting of M followed by $I_N$, the second gene encoded the middle piece of the intein (M-intein or $I_M$), and the third gene encoded the C-precursor protein consisting of 1c followed by the T. Similar gene constructs had been used in previous studies of split-inteins [42], which allowed easy expression and identification of the protein products.

Each plasmid was introduced into *E. coli* cells to produce the corresponding proteins after IPTG induction, the resulting total cellular proteins were resolved through SDS-PAGE, and relevant protein bands were identified by their predicted sizes and through Western blotting. Proteins were quantified by measuring the intensity of the corresponding signal on Western blots, and the efficiency of splicing was calculated as the ratio of the spliced protein over the total protein (the spliced protein plus the remaining precursor protein). The C-precursor protein was used in estimating the efficiency of trans-splicing, because the N-precursor protein existed in excessive amounts due to its higher expression level as the first gene of the two-gene operon.

More than 13 functional SCI, SNI and 3-piece split inteins were discovered in the above functional test, among more than 30 split intein constructs tested (Table 1). Those showing a high (>60%) efficiency of trans-splicing included the Ssp GyrB S11 split intein, the Ssp DnaX S11 split intein, the Ter ThyX S11 split intein, the Ter DnaE-3 S11 split intein, the Rma DnaB S1 split intein, the Cne Prp8 S1 split intein, the Ssp GyrB S1 split intein, the Ssp DnaX S1 split intein, the Ter ThyX S1 split intein, and the Ter DnaE-3 S1 split intein. Those showing a lower (<50%) efficiency of trans-splicing included the Ter DnaE3 S2 split intein, the Ssp DnaX 3-piece split intein, and the Ter ThyX 3-piece split intein.

Some of the above inteins were tested for compatibility with certain amino acids immediately next to the intein and for possible cross-reactivity among different split inteins. It was found that the Ssp DnaX, Ter ThyX, Cne Prp8, and Ter DnaE-3 inteins could work with either Cys or Ser as the first amino acid of the C-extein. It was also found that the Cne Prp8 intein could work with Thr as the first amino acid of the C-extein. It was also found that the Ter ThyX intein could work with Ser as the first amino acid of both the C-extein and the intein. It was further found that the following pairs of S1 split inteins did not cross react: the Ssp GyrB and the Ssp DnaX, the Ssp GyrB and the Ter ThyX, the Rma DnaB and the Ter ThyX, the Ssp DnaX and the Ter ThyX. It was also found that the following pairs of S11 split inteins did not cross react: the Ssp GyrB and the Ssp DnaX, the Ssp GyrB and the Ter ThyX, the Ssp DnaX and the Ter ThyX.

Figure 4A:
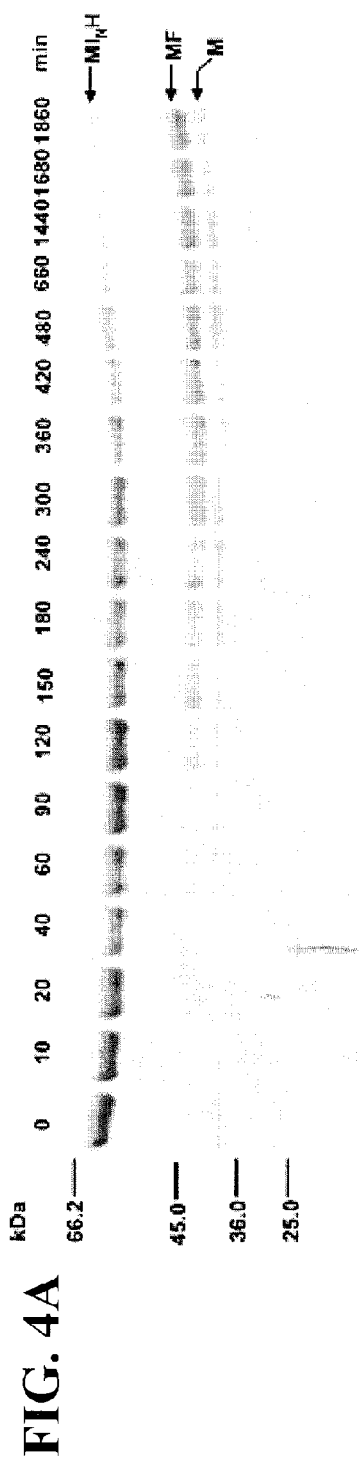
FIG. 4C shows a time course of the above trans-splicing reaction in presence of $I_C$F and ECEP.
Figure 4B:
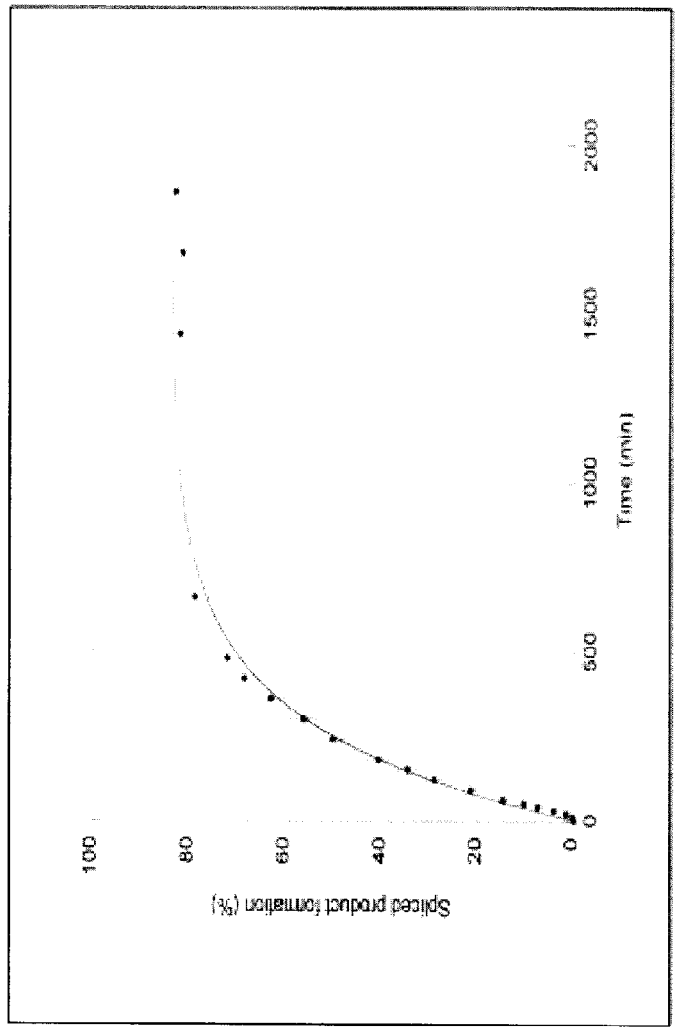

The Ssp GyrB S11 split-intein was further shown to trans-splice a recombinant N-precursor protein with a synthetic peptide in vitro (FIG. 4, top part). The N-precursor protein $MI_NH$ consisted of a maltose binding protein (M), the N-intein ($I_N$), and a His-tag sequence (H). The synthetic peptide ($I_CF$) is 30 aa in length with the following sequence: GVFVHNSADYKDDDDKSGCLAGDTLITLAS [SEQ ID NO:73]. It contains the Ic sequence (GVFVHN; SEQ ID NO:63) followed by a C-extein, and the C-extein sequence starts with an serine residue required for splicing and contains the FLAG epitope (DYKDDDDK; SEQ ID NO:74) for easy detection. If the trans-splicing occurs, the FLAG-containing C-extein (F) will be transferred onto the C-terminus of the maltose binding protein (M), producing the spliced protein (MF). Simultaneously, the N-intein piece ($I_NH$) will be released from the precursor protein and the C-intein (Ic) released from the synthetic $I_CF$ peptide. The predicted products of the above protein-peptide trans-splicing were observed after Coomassie Blue staining and identified through Western blotting. As expected, the spliced protein MF was recognized both by anti-M and anti-F antibodies, the N-terminal intein piece $I_NH$ was recognized only by the anti-H antibody, and the N-precursor protein $MI_NH$ was recognized both by anti-M and anti-H antibodies. This trans-splicing reaction was enhanced by the addition of reducing agents (TCEP and DTT), as indicated by the increased amounts of the spliced protein. Over 80% of the N-precursor protein was converted into the spliced protein in the presence of 1 mM DTT after 11 hours of incubation with the synthetic peptide. A minor protein band corresponding to the M part of the N-precursor protein ($MI_NH$) was also observed, suggesting that a small amount of the N-precursor protein underwent N-cleavage (i.e. peptide bond breakage at N-terminus of the In sequence) instead of trans-splicing.

The rate constant of the above trans-splicing reaction was also determined (FIG. 4C). The purified N-precursor protein was incubated with a 10-fold molar excess of the $I_CF$ peptide to achieve a pseudo-first order reaction regarding the N-precursor protein. The reaction products were resolved through SDS-PAGE, visualized by Coomassie Blue staining, and quantified through laser scanning and gel documentation. The amount of the spliced product was calculated as a percentage of the starting amount of N-precursor protein. The percentage of spliced product formation was plotted against time from a series of measurements over a 31-hour period. The plot was fitted to the pseudo-first order reaction equation of $P=P_0(1-e^{-kt})$ [43], and the rate constant ($k_{obs}$) was determined to be $(6.9\pm2.2)\times10^{-5}s^{-1}$.

Example 2

Experimental Procedures of Example 1

Mini-intein plasmid construction—Each mini-intein was constructed by fusing the N- and C-terminal coding sequences of the corresponding natural intein [18]. To make the Ssp GyrB mini-intein, for example, the N-terminal segment was PCR-amplified from *Synechocystis* sp. PCC6803 genomic DNA using a pair of oligonucleotide primers (5'-CTC GAG GGC GGT TGT TTT TCT GGA GAT ACA TTA GTC GC-3' [SEQ ID NO:75] and 5'-CAT ATG ACC AGA ATC TTC CGT AGT CGA AAT-3' [SEQ ID NO:76]). The C-terminal segment was obtained similarly, using the primer pair (5'-CAT ATG GAA GCA GTA TTA MT TAC MT CAC AG-3' [SEQ ID NO:77] and 5'-GAC CGG TCT CGC CAG CGC TGT TAT GGA CAA ACA CTC-3' [SEQ ID NO:78]). These segments were digested with appropriate restriction enzymes (XhoI, NdeI, and AgeI) and were placed in the pMST plasmid [42] between the XhoI and AgeI sites, creating the pMSG plasmid. This plasmid contains a maltose-binding protein as the N-extein and thioredoxin as the C-extein. For mini-inteins containing a His-tag, the His-tag coding sequences were inserted through inverse PCR at or near the location where the homing endonuclease domain had been deleted. DNA sequencing was used to confirm the sequence of all plasmids.

Split intein plasmid construction—Each split intein was constructed by inserting a spacer sequence at the specific split site in the coding sequence of the mini-intein. To make the Ssp GyrB S11 split intein, for example, a spacer sequence was inserted into the mini-intein coding sequence at the S11 split site by inverse PCR as described previously [42]. The spacer DNA sequentially contains a stop codon, a ribosome binding site, and a start codon, and has the following sequence: 5'-TAA TTA ACT TAT AAG GAG GM AAA CAT ATG [SEQ ID NO:79]. This creates a two-gene operon where the N-protein containing the maltose-binding protein and N-intein is followed by the C-protein containing the C-intein and thioredoxin. To produce a plasmid expressing the N-protein only (pMINH), the coding sequence of a His-tag (six histidines) was added to the 3' end of the In coding sequence through inverse PCR using the primer pair (5'-CAT CAC CAC CAT CAC CAT TM TTA ACT TAT AAG GAG GM MA CAT ATG-3' [SEQ ID NO:80] and 5'-CGT TGC CM AGC MA ATT GTG-3' [SEQ ID NO:81]), and the C-protein was deleted from the pMSG-S11 plasmid through digestion with NdeI-HindIII, followed by filling-in and blunt-end ligation.

Protein splicing in *Escherichia coli* cells—Each expression plasmid was introduced into *E. coli* cells (DH5α strain). Subsequent protein expression, gel electrophoresis and Western blotting were carried out as previously described [42]. Briefly, cells were grown to late log phase ($A_{600}$=0.5), IPTG was added to a final concentration of 0.8 mM to induce protein expression for 3 hours at 37° C. or for ~16 hours at room temperature, cells were harvested and lysed in a SDS- and DTT-containing buffer in a boiling water bath, total cellular proteins were analyzed through SDS-PAGE, and protein bands were visualized by staining with Coomassie Brilliant Blue R-250. Western blotting was carried out with either anti-MBP (maltose binding protein) monoclonal antibody (New England Biolabs) or anti-thioredoxin monoclonal antibody (Invitrogen), using the Enhanced Chemi-Luminescence detection kit (GE Healthcare). Intensity of protein band was estimated using a gel documentation system (Gel Doc 1000 coupled with Molecular Analyst software, Bio-Rad).

In vitro protein-peptide trans-splicing—The N-precursor protein ($MI_NH$) was expressed in *E. coli* as above and affinity-purified using amylose resin according to manufacturer's instructions (New England Biolabs). The synthetic peptide ($I_CF$) was purchased from EZ Biolab. For in vitro trans-splicing, 20 μM of the $MI_NH$ protein was incubated with 200 μM of the $I_CF$ peptide in a splicing buffer (20 mM Tris-HCl, 150 mM NaCl, 1 mM EDTA; pH 8.0) in the presence or absence of 0.1 mM TCEP or 1.0 mM DTT at room temperature for a specified length of time. Splicing products were analyzed through SDS-PAGE in the presence of DTT and visualized either by staining with Coomassie Brilliant Blue R-250 or Western blotting using an anti-MBP antibody (see above), an anti-FLAG antibody (Sigma), or an anti-His-tag antibody (Roche).

Example 3

Demonstration of Internal Peptide Splicing and Protein Cyclization

Figure 5:
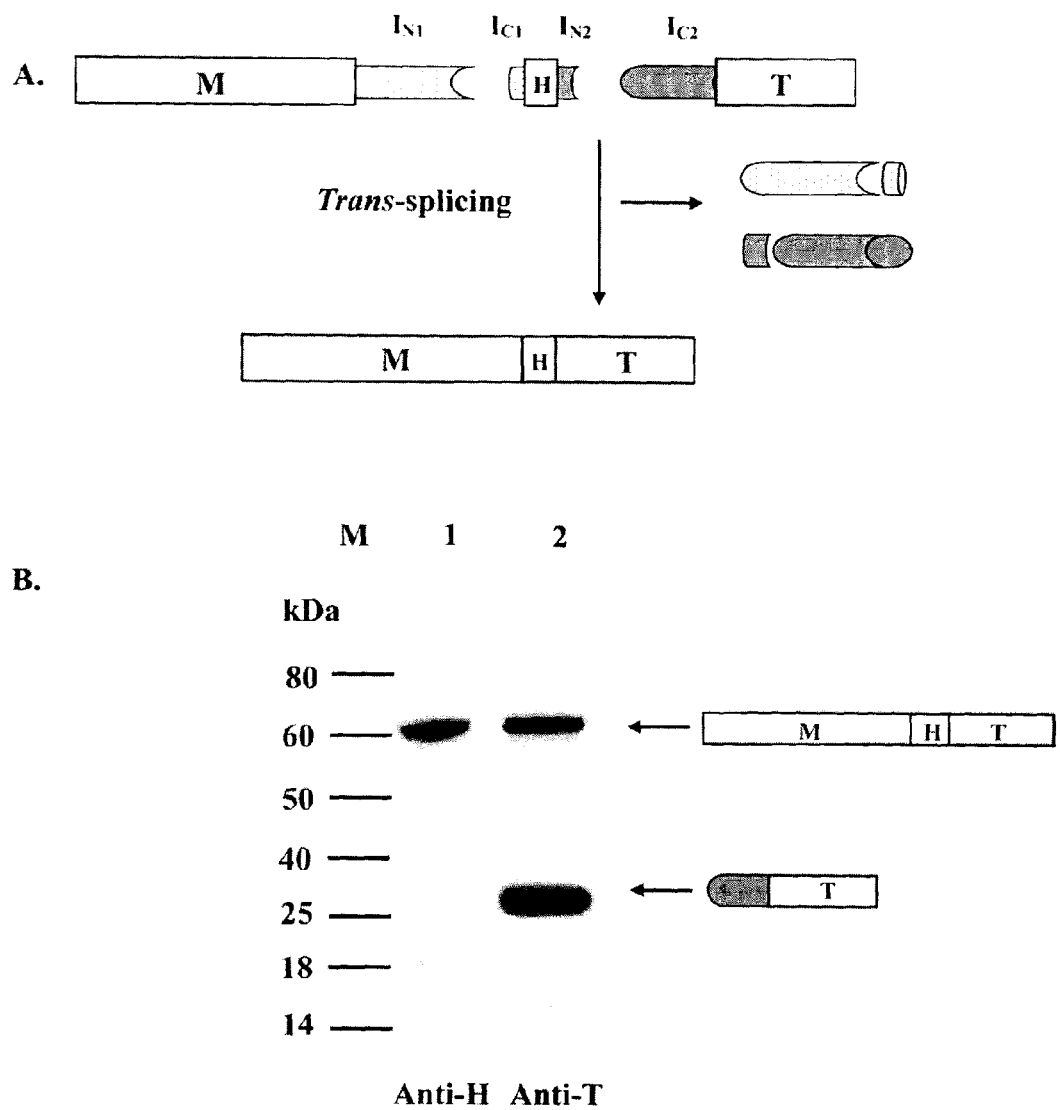
FIG. 5 is a demonstration of internal peptide splicing in *E. coli* cells, using a SCI and a SNI split inteins. A, schematic illustration of the trans-splicing reaction. The Ssp GyrB S11 split intein ($I_{N1}$ and $I_{C1}$) and the Rma DnaB S1 split intein ($I_{N2}$ and $I_{C2}$) were used to trans-splice a His-tag sequence (H) between a maltose binding protein (M) and a thioredoxin protein (T). The two precursor proteins (M-$I_{N1}$ and $I_{C2}$-T) and the small peptide ($I_{C1}$-H-$I_{N2}$) were co-expressed in the same *E. coli* cell to allow the trans-splicing to occur. B, observation of the trans-spliced product (M-H-T) on Western blots using antibodies against the His-tag (anti-H) and thioredoxin (anti-T) as indicated.

The scheme of internal protein splicing of FIG. 2 was demonstrated initially in *E. coli* cells. The Ssp GyrB S11 split intein and the Rma DnaB 51 split intein were used together to trans-splice three precursor polypeptides constructed using recombinant DNA (FIG. 5). The M-precursor is a maltose binding protein fused to the N-intein of the Ssp GyrB S11 split intein (SEQ ID NO:27), the T-precursor is a thioredoxin protein fused to the C-intein of the Rma DnaB S1 split intein (SEQ ID NO:29), and the H-precursor is a His-tag sequence flanked by the small C-intein of the Ssp GyrB S11 split intein and the small N-intein of the Rma DnaB S1 split intein (SEQ ID NO:28). Proteins of *E. coli* cells co-expressing the above three precursors were analyzed on two Western blots, using antibodies against the His-tag and the thioredoxin, respectively. A spliced protein was clearly observed, indicating that the three precursors had been trans-spliced into one. The spliced protein was identified, based on its recognition by both antibodies and on its expected molecular size. Approximately 50% of the T-precursor remained un-spliced, but this could be attributed to a lower level of expression and/or stability of the H-precursor that is a very short (24-aa) polypeptide.

The scheme of internal protein splicing of FIG. 2 was also demonstrated in vitro, using the Ssp GyrB S11 split intein and the Rma DnaB S1 split intein. The M-precursor and the T-precursor were same as described above, except that they were separately expressed and purified. A small synthetic peptide was made to contain the same intein sequences as the H-precursor above, but the His-tag sequence of the H-precursor was replaced by a sequence containing the Flag-tag (F). This 30-aa F peptide had the sequence GVFVHNSADYKD-DDDKSGCLAGDTLITLAS [SEQ ID NO:73], with the first 6 aa being the C-intein of the Ssp GyrB S11 split intein, the last 12 aa being the N-intein of the Rma DnaB S1 split intein, and the underlined sequence being the Flag-tag. As illustrated in FIG. 6A, the internal peptide splicing was carried out in vitro in a two-step process. The splicing products were analyzed through SDS-PAGE and Western blot using an anti-F antibody (FIG. 6B). The final spliced protein (M-F-T) was clearly observed and identified by its expected molecular size and recognition by the anti-F antibody. Other expected splicing intermediates and products were also observed, which further confirmed the two-step trans-splicing process. The M-precursor was almost completely converted into the spliced protein, although an excessive amount of the T-precursor remained. Overall, the step 1 splicing efficiency was estimated to be over 90%, while the step 2 splicing efficiency was estimated to be ~70% under the conditions used.

Figure 7:
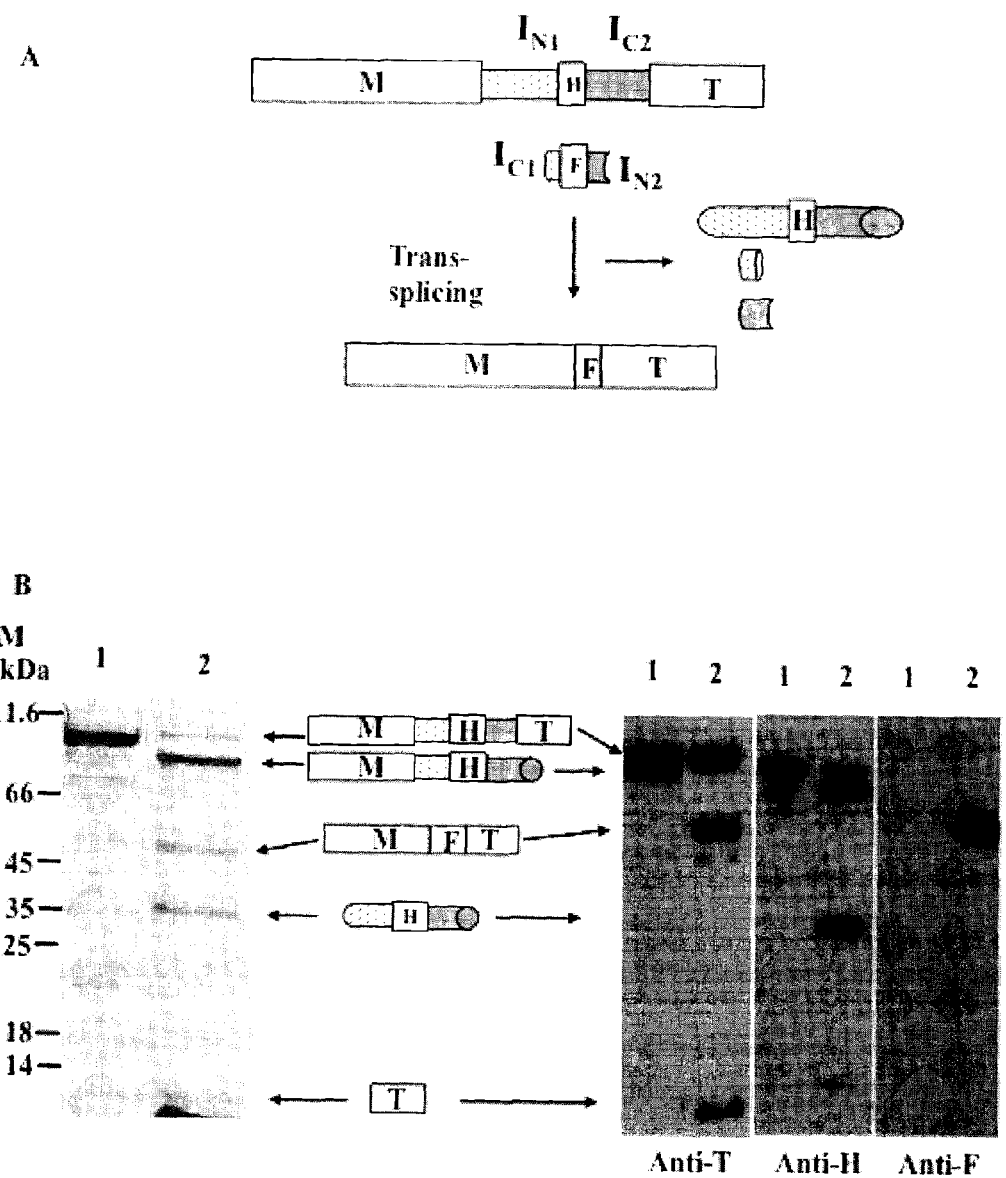
FIG. 7 is a demonstration of internal peptide splicing into a single precursor protein. A, schematic illustration of the trans-splicing reactions. All symbols are same as in FIGS. 5 and 6, except that a single precursor protein (M-$I_{N1}$-H-$I_{C2}$-T) was expressed and purified. B, observation of the trans-spliced protein (M-F-T) and other products, through SDS-PAGE followed by Coomassie blue stain (left panel) or Western blots using antibodies against the thioredoxin (anti-T), the His-tag (anti-H), and the FLAG-tag (anti-F). Lanes 1 and 2 show the partially purified precursor protein before and after the splicing reactions, respectively.

An alternative scheme of the above internal peptide splicing was demonstrated in vitro. As illustrated in FIG. 7A, this scheme used a single precursor protein ($M-I_{N1}-H-I_{C2}-T$), which was essentially the above M-precursor and T-precursor linked by a His-tag sequence (SEQ ID NO:30). This single precursor protein was reacted with the same F peptide as described above. The expected trans-spliced protein (M-F-T) and other products were clearly observed, through SDS-PAGE followed by Coomassie blue stain and Western blots using antibodies against the T, H, and F sequences (FIG. 7B).

Figure 8:
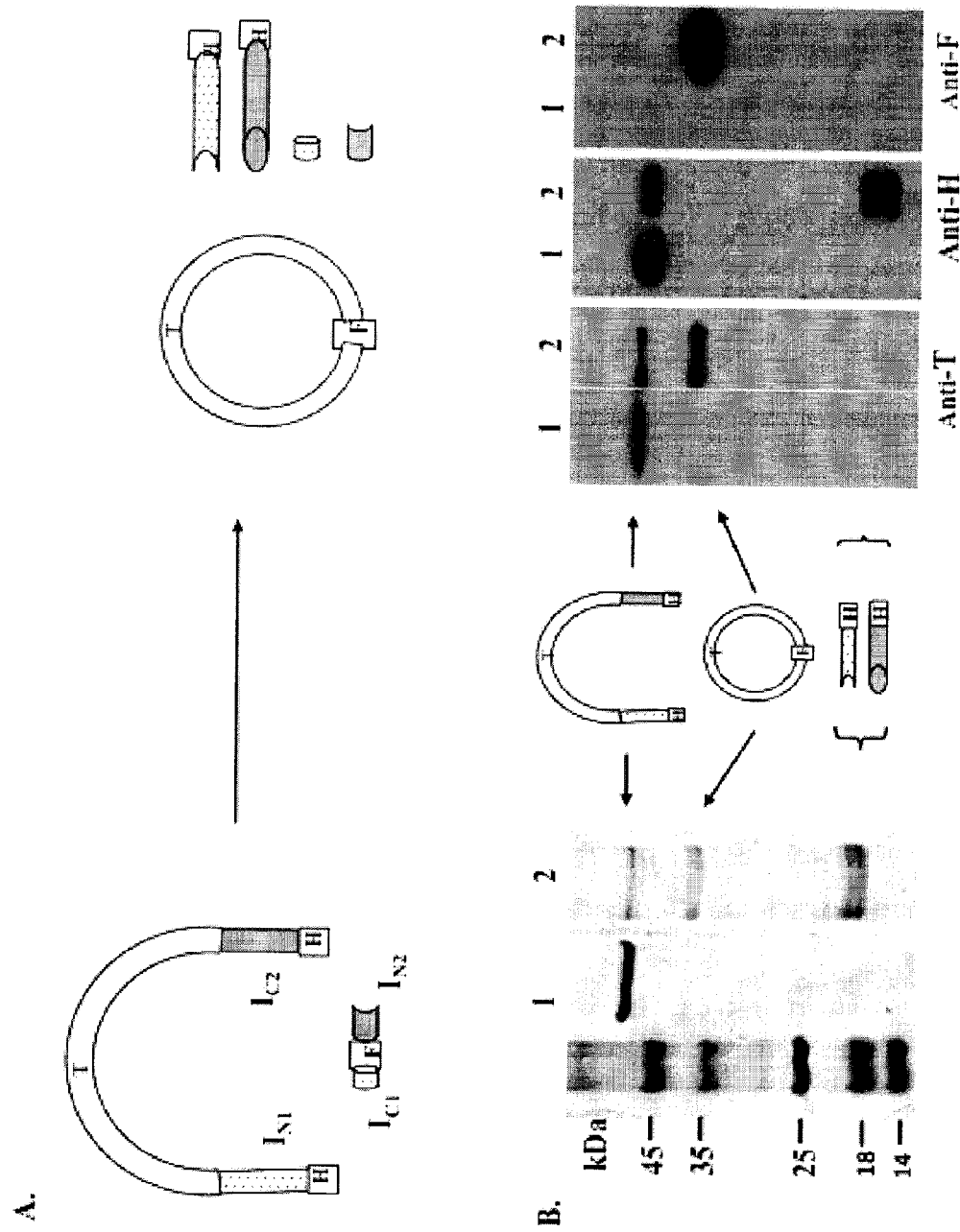
FIG. 8 is a demonstration of controllable protein cyclization in vitro. A, schematic illustration of the protein cyclization through trans-splicing reactions. All symbols are same as in FIGS. 5 and 6, except that a single precursor protein (H-$I_{C2}$-T-$I_{N1}$-H) was expressed and purified. B, observation of the cyclized protein (circular T-F) and other products, through SDS-PAGE followed by staining with Coomassie blue (left panel) or Western blots using antibodies against the thioredoxin (anti-T), the His-tag (anti-H), and the FLAG-tag (anti-F). Lanes 1 and 2 show the partially purified precursor protein before and after the splicing reactions, respectively.

The scheme of controllable protein cyclization of FIG. 3 was demonstrated in vitro, using the Ssp GyrB S11 split intein and the Rma DnaB S1 split intein. As illustrated in FIG. 8A, a precursor protein ($H-I_{C2}-T-I_{N1}-H$) was reacted with the same F peptide as described above. The expected cyclized protein (circular T-F) and other products were clearly observed, through SDS-PAGE followed by staining with Coomassie blue and Western blots using antibodies against the T, H, and F sequences (FIG. 8B).

Example 4

Experimental Procedures of Example 3

Plasmids construction—The Rma DnaB S1 split intein and the Ssp GyrB s11 split intein were constructed as in Example 2, which resulted in the pMRT-S1 and the pMSG-S11 plasmids. These two plasmids were combined or modified, using standard recombinant DNA techniques, to produce plasmids expressing precursor proteins used in the internal peptide splicing and in the controllable protein cyclization.

Protein expression, purification, and trans-splicing analysis in E. coli—The IPTG-induced gene expression, SDS-PAGE, and Western blotting were carried out as previously described [42]. Briefly, cells containing individual expression plasmid were grown in liquid Luria broth medium at 37° C. to late log phase ($A_{600}$ 0.5). IPTG was added to a final concentration of 0.8 mM to induce production of the recombinant proteins, and the induction was continued for 3 h. Cells were then harvested and lysed in a gel loading buffer containing SDS and DTT in a boiling water bath. Following electrophoresis in SDS-polyacrylamide gel, Western blotting was carried out with either anti-thioredoxin monoclonal antibody (Invitrogen) or anti-His-tag antibody (Roche), using the Enhanced Chemi-Luminescence detection kit (GE Healthcare). Quantities of protein bands were estimated using a gel documentation system (UVP). When needed, a recombinant protein in the cell lysate was purified by amylose affinity chromatography (amylose resin from New England Biolabs) following manufacturer's instructions. Protein concentration was determined with the Bradford assay (Biorad).

Trans-splicing analysis in vitro—For each trans-splicing reaction, the precursor protein (~20 μM) was incubated with the Flag peptide at a molar ratio of 1:10. The incubation was in trans-splicing buffer (20 mM Tris-HCl, pH 8.0, 150 mM NaCl, 1 mM DTT, 1 mM EDTA) at room temperature for 16 hours. The results were analyzed by doing SDS-PAGE and Western blotting as described above.

Example 5

Protein C-Terminal Labeling Through Trans-Splicing with Labeled Peptides

A method of protein C-terminal labeling was designed according to the scheme of C-terminal peptide splicing of FIG. 2, by using the Ssp GyrB S11 split-intein [44]. A recombinant precursor protein is produced to contain the 150-aa N-intein ($I_N$) sandwiched between a target protein and an affinity binder, where the affinity binder facilitates purification of the precursor protein. A short peptide is chemically synthesized to contain the 6-aa C-intein (Ic) followed by a small linker and the labeling group. The short linker begins with a nucleophilic amino acid residue required for the splicing reaction. When the precursor protein and the synthetic peptide are incubated together, the large N-intein and the small C-intein are expected to recognize one another, associate non-covalently, form an active intein conformation, and catalyze a protein trans-splicing reaction. As a result, the C-terminus of the target protein will be joined through a peptide bond to the small linker followed by the labeling group, with the N-intein (followed by the affinity binder) and the C-intein excised.

Figure 9:
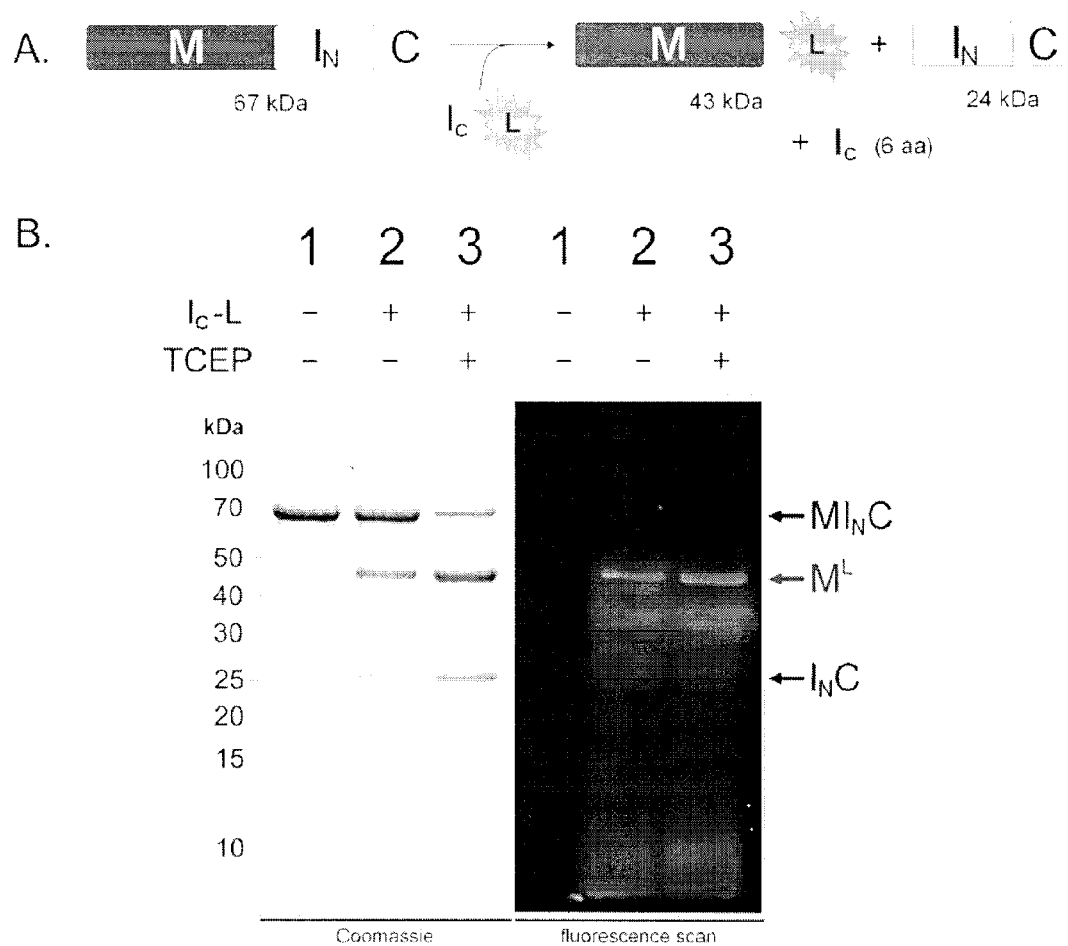
FIG. 9 is a demonstration of protein C-terminal labeling using a SCI split intein (the Ssp GyrB S11 split intein). A. Schematic illustration of the labeling process. The purified recombinant precursor protein (MINC) consisted of a maltose binding protein (M) as a target protein, the $I_N$, and the chitin binding domain (C) as an affinity binder. The synthetic peptide ($I_C$-L) consisted of the 6-aa Ic, the sequence SAGSGK as a small linker sequence, and a 5-carboxyfluorescein as a labeling group (L) that is linked covalently to the lysine side chain of the linker sequence. B. Analysis of the labeling results. The partially purified precursor protein was incubated with or without the $I_C$-L peptide and the reducing chemical TCEP, as indicated. The reaction products were analyzed by SDS-PAGE and visualized by Coomassie staining or by fluorescence scan. Positions of the precursor protein (MI$_N$C), the labeled protein ($M^L$), and the excised N-intein ($I_N$C) are indicated. A protein band at the $M^L$ position in lane 1 is the endogenous *E. coli* maltose binding protein co-purified with the precursor protein.

To demonstrate the above method of C-terminal labeling, a precursor protein was produced through recombinant DNA techniques and gene expression in E. coli. The precursor protein $MI_NC$ contained a maltose binding protein (M) as the target protein, a chitin binding domain (C) as the affinity binder, additional to the N-intein ($I_N$) sequence in the middle (FIG. 9A). The precursor protein was purified using amylose resin, although it could also be purified using chitin beads (see below). A 12-aa synthetic peptide was made to have the following sequence: GVFVHNSAGSGK-L [SEQ ID NO:82], with GVFVHN [SEQ ID NO:63] being the C-intein, SAGSGK [SEQ ID NO:83] being the small linker, and -L being the labeling group fluorophore 5-carboxyfluorescein ($\lambda_{exc}$=492 nm, $\lambda_{em}$=517 nm) linked to the side chain of the lysine (K) residue. This peptide was mixed with the purified precursor protein in a splicing buffer and incubated at room temperature for 16 hours to achieve trans-splicing. Analysis of the reaction products, by SDS-polyacrylamide gel electrophoresis, revealed two new protein bands that corresponded in size to the predicted products of the trans-splicing reaction (FIG. 9B). They were the spliced protein $M^L$ (the target protein with the C-terminal labeling group) and the excised N-intein (the $I_NC$ fragment), while the excised C-intein was too small (6 aa) to be seen on the gel. A significant amount of the precursor protein remained, indicating that the trans-splicing reaction did not go to completion. The splicing efficiency, defined as the percentage of the precursor protein that underwent splicing, was estimated to be ~30%, but increased to ~70% when the reducing agent TCEP was present in the splicing buffer.

The spliced (labeled) protein showed the expected fluorescence in a fluorescence scan (FIG. 9B), while the precursor protein and the excised N-intein did not, all as predicted. Diffuse background fluorescence was also visible in the fluorescence scan, which did not correspond to a labeled protein species because the Coomassie-stained gel showed no protein at the respective positions. The spliced protein was further identified through electron spray ionization mass spectrometry (ESI-MS) analysis, which determined a molecular mass of 43814.0 Da that was in close agreement with the calculated mass of 43830.7 Da. ESI-MS analysis following trypsin digestion revealed a peptide having a molecular mass of 1378.0 Da, which corresponded well with the calculated mass (1378.964 Da) of the expected C-terminal labeled peptide (GTLEGGSAGSGK-L; SEQ ID NO:84). Tandem mass spectrometry (MS/MS) analysis of this peptide confirmed its amino acid sequence, including the C-terminal K-L, whose observed mass of 504.2 Da agreed well with its calculated mass of 505.91 Da.

The spliced (labeled) protein was also distinguished from a possible N-cleavage product. Protein trans-splicing in vitro is sometimes accompanied by N- or C-cleavages as undesirable side reactions, in which the peptide bond at the intein's N- or C-terminus, respectively, is broken without the formation of a new peptide bond as in splicing. For example, when the Ssp DnaB S1 split-intein was used in protein N-terminal labeling, the trans-splicing reaction was accompanied by 20-40% C-cleavage of the precursor protein [19, 23]. In this study of protein C-terminal labeling using the Ssp GyrB 511 split-intein, the spliced (labeled) protein band in FIG. 9B could possibly contain both the splicing product and the N-cleavage product, because these two protein products, whose molecular masses were calculated to be 43830.72 Da and 42984.47 Da, respectively, probably could not be separated from each other by SDS-PAGE. Therefore additional experiments were carried out to determine whether the protein trans-splicing reaction was accompanied by N-cleavage of the precursor protein.

To examine possible existence of the N-cleavage product, protein products of the C-terminal labeling reaction were digested with the site-specific protease Factor Xa to produce a short C-terminal peptide. This peptide from the splicing (C-terminally labeled) product has a molecular mass of 1378 daltons, whereas the peptide from the N-cleavage product has a molecular mass of 532 daltons. This size difference and the highly hydrophobic nature of the fluorescein on the C-terminally labeled peptide should allow for easy separation of the two peptides by reverse phase high-performance liquid chromatography (RP-HPLC). The RP-HPLC analysis revealed a single and strong signal (peak) for the C-terminal labeled peptide corresponding to the splicing product. No obvious signal was observed for the unlabeled peptide corresponding to the N-cleavage product, at a position predicted using a control peptide, indicating that there was no detectable amount of the N-cleavage product. Using a method more sensitive than the above RP-HPLC analysis, Factor Xa-generated peptides were analyzed by liquid chromatography (with conditions different from the above RP-HPLC) followed by tandem mass spectrometry (LC-MS/MS). As shown in FIG. 4C, the liquid chromatography revealed a large peak corresponding to the labeled peptide from splicing, and a tiny peak corresponding to the unlabeled peptide from N-cleavage, with both peptides identified through MS/MS analysis (data not shown). The relative peak areas of the two peptides were measured to be $7.14 \times 10^7$ and $5.75 \times 10^9$, respectively, which were used to estimate the relative amounts of the spliced (labeled) product and the N-cleavage product. Based on this estimation, the labeling (trans-splicing) reaction made up ~98.7% of the total, while the N-cleavage reaction made up the remaining ~1.3%.

The above C-terminal labeling reaction was subjected to a kinetic analysis. The labeling (splicing) efficiency was measured from densitometry analysis on anti-C Western blots and calculated as the percentage of the $I_NC$ fragment (representing the spliced or labeled protein) over the total (the $I_NC$ fragment plus the remaining precursor protein), based the fact the $I_NC$ fragment was produced in equal molar amounts as the labeled protein. The splicing (labeling) efficiency was plotted as a function of time, and a maximum labeling efficiency of ~75% was evident after 24 h. The pseudo first-order reaction rate constant ($k_{obs}$) was determined by fitting the plot to the equation $P=P_o(1-e^{-kt})$, where P is the percentage of the $I_NC$ fragment at time t, $P_o$ is the maximum percentage of the $I_NC$ fragment, and k is the observed rate constant [43]. This fit produced a rate constant ($k_{obs}$) of $(3.8 \pm 0.6) \times 10^{-5}$ s$^{-1}$.

Figure 10:
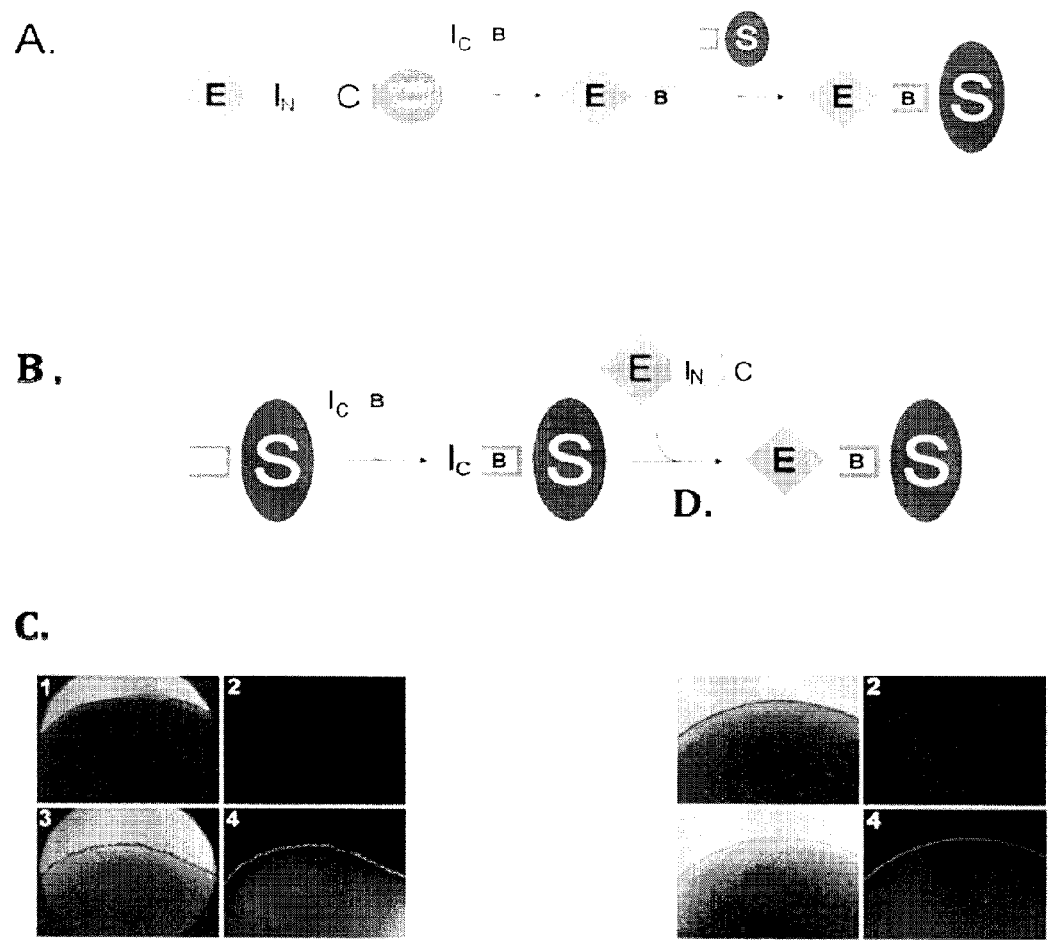
FIG. 10 is a demonstration of protein C-terminal biotinylation using a SCI split intein (the Ssp GyrB S11 split intein). A. Schematic illustration of a biotinylation-purification strategy. The precursor protein (EI$_N$C) consisted of the enhanced green fluorescence protein (E) as a target protein, the IN, and the chitin binding domain (C) as an affinity binder. The precursor protein in a cell lysate is bound to chitin beads. After washing away unbound proteins, the beads are incubated with a synthetic peptide ($I_C$-B) consisting of Ic linked covalently to a biotin (B) through a small linker sequence as in the $I_C$-L peptide of FIG. 9. The resulting biotinylated target protein (EB) is released from the chitin beads and can subsequently bind to streptavidin-coated beads (S). B. Schematic illustration of a biotinylation-fixation strategy. The peptide $I_C$-B is first bound to streptavidin-coated beads. These beads are then incubated with the precursor protein in a cell lysate, and the resulting $E^B$ protein is automatically fixed to the beads, C. Experimental proof of the biotinylation-purification strategy. Streptavidin-coated beads were incubated either with the precursor protein (panels 1 and 2) or with the biotinylated and purified protein $E^B$ (panels 3 and 4). The beads were subsequently observed under microscope either as ordinary light images (panels 1 and 3) or as fluorescence images (panels 2 and 4). D. Experimental proof of the biotinylation-fixation strategy. Streptavidin-coated beads were pre-bound either with (panels 3 and 4) or without (panels 1 and 2) the $I_C$-B peptide. These beads were then incubated with the precursor protein $EI_NC$ in an *E. coli* cell lysate to allow the trans-splicing reaction. After washing away unbound proteins, the beads were observed as above.

The above C-terminal labeling procedure was extended to achieve one-step protein purification and labeling (FIG. 10A). The chitin-binding domain fused to the C-terminal of the N-intein in the $MI_NC$ protein allowed us to explore whether the target protein M could be labeled and purified from an E. coli lysate in a single chromatographic step. To this end, the $MI_NC$ protein in a cell lysate was effectively immobilized on chitin beads, unbound proteins were washed away, and the beads were subsequently incubated with the labeling peptide $I_C$-L. The ensuring trans-splicing reaction produced and simultaneously released the labeled protein ML from the chitin beads, resulting in a one-step labeling-purification. The resulting purified ML protein was able to bind to amylose resin and could subsequently be eluted with maltose-containing buffer (FIG. 10C), showing that the covalent attachment of 5-carboxyfluorescein to the C-terminus of the maltose binding protein did not interfere with the protein's biochemical function.

The C-terminal peptide splicing was also used to achieve protein C-terminal biotinylation (FIG. 10B). To evaluate whether the above method can work with other labeling groups and proteins, we undertook to trans-splice a biotin group onto the C-terminus of an enhanced green fluorescent protein (E). To achieve this site-specific biotinylation, we produced the corresponding precursor protein $EI_NC$ in E. coli and obtained the synthetic peptide $I_C$-B (sequence: GVFVHNSAGSK-B; SEQ ID NO:85; B: biotin linked to side-chain of K). Using the one-step labeling-purification strategy described above, a biotinylated and purified E protein ($E^B$) was successfully generated and could efficiently be immobilized to streptavidin-coated magnet beads (see Figure S2 in the Supporting information). More importantly, the biotinylation was also successful when the precursor protein in a cell lysate was incubated with the $I_C$-B peptide pre-bound to streptavidin-coated beads, demonstrating that the target protein E could be biotinylated and simultaneously fixed to a streptavidin-coated surface (FIG. 10D).

Figure 11:
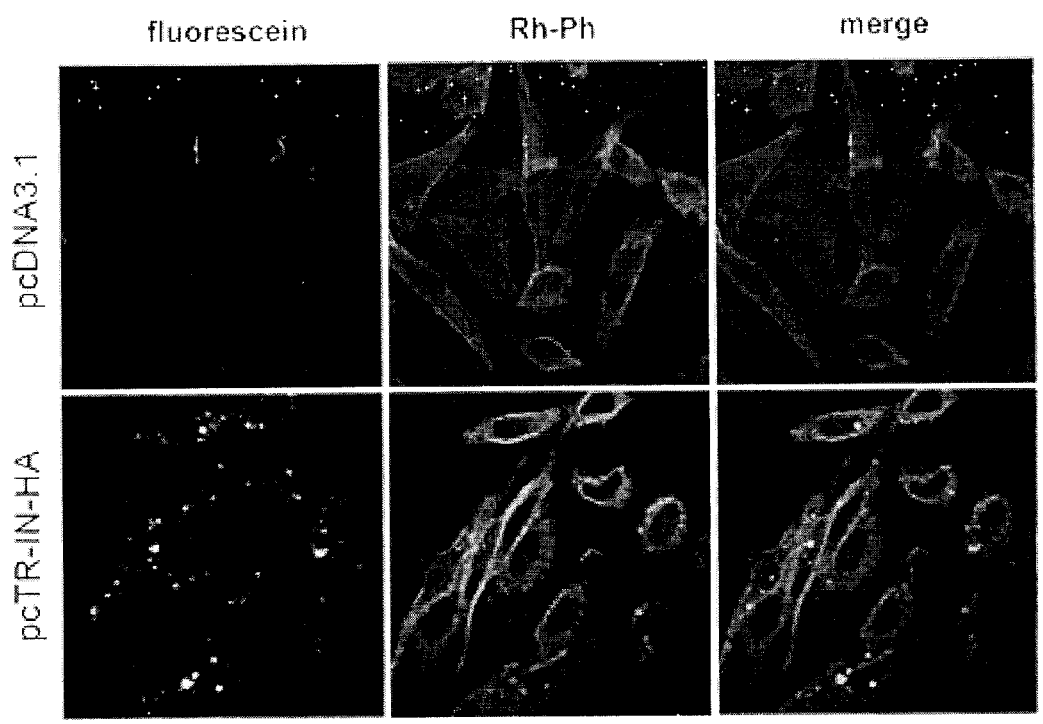
FIG. 11 is a demonstration of receptor protein labeling on live cells. CHO cells were transfected either with an empty plasmid vector (pcDNA3.1) or with a plasmid (pcTR-IN-HA) expressing a transferrin receptor fused to $I_N$, as indicated. The cells were subsequently incubated with the $L_C$-L peptide as in FIG. 9, and excess $L_C$-L peptide was washed away. Representative cells are shown as confocal microscopy images taken with green fluorescence (fluorescein) for the labeled transferring receptor, with red fluorescence (Rh-Ph) for rhodamine-phalloidin-stained actin, or with both (merge), as indicated.

The C-terminal peptide splicing was further used to achieve fluorescence labeling of a membrane receptor protein in the surface of live mammalian cell. The human transferrin receptor was chosen for this test, because this protein is well characterized and known to have its C-terminus located on the outside surface of the cell membrane. Chinese hamster ovary (CHO) cells were transfected with a recombinant plasmid expressing the transferrin receptor fused to $I_N$, treated with the labeling peptide $I_C$-L under gentle conditions, and observed by confocal fluorescence microscopy. Cells expressing the transferrin receptor-$I_N$ fusion protein showed the distinct green fluorescence labeling (FIG. 11), while cells not expressing the fusion protein did not, as expected. The transferrin labeling was seen as discrete spots mostly along the periphery of cells, which may reflect the known phenomenon of transferrin receptor internalization (recycling) through vesicular transport [45, 46].

Example 6

Experimental Procedures of Example 5

Plasmid construction and protein purification—The plasmid $pMI_NC$ was constructed by replacing the Ssp DnaB intein sequence in the pMST plasmid [42] with the coding sequence of the Ssp GyrB S11 $I_N$, and replacement of the thioredoxin sequence with the coding sequence for the chitin binding domain. The plasmid $pTEI_NC$ was constructed by replacing the double-intein ORF of the pTWIN vector (New England Biolabs) with the coding sequences for enhanced green fluorescent protein, followed by the Ssp GyrB S11 In and the chitin binding domain. Plasmid pcTR-IN-HA was constructed by fusing the Ssp GyrB S11 In with a C-terminal HA epitope tag to the coding sequence of the human transferring receptor, and cloning the fusion gene into the mammalian expression vector pcDNA3.1. $MI_NC$ protein expressed in E. coli DH5a cells was purified by amylose affinity chromatography according to the manufacturer's guidelines (New England Biolabs).

In vitro protein labeling—For fluorescent labeling, ~5 ƒM $MI_NC$ protein was incubated with 125 μM peptide $I_C$-L (sequence: GVFVHNSAGSGK-(5-carboxyfluorescein) [SEQ ID NO:82], purchased from New England Peptide) in optimized Splicing Buffer (oSB: 20 mM Tris-HCl, 250 mM NaCl, 1 mM EDTA; pH 8.5) in the presence or absence of 0.1 mM TCEP for 16 h at room temperature.

Reactions were stopped with SDS sample buffer, and samples were run on a 12.5% SDS-PAGE gel in the dark. After completion of electrophoresis, the gel was equilibrated in 10% ethanol/7% acetic acid and scanned for fluorescence using the Typhoon 9410 equipment (Amersham Biosciences) with excitation wavelength of 488 nm and an emission filter for 520 nm. Afterwards, the gel was stained with Coomassie Brilliant Blue and destained using standard procedures. Amylose-binding activity of the fluorescence-labeled maltose binding protein ($M^L$)—Amylose resin (New England Biolabs) was equilibrated with Amylose Column Buffer (ACB: 20 mM Tris-HCl, 200 mM NaCl; pH 7.4) and incubated for 1 h at 4° C. with ML protein. The resin was then extensively washed with ACB (sixty-times resin volume), and a small aliquot was viewed under a fluorescence microscope (AxioVert 200M, Zeiss) with excitation of 489 nm and a filter for emission at 520 nm. Proteins bound to the amylose resin were then eluted with ACB+10 mM maltose, and samples were analyzed by SDS-PAGE, fluorescence scanning and Coomassie-staining as described above.

Simultaneous protein purification and labeling—Precursor proteins $MI_NC$ and $EI_NC$ were expressed in E. coli DH5α and BL21(DE3), respectively, and the cells were lysed in oSB. The soluble fraction of the cell lysate was loaded onto a chitin resin. After washing away unbound proteins with oSB, the resin was incubated in oSB containing 0.1 mM TCEP and either 45 µM $I_C$-L (for $MI_NC$ protein) or 125 µM $I_C$-B (for $EI_NC$ protein), and the incubation was continued overnight at room temperature. Proteins released from the resin were collected and further purified using a small amount of freshly equilibrated chitin resin. The purified protein was then concentrated using Amicon Ultra Centrifugal Filter Devices (Millipore) and analyzed by SDS-PAGE as above.

Mass spectrometry analysis (MS)— MS analysis was performed on (a) $M^L$ protein excised from a Coomassie-stained SDS-polyacrylamide gel and digested with trypsin, (b) a standard in vitro labeling reaction of $MI_NC$ and $I_C$-L without the liquid chromatography (LC) step, and (c) peptide products of a labeling reaction after digestion with Factor Xa. For (a), the $M^L$-containing polyacrylamide gel slice was reduced with DTT, carboxamidomethylated with iodoacetamide and digested with trypsin (Promega, sequencing grade) for 7.5 h at 37° C. Peptides were extracted with 70% acetonitrile, 1% formic acid in HPLC-grade water. The reaction was automated on a ProGest digestion robot (Genomic Solutions). The extraction solvent was removed under vacuum using a speed vac, and tryptic peptides were resuspended in 30 µl of 5% methanol, 0.5% formic acid in HPLC-grade water. For (b), prior to sample injection, salts and excess $I_C$-L peptide were removed from the labeling reaction sample using Zeba Micro Desalt Spin Columns (Pierce). For (c), ~50 µg of a protein labeling reaction were incubated with 1 µg Factor Xa (New England Biolabs) in oSB for 18 h at room temperature. LC-MS/MS was performed using an Ultimate pump and Famos auto-sampler (LC Packings, Amsterdam, Netherlands) interfaced to the nanoflow ESI source of a hybrid triple quadrupole linear ion trap (Qtrap) mass spectrometer (Applied Biosystems, Foster City, Calif., USA). Samples (3 µL) were injected onto a capillary column (0.10×150 mm Chromolith C18, monolithic, Merck) at a flow rate of 1.2 µL/min. A linear gradient was run (5% solvent B to 35% B over 35 min), followed by 90% B for six minutes and re-equilibration at 5% B. Solvent A consisted of 2% acetonitrile, 0.1% formic acid in water, solvent B was 98% acetonitrile, 0.1% formic acid. The sample was sprayed through a distal coated fused silica emitter tip (75 µm ID with 15 µm ID tip, New Objectives Pico Tip). The capillary voltage was 2.10 kV with a declustering potential of 60 V, the curtain gas was set to 15 (arbitrary units). Spectra were acquired using the Information Dependent Acquisition mode.

Kinetic analysis of the labeling reaction—The $MI_NC$ precursor protein was incubated with the $I_C$-L peptide in the presence or absence of TCEP at room temperature for 24 h, during which samples were removed from the reaction at specific time points and the reaction was stopped by addition of SDS sample buffer. Samples were subjected to SDS-PAGE followed by Western blotting analysis using a primary mouse anti-CBD antibody (New England Biolabs) in combination with a secondary rabbit anti-mouse HRP-linked antibody and the Enhanced Chemiluminescence Detection Kit (GE Healthcare). Densitometry analysis of protein signals corresponding to $MI_NC$ and the $I_NC$ fragment was performed with the program ImageJ 1.342. Labeling efficiencies were calculated using the formula $(AI_NC/(AI_NC+AMI_NC))*100$, where $A_X$ represents the densitometry peak area of the respective protein signal. The amount of the $I_NC$ fragment represented that of the spliced (labeled) protein, because these two protein products from the splicing reaction had essentially equal molar amounts (see FIG. 3). Efficiencies were then plotted as a function of time, and pseudo-first order rate constants ($k_{obs}$) were determined as described for trans-splicing of the Ssp DnaE split-intein [2] using the program KaleidaGraph 4.02.

Epifluorescence of biotinylated Enhanced Green Fluorescent Protein ($E^B$)—Streptavidin-coated magnetic beads (Dynal Biotech) were washed three times with PBS-T (10 mM sodium phosphate, 0.9% NaCl, 0.1% Tween-20; pH 7.4) and incubated with either concentrated EB protein (see above) or the soluble fraction from $pTEI_NC$ expression for 1 h at room temperature in the dark. Alternatively, beads were treated with or without 500 µM $I_C$-B peptide for 1 h at room temperature before incubation with the soluble $pTEI_NC$ fraction in the presence of 0.1 mM TCEP for 18 h at room temperature. Unbound proteins were washed away, beads were resuspended in PBS-T and spotted onto a glass slide for fluorescence microscopy as described.

Labeling of transferring receptor on live cells—Chinese hamster ovary cells were cultured in F12 nutrient mixture supplemented with 5% fetal bovine serum, 10 U/mL penicillin and 0.1 mg/mL streptomycin at 37° C. in a humidified chamber with an atmosphere of 5% $CO_2$. Actively growing cells ($1.5 \times 10^5$) were transfected with 0.5 µg plasmid pcTR-IN-HA or empty vector pcDNA3.1 using the MicroPorator MP-100 (Digital Bio) with 10 µL Gold tips and the following settings: 1560 V, 5 ms pulse width, 10 pulses. Cells were seeded in 6-well plates on sterilized cover slips and maintained as above in culture medium without antibiotics. Twenty-four hours post transfection, cells were washed twice with PBS, overlaid with labeling solution (12 µM $I_C$-L peptide, 124 mM NaCl, 3 mM KCl, 5 mM D-glucose, 10 mM HEPES (pH 7.4), 2 mM $CaCl_2$, 1 mM $MgCl_2$, 0.1 mM TCEP) and incubated for 18 h at 23° C./5% $CO_2$. Cells were then prepared for microscopy by fixation with 3.7% formaldehyde in PBS (10 min at room temperature) and permeabilization with 0.05% Triton-X in PBS (9 min at −20° C.). After blocking for 30 min with 3% BSA in PBS (PBS-B), actin was stained with 10 ng/µL it rhodamine-phalloidin (a generous gift from Dr. Paola A. Marignani) in PBS-B for 45 min at room temperature. After washing, cover slips were mounted on SuperFrost Plus microscopic slides (Thermo Scientific) using Mowiol 4-88. Cell imaging was performed on a Laser Scanning Microscope LSM510 (Zeiss) at 100× magnification with excitation wavelengths of 488 nm (Ar laser, for fluorescein fluorescence) and 543 nm (HeNe laser, for rhodamine fluorescence) in combination with filters for emission wavelengths 505-550 nm and 560-615 nm, respectively.

Example 7

Controllable Protein Cleavage Using SCI Split Intein

We developed a system for controllable and site-specific C-cleavage of recombinant protein, which successfully prevented any spontaneous cleavages. As illustrated in FIG. 12A, the In part of a SCI split intein is incorporated within a recombinant precursor protein that also contains a target protein of interest at the N-terminus and an affinity binder (or domain) at the C-terminus for easy purification of the precursor protein. The precursor protein avoids spontaneous cleavage or splicing during its expression and purification, which allows one to initiate a controlled N-cleavage only when needed. The N-cleavage (at the N-terminus of the intein) can be triggered by the addition of Ic in form of a synthetic peptide and/or a nucleophilic compound like dithiothreitol (DTT). As examples of a SCI split intein, the Ssp GyrB S11 split-intein was used initially and successfully (see below), and subsequently other S11 split inteins (see FIG. 1) were also used to achieve similar effects (data not shown).

Using the Ssp GyrB S11 split-intein, we produced a recombinant precursor protein $MI_NC$ in $E.\ coli$, in which M is a maltose binding protein used as a target protein, In is the 150-aa N-intein, and C is a chitin binding domain commonly used for affinity purification. Two Ic peptides were obtained in form of a synthetic peptide, with a longer (8-aa) one having the sequence GVFVHASG [SEQ ID NO:86] and shorter (6-aa) one having the sequence GVFVHN [SEQ ID NO:63]. Theoretically the 6-aa Ic peptide would permit only the first step (N-S acyl shift) of the protein splicing mechanism to occur, whereas the 8-aa Ic peptide would permit the second step (transesterification) to also occur. In the 8-aa Ic peptide, the 6-aa Ic sequence is followed by a nucleophilic residue that is required for the transesterification, and its Asn residue (N) is changed to an Ala residue (A) to prevent the third step (Asn cyclization) of the splicing mechanism, which together permits the N-cleavage but not splicing.

Figure 13:
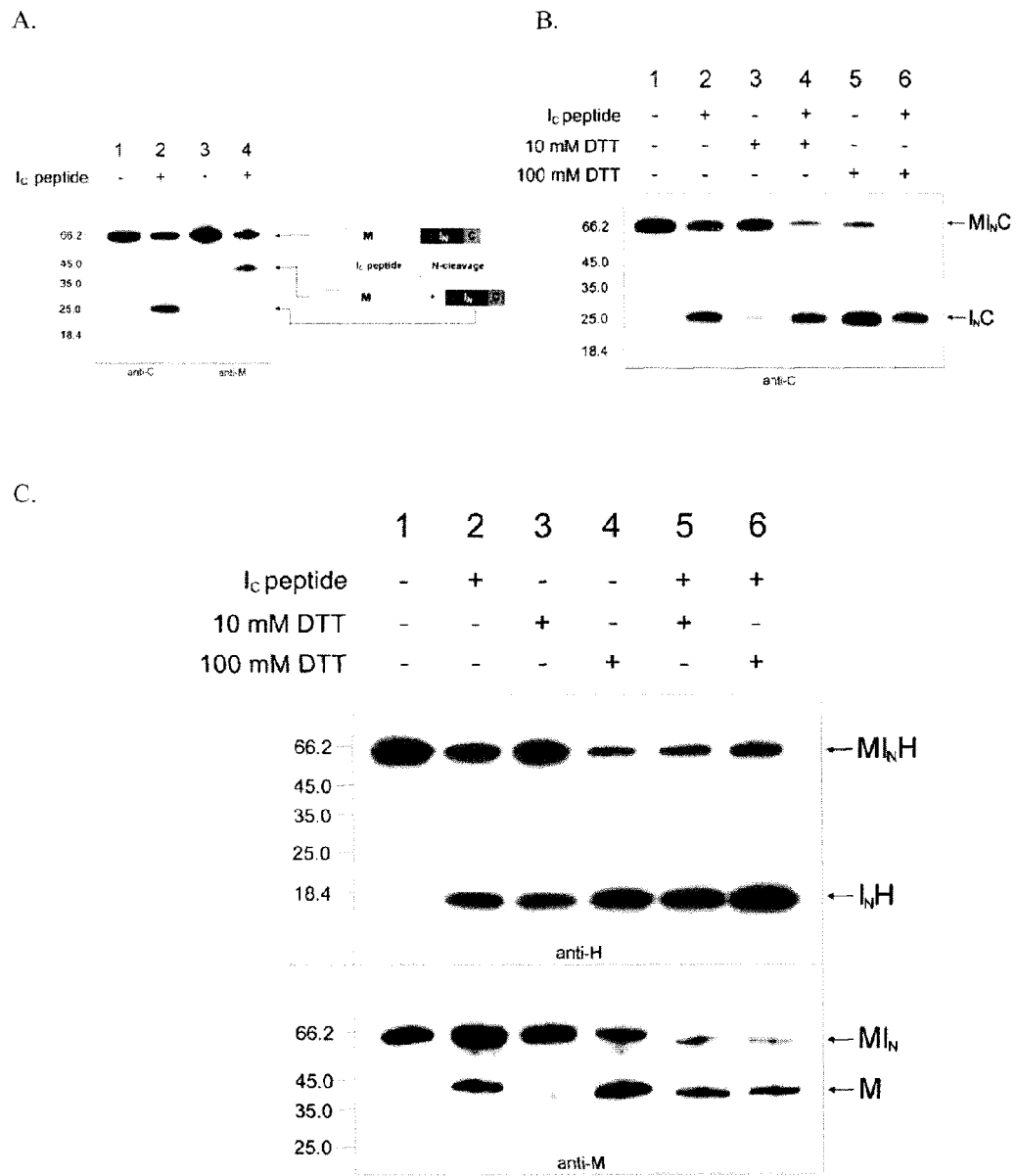
FIG. 13 is a demonstration of controllable N-cleavage using an SCI split intein, namely the Ssp GyrB S11 split intein. In panels A and B, the precursor protein MINC consisted of a maltose binding protein (M) as the target protein, the N-intein ($I_N$), and a chitin binding domain (C) as the affinity binder. In panel C, the precursor protein $MI_NH$ had a His-tag (H) as the affinity binder, while the precursor protein $MI_N$ had no affinity binder. Each purified precursor protein was incubated with (+) or without (−) the Ic peptide (sequence: GVFVHASG) and DTT as indicated to initiate the N-cleavage reaction. The reaction products were analyzed by SDS-PAGE and visualized by Western blotting using anti-M, anti-C, or anti-H antibodies, as indicated.

The precursor protein MINC was stably expressed in $E.\ coli$, with no detectable cleavage or splicing, and could be purified from the soluble $E.\ coli$ fraction via amylose affinity chromatography. When the purified 66-kDa $MI_NC$ protein was incubated with the 8-aa Ic peptide under room temperature, the expected N-cleavage products appeared as a 41-kDa M fragment and a 25-kDa INC fragment, with a corresponding disappearance of the $MI_NC$ protein (FIG. 13A). These two cleavage products were further identified on Western blots using monoclonal antibodies against the M part and the C part, respectively.

We examined the effect of thiol compounds such as DTT on the above N-cleavage reaction using the split intein, as DTT has been known to induce N-cleavage of contiguous inteins by causing thiolysis of the ester bonds formed by the first one or two steps of the protein splicing mechanism. As shown in FIG. 13B, DTT significantly increased the amount of the N-cleavage of the $MI_NC$ protein in presence of the 8-aa Ic peptide. Another tested nucleophilic compound, hydroxylamine, also enhanced the N-cleavage. Most surprisingly, DTT induced the N-cleavage even in the absence of any Ic peptide. This finding indicated for the first time that the In part within the precursor protein is able to undergo the initial N-S acyl rearrangement in the absence of the Ic part of the intein.

Efficiency of the above N-cleavage reaction was compared under different conditions. The cleavage efficiency, which was defined as the percentage of precursor protein $MI_NC$ that had undertwent the N-cleavage, was determined at different time points over a period of 24 hours. From the resulting efficiency-time plots (FIG. 14), the observed pseudo-first order rate constants $k_{obs}$ were determined and compared. The N-cleavage triggered by the 8-aa Ic peptide alone exhibited a rate constant of $(1.2\pm0.1)\times10^{-4}$ s$^{-1}$, and this rate constant increased by approximately 2 and 10 folds when DTT was also present at a concentration of 10 mM and 100 mM, respectively. N-cleavage triggered by the 6-aa Ic peptide, compared to the longer $I_C$, peptide, was approximately 2 folds slower in presence of either DTT concentrations. The maximum extent of the N-cleavage reached 50% in presence of the 8-aa Ic peptide alone, but it increased to 95-98% when 10 mM or 100 mM DTT was also present. N-cleavage in presence of the 6-aa Ic peptide alone reached ~20%, but it increased to 80-90% when the 6-aa Ic peptide was used in combination with 10 mM or 100 mM DTT. In the absence of any Ic peptide, 10 mM DTT induced 55% N-cleavage of the precursor protein $MI_NC$, and 100 mM DTT induced 95% N-cleavage of the $MI_NC$ protein. The observed rate constant of the N-cleavage was $(2.5\pm0.2)\times10^{-5}$ s$^{-1}$ and $(1.0\pm0.2)\times10^{-4}$ s$^{-1}$ with 10 mM and 100 mM DTT, respectively. The rate constants showed a linear relationship with the DTT concentration.

The above N-cleavages were also worked with two other precursor proteins: the 60-kDa $MI_N$ protein having no C-terminal sequence after In, and the 61-kDa $MI_NH$ protein having a His-tag sequence (6 His residues) following In. As shown in FIG. 13C, both of these new precursor proteins underwent the N-cleavage when incubated with DTT and/or the 8-aa Ic peptide. The extent of the N-cleavage showed only small or insignificant differences between these new precursor proteins and the $MI_NC$ protein, except that the $MI_N$ protein exhibited no apparent cleavage in presence of 10 mM DTT alone.

Figure 15:
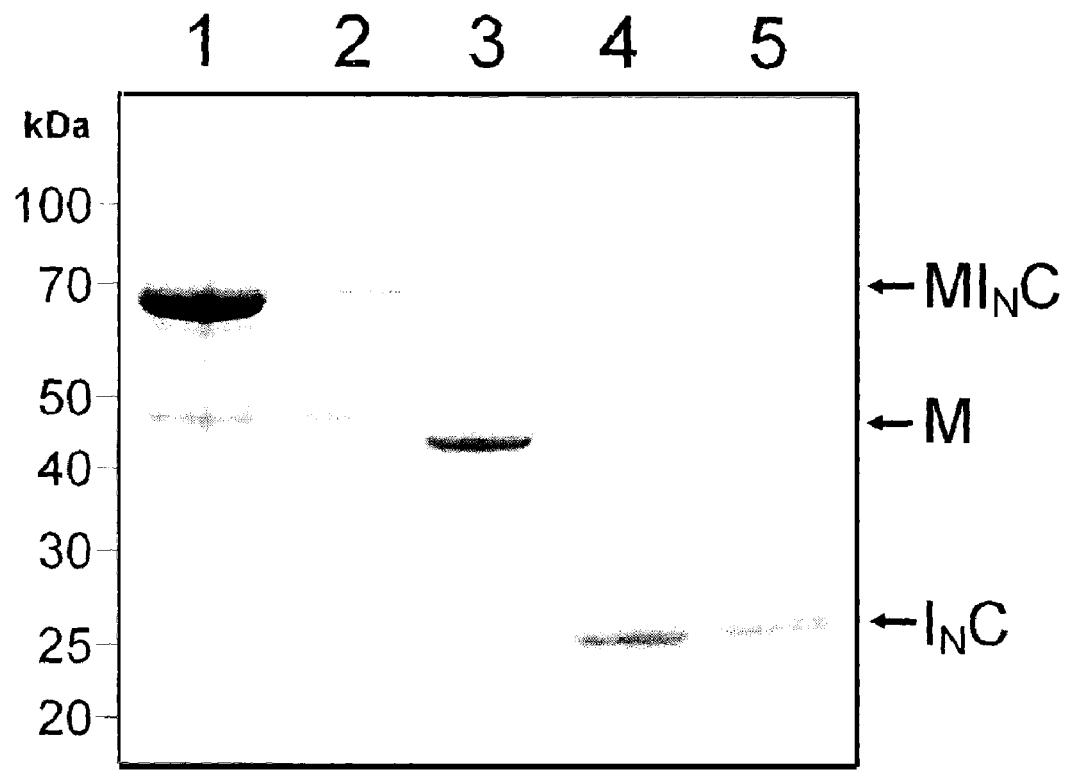
FIG. 15 is a demonstration of the N-cleavage on column for easy purification of the target protein. The precursor protein $MI_NC$ in *E. coli* cell lysate (lane 1) was passed over a chitin column to remove the unbound (flow-through) proteins (lane 2). The column was subsequently treated with the IC peptide plus DTT to allow the N-cleavage (lane 5), the resulting target protein (M) was automatically released from the column in a purified form (lane 3), while the $I_NC$ fragment and any remaining precursor protein remained bound to the column (lane 4).

The N-cleavage reaction can produce the target protein in form of a purified protein, if the reaction is carried out on an affinity column. To demonstrate this, we first incubated the $MI_NC$ protein in an $E.\ coli$ cell lysate with chitin resin, which allowed $MI_NC$ to bind with the resin through its C-terminal chitin binding domain. After washing away unbound proteins, N-cleavage was initiated by incubating the resin with a buffer containing the 8-aa Ic peptide and 50 mM DTT, and the incubation was continued for 4 hours at room temperature. Proteins released from the resin by the N-cleavage were collected in the supernatant, passed through fresh chitin resin to remove any $MI_NC$ and $I_NC$ proteins that might have fallen off the original resin during the prolonged incubation, and concentrated before analysis by SDS-PAGE (FIG. 15). Staining with Coomassie blue showed efficient N-cleavage of the $MI_NC$ protein on the chitin resin, which also resulted in an effective purification of the target protein (M: maltose binding protein).

Figure 16:
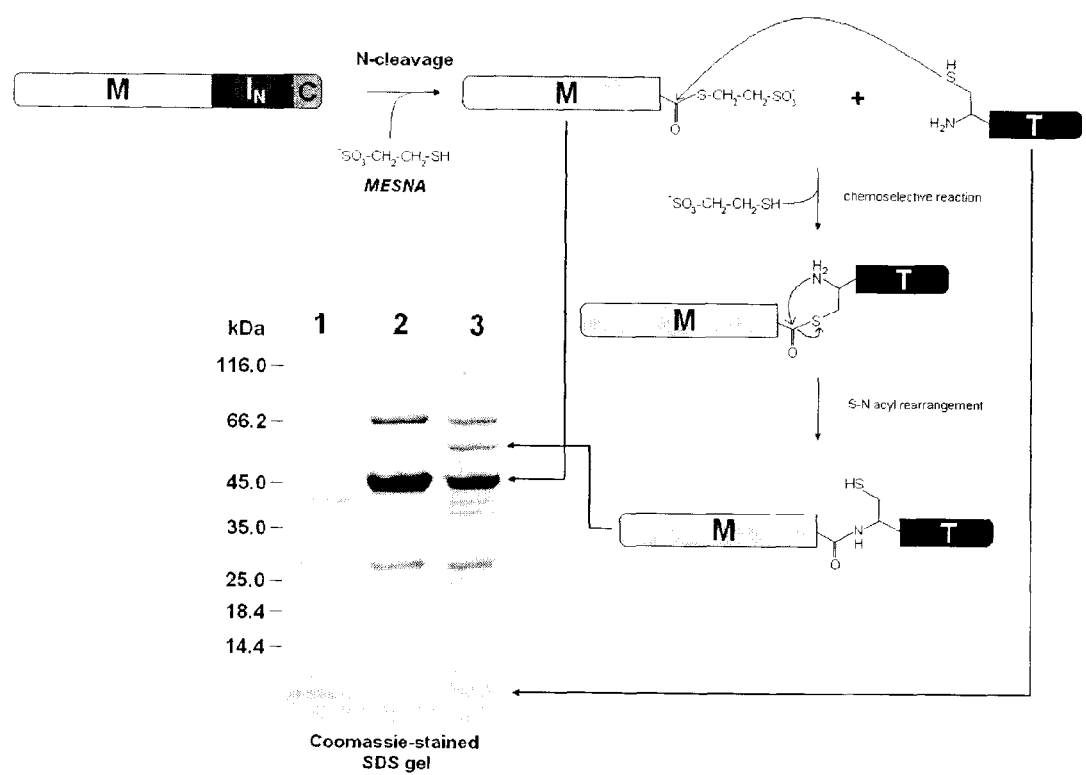
FIG. 16 is a demonstration of the N-cleavage for expressing protein ligation. As illustrated, the N-cleavage of the precursor protein $MI_NC$ was carried out in presence of the thiol compound MESNA, which produced the target protein (M) having a reactive thioester at its C-terminus. This target protein was subsequently reacted with a thioredoxin protein (T) having an N-terminal cysteine residue, which resulted in the ligation of M and T. In the gel picture, lane 1 shows the partially purified thioredoxin having an N-terminal cysteine, lane 2 shows the N-cleavage products including M with its C-terminal thioester, and lane 3 shows reaction products after samples of lane 1 and lane 2 were reacted to produce the ligation product MT.

Another important use of the N-cleavage is in expressed protein ligation, if the N-cleavage is used to generate an activated thioester on the C-terminus of the protein of interest. To demonstrate this, DTT was replaced with the thiol compound MESNA commonly used for generating highly reactive thioesters. As illustrated in FIG. 16, N-cleavage of the $MI_NC$ protein in presence of MESNA would produce the protein M containing the C-terminal thioester, which could then react with the sulhydryl group of a cysteine residue on the N-terminus of another protein (T) in a chemoselective reaction, leading to the formation of a peptide bond between the two proteins M and T. To observe this process, the $MI_NC$ protein in an $E.\ coli$ lysate was bound to chitin beads via its chitin binding domain, unbound proteins were washed away, and the beads were incubated in a buffer containing 50 mM MESNA for 16 hours to allow the N-cleavage. The resulting thioester-tagged M protein (M*) released from the beads was collected, concentrated, and then incubated with a partially purified thioredoxin protein having an N-terminal cysteine residue ($^{Cys}$T). SDS-PAGE analysis revealed the expected products of the N-cleavage as well as the expressed protein ligation. The ligation product (MT) was identified on Western blots using anti-M and anti-T antibodies, in addition to its expected size of 55 kDa.

The precursor protein MI$_N$C could also be induced to undergo the N-cleavage in vivo inside live E. coli cells, when DTT was added to the growth medium in the absence of any Ic peptide. Further deletion of the In sequence by either 8 or 38 aa from its C-terminus abolished the N-cleavage. In vitro experiments also showed that the N-cleavage reaction could be inhibited by zinc ion, and the inhibition could be reversed by EDTA.

Example 8

Experimental Procedures of Example 7

Plasmid construction—The pMI$_N$H plasmid, which encodes the MI$_N$H precursor protein, was same as before [44]. Plasmids pMI$_N$H and pMI$_N$ were constructed by replacing the 639-bp XhoI-HindIII fragment in pMI$_N$C with a 478-bp XhoI-HindIII fragment produced by PCR product (Ssp GyrB S11 In with C-terminal His$_6$-tag (MI$_N$H protein), amplified with primers 5'-GGG CTC GAG GGC GGT TGT TTT TCT GGA GAT AC-3' [SEQ ID NO:87] and 5'-GGG MG CTT CAA TGG TGG TGA TGG TGA TGG CTT GC-3' [SEQ ID NO:88]) or a 461 bp XhoI/HindIII-digested PCR product (Ssp GyrB S11 In without additional C-terminal amino acids (MI$_N$ protein), amplified with primers 5'-GGG CTC GAG GGC GGT TGT TTT TCT GGA GAT AC-3' [SEQ ID NO:89] and 5'-GGG AAG CTT TCA TGA TGC CAA AGC AAA ATT GTG G-3' [SEQ ID NO:90]).

To further delete the In sequence by either 8 or 38 aa from its C-terminus, PCR was performed with primers 5'-CTC GAG GGC GGT TGT TTT TCT GGA GAT ACA TTA GTC GC-3' [SEQ ID NO:76] and 5'-GGG ACC GGT ATG ACC AGA ATC TTC CGT AGT CG-3' [SEQ ID NO: 91] (MI$_N$C$^{142}$) or 5'-GGG ACC GGT GTG GGG AAC CTC MT ATC ATA MC-3' [SEQ ID NO:92] (MI$_N$C$^{112}$), and products were cloned into the pJET1 cloning vector, resulting in plasmids pJI$_N$$^{112}$ and pJI$_N$$^{142}$. Plasmids were then digested with XhoI and AgeI, and the 344 bp- and 434 bp-products (from pJI$_N$$^{112}$ and pJI$_N$$^{142}$, respectively) were cloned into similarly digested pMI$_N$C, yielding plasmids pMI$_N$C$^{112}$ and pMI$_N$C$^{142}$.

Expression and purification of precursor proteins—Precursor fusion proteins were purified using amylose affinity chromatography essentially as described in Example 6. Purity of the elution fractions was assessed by SDS-PAGE, and protein concentrations were determined with the Bradford assay (Biorad). For in vitro N-cleavage studies, the second elution fraction containing the precursor protein could be used without the need for further concentration of the proteins.

In vitro N-cleavage studies—Standard cleavage reactions were performed at RT in optimized Splicing Buffer (oSB: 20 mM Tris-HCl, 250 mM NaCl, 1 mM EDTA; pH 8.5) and contained ~5 µM precursor protein. Reactions were individually supplemented with either Ic peptide ($c_{final}$=500 µM, purchased from EZ Biolabs; sequence: GVFVHASG; SEQ ID NO:86) or DTT ($c_{final}$=10 mM, 100 mM) or both, and reactions were stopped by addition of 3× reducing SDS sample buffer. Samples were analyzed after boiling for 5 min by SDS-PAGE on 12.5% NEXT gels (Mandel Scientific) and Western blotting using mouse anti-CBD antibody (New England Biolabs) in combination with a secondary anti-mouse HRP-linked antibody (GE Healthcare) and the Enhanced Chemiluminescence detection kit (GE Healthcare). Chemiluminescence was visualized on x-ray films.

Kinetic analysis of N-cleavage reaction—The MI$_N$C precursor protein was incubated under various conditions, aliquots were removed from reactions at specific time points and cleavage was stopped by addition of 3× reducing SDS sample buffer followed by storage of the sample at −20° C. SDS-PAGE and Western blotting was performed as described above. Densitometry analysis of protein signals corresponding to MI$_N$C and the I$_N$C fragment was performed with the program ImageJ 1.342. Cleavage efficiencies were calculated using the formula (AI$_N$C/(AI$_N$C+AMI$_N$C))*100, where A$_X$ represents the densitometry peak area of the respective protein signal. Efficiencies were plotted as a function of time, and pseudo-first order rate constants ($k_{obs}$) were determined as described for N-cleavage of the Ssp DnaE split-intein [43] using the program KaleidaGraph 4.02.

Protein purification using the Ssp GyrB S11 split-intein—Expression of soluble MI$_N$C precursor was carried out as described above using buffer oSB. Chitin resin (500 µL, resin #1) was equilibrated with 5 mL oSB, and 400 µL of the soluble E. coli fraction was loaded onto the resin. Unbound proteins were removed by washing the resin with 10 mL oSB. The resin was then soaked in oSB containing 100 mM DTT and 175 mM Ic peptide, and incubated for 4 h at RT. Proteins were eluted from the resin with 4.5 mL oSB. This primary eluate was passed over a freshly equilibrated chitin resin (125 µL, resin #2) three times, and the secondary eluate was concentrated as described above. Samples of both resins and the secondary eluate were analyzed by SDS-PAGE and Coomassie staining. The protein concentration of the secondary eluate was determined with the Bradford Assay (Biorad).

Using the N-cleavage in expressed protein ligation—To prepare MBP with a C-terminal thioester tag (M*) MI$_N$C precursor protein was expressed in E. coli DH5α as described. Harvested cells were resuspended in 2.5 mL oSB, lysed by French Press and cell debris was removed by centrifugation. The supernatant was loaded onto a 1 mL-chitin resin (New England Biolabs) and unbound proteins were washed away with 16 mL oSB. The resin was then soaked with 5 mL oSB containing 50 mM MESNA and incubated at 4° C. over night. Elution was performed with 2 mL oSB, and proteins were concentrated by centrifugation (4,000 rpm, 45 min, 4° C.) using Amicon Ultra Centrifugal Filter Devices (Millipore). Preparation of thioredoxin carrying an N-terminal cysteine residue (CYST) is described elsewhere. Approximately equal amounts of M* was mixed with $^{Cys}$T (both ~40 µM) and incubated for 42 h at 14° C., after which 3×SDS sample buffer was added, and reactions were analyzed by SDS-PAGE and Coomassie staining.

In vivo N-cleavage assay—E. coli cells harboring plasmid pMI$_N$C was grown in LB medium supplemented with 100 µg/mL ampicillin to an OD of 0.6, and expression of precursor proteins was induced with IPTG ($C_{final}$=0.8 mM) for 3 h at 37° C. Cells were then harvested by centrifugation (8,000 g, 3 min, RT), and pellets were washed twice with LB medium lacking IPTG. Cells were resuspended in fresh LB medium with or without addition of DTT ($C_{final}$=100 mM). After incubation over night at RT, cells were harvested, lysed in 1× reducing SDS sample buffer, and total cellular proteins were analyzed by SDS-PAGE and Western blotting using anti-CBD antibody (see above).

Zinc ion inhibition—$MI_NC$ precursor protein was incubated in oSB under various conditions (2 mM $ZnCl_2$, 500 µM Ic peptide, DTT (10 mM or 100 mM), HA (25 mM or 250 mM) and combinations thereof) for 2 h at RT. Reactions containing $Zn^{2+}$ were then supplemented with either 10 mM EDTA or $H_2O$, and incubated for an additional 2 h. Reactions were stopped with 3× reducing SDS sample buffer and analyzed by SDS-PAGE and Western blotting as described.

Example 9

Demonstration of Controllable Protein Cleavages Using SNI Split Intein

We developed a system for controllable and site-specific C-cleavage of recombinant protein, which successfully prevented any spontaneous cleavages. As illustrated in FIG. 12B, the Ic part of a SNI split intein is incorporated within a recombinant precursor protein that also contains a target protein of interest at the C-terminus and an affinity binder (or domain) at the N-terminus for easy purification of the precursor protein. The precursor protein is incapable of spontaneous cleavage or splicing during its expression and purification, which allows one to initiate a controlled C-cleavage only when needed. The C-cleavage (through Asn cyclization at the C-terminus of the intein) can be triggered by the addition of In in form of a synthetic peptide with or without a nucleophilic compound like dithiothreitol (DTT). As examples of a SNI split intein, the Ssp DnaB S1 split-intein was used initially and successfully (see below), and subsequently other S1 split inteins (see FIG. 1) were also used to achieve similar effects (data not shown).

Using the Ssp DnaB S1 split-intein, we produced a recombinant precursor protein $MI_CT$ in *E. coli*, in which T represents a chitin-binding domain fused to thioredoxin used as a target protein, Ic is the 144-aa C-intein, and M is a maltose binding protein commonly used for affinity purification. An 11-aa In (sequence: CISGDSLISLA [SEQ ID NO:93]) was obtained as a synthetic peptide to activate the C-cleavage, which converts the precursor protein $MI_CT$ into an N-terminal fragment $MI_C$ and a C-terminal fragment T, as illustrated in the top part of FIG. 17. The precursor protein and its cleavage products could easily be identified through SDS-PAGE and Western blotting, based on each protein's predicted size and specific recognition by anti-M and anti-T antibodies.

Figure 17:
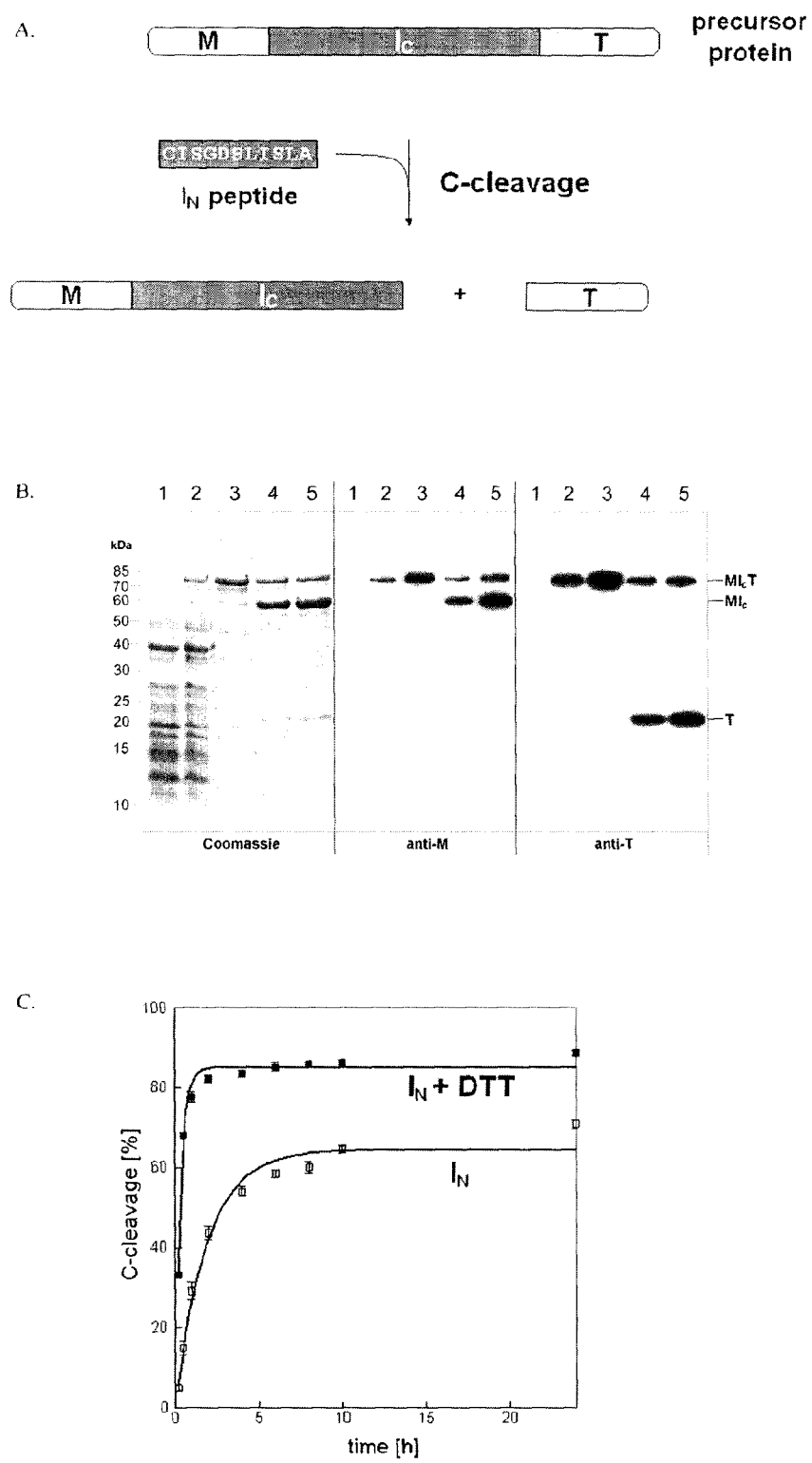
FIG. 17 is a demonstration of controllable C-cleavage using a SNI split intein, namely the Ssp DnaB S1 split intein. A. Schematic illustration of the C-cleavage. The recombinant precursor protein ($MI_CT$) consisted of a thioredoxin protein (T) as a target protein, the Ic, and a maltose binding protein (M) as affinity binder for easy purification of the precursor protein. The synthetic In peptide is shown with its 11-aa sequence. B. SDS-PAGE analysis of the C-cleavage reaction. Protein bands were visualized by Coomassie blue staining or by Western blots using anti-M or anti-T antibodies, as indicated. Lanes 1 and 2 show *E. coli* total proteins before and after expression (induced by IPTG) of the precursor protein, respectively. Lane 3 shows the partially purified precursor protein. The precursor protein was incubated with the In peptide in the absence (lane 4) or presence (lane 5) of DTT. C. Kinetic (time course) analysis of the C-cleavage reaction in presence of In or In plus DTT, as indicated. The C-cleavage was measured as the percentage of precursor protein that had underwent the cleavage. The experiments were performed in triplicate, and error bars represent standard deviations.

As shown in FIG. 17, the precursor protein $MI_CT$ was expressed in *E. coli* cells and partially purified using amylose resin. No spontaneous cleavage or splicing product was detected during the expression and purification of the precursor protein. When the purified precursor protein was incubated with the In peptide, the expected cleavage products ($MI_C$ and T) appeared, showing that the In peptide had triggered the expected C-cleavage. Efficiency of the C-cleavage was estimated as the percentage of the precursor protein that had been converted into the cleavage products at the end of the incubation, using the Western blot for measurements. Under the in vitro conditions used, 70% and 88% of the precursor protein underwent the C-cleavage in the absence and presence of the reducing agent DTT, respectively. The rate constant of the In peptide-triggered C-cleavage reaction was determined through kinetic analysis (FIG. 1C). A pseudo-first order reaction was achieved by using ~40 fold molar excess of the In peptide relative to the precursor protein. The C-cleavage reaction was analyzed at different time points over a period of 24 hours by estimating the percentage of precursor protein that had been cleaved. The rate constant ($k_{obs}$) was calculated to be $(1.4\pm0.2)\times10^{-4}$ $s^{-1}$ in the absence of DTT and $(8.3\pm0.05)\times10^{-4}$ $s^{-1}$ in the presence of DTT.

The above C-cleavage method was also modified to produce a protein of interest having a Cys residue at its N-terminus, because an N-terminal Cys is required for certain applications such as expressed protein ligation. A new precursor protein $CI_CT'$ was produced through recombinant DNA and site-directed mutagenesis, in which the affinity-binding domain (C) at the N-terminus was a Chitin Binding Domain, the Ic in the middle was the same as before, and the protein of interest (T') at the C-terminus was a thioredoxin having an N-terminal Cys residue. The precursor protein $CI_CT'$, which was expressed in *E. coli* and partially purified on chitin beads, was treated with the In peptide to trigger the C-cleavage at the C-terminus of Ic (FIG. 2). The expected cleavage products, namely the N-terminal fragment $CI_C$ and the C-terminal fragment T', were clearly observed, based on their predicted sizes in SDS-PAGE. The C-cleavage reaction occurred with the precursor protein still bound to the chitin beads, when incubated with the In peptide overnight at 14° C. in the presence of 50 mM DTT. The identity of the T' protein, which was released from the chitin beads through the C-cleavage, was further confirmed using mass spectrometry (data not shown).

Using the same SNI split intein, we further developed a system for controllable and site-specific N-cleavage of recombinant protein, which also prevented any spontaneous cleavages. As illustrated in FIG. 12C, the small In part of a SNI split intein is incorporated within a recombinant precursor protein that contains a target protein of interest at the N-terminus and an affinity binder (or domain) at the C-terminus for easy purification of the precursor protein. The precursor protein is incapable of spontaneous cleavage or splicing during its expression and purification, which allows one to initiate a controlled N-cleavage by adding the separately produced Ic protein when needed. As examples of a SNI split intein, the Ssp DnaB S1 split-intein was used initially and successfully (see below), and subsequently other S1 split inteins (see FIG. 1) could also be used to achieve similar effects.

Figure 18:
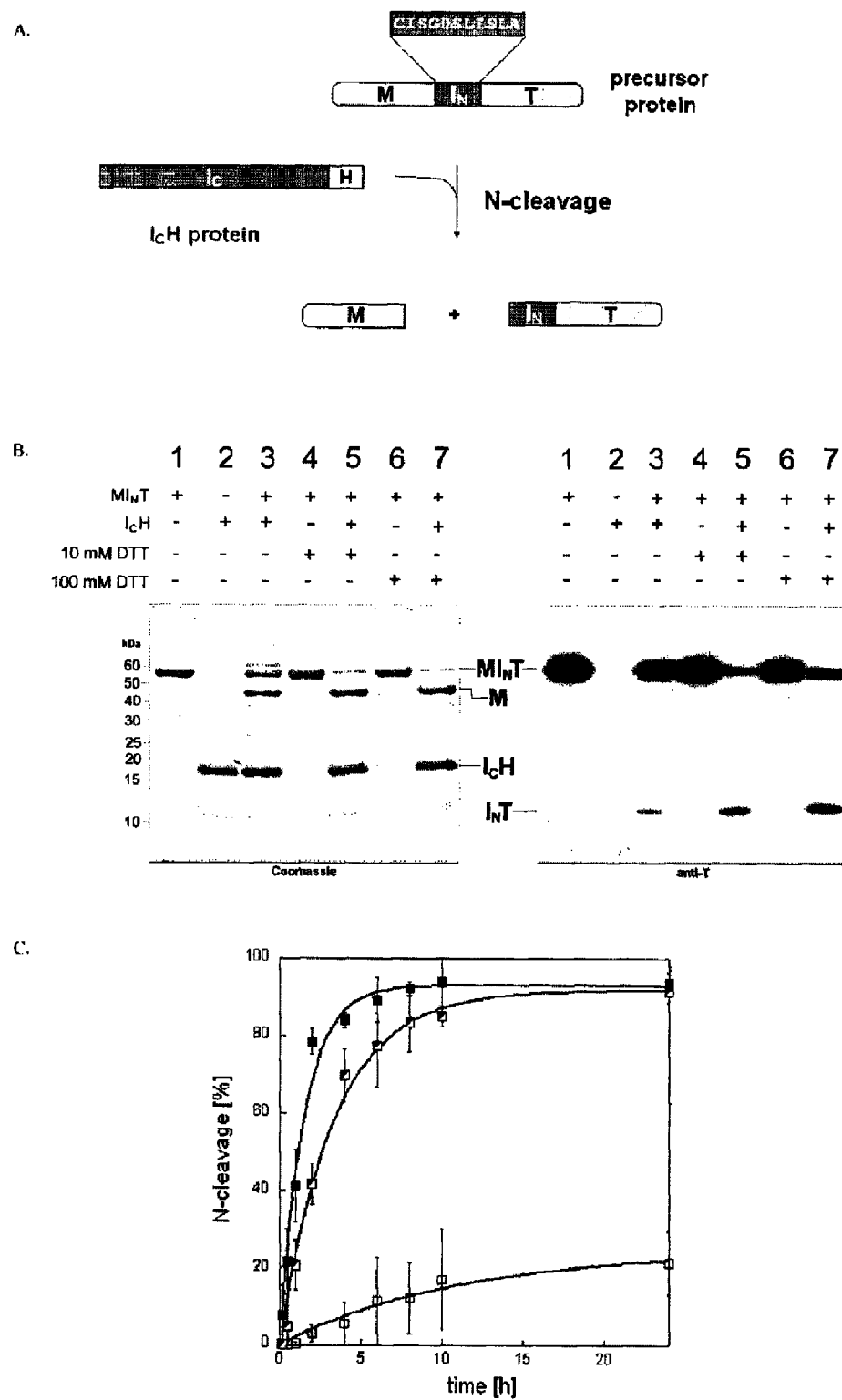
FIG. 18 is a demonstration of controllable N-cleavage using a SNI split intein, namely the Ssp DnaB S1 split intein. A. Schematic illustration of the N-cleavage. The recombinant precursor protein ($MI_NT$) consisted of a maltose binding protein (M) as a target protein, the small In with its 11-aa sequence shown, and a thioredoxin protein (T) in place of an affinity binder. The $I_CH$ protein consisted of the Ic followed by a His-tag for affinity purification, and the Asn residue at the C-terminus of Ic was changed to Ala to prevent splicing. B. SDS-PAGE analysis of the N-cleavage reaction. Protein bands were visualized by Coomassie blue staining or by Western blot using an anti-T antibody, as indicated. Lanes 1 and 2 show the partially purified precursor protein and ICH protein, respectively. Lanes 3 to 7 show the N-cleavage products after the precursor protein was incubated with or without the $I_CH$ protein and DTT, as indicated. C. Kinetic (time course) analysis. The C-cleavage reaction was carried out in presence of ICH (open squares), $I_CH$ plus 10 mM DTT (half-filled squares), or $I_CH$ plus 100 mM DTT (filled squares). The C-cleavage was measured as the percentage of precursor protein that had underwent the cleavage. The experiments were performed in triplicate, and error bars represent standard deviations.

The above controllable N-cleavage was demonstrated using the Ssp DnaB S1 split-intein, as shown in FIG. 18. The 11-aa In sequence was embedded in a precursor protein having a protein of interest (M, maltose binding protein) at the N-terminus and a tag protein (T, thioredoxin) at the C-terminus. This recombinant precursor protein was expressed in *E. coli* and purified using amylose resin. The $I_CH$ protein consisted of the Ic sequence followed by a Ser residue and a His-tag (6 H is residues). The Asn residue at the end of the Ic sequence was changed to Ala to prevent any cleavage or splicing at the C-terminus of Ic. The $I_CH$ protein was expressed in *E. coli* and purified through its His-tag using metal affinity chromatography. No spontaneous cleavage or splicing was detected during the expression and purification of the precursor protein and the $I_CH$ protein.

The purified precursor protein $MI_NT$ and the $I_CH$ protein were mixed in a molar ratio of 1:8, the mixture was incubated at room temperature overnight for N-cleavage to occur, and resulting proteins were analyzed through SDS-PAGE and Western blotting (FIG. 18). The expected cleavage product M was readily identified after staining with Coomassie Blue, based on its predicted size of 42.5 kDa. The other cleavage product, $I_NT$, was not apparent after Coomassie Blue staining, probably due to its smaller predicted size (13.2 kDa), but was clearly identified on Western blots using an anti-T antibody.

Both cleavage products were observed after the precursor protein was treated with the $I_CH$ protein, indicating that the expected N-cleavage had occurred. A higher amount of the N-cleavage was observed when the precursor protein was treated with the $I_CH$ protein in the presence of the reducing agent DTT, although treating the precursor protein with DTT alone did not cause any cleavage. Over 90% of the precursor protein was converted to the cleavage products when an excess amount of the $I_CH$ protein was used together with DTT. Rate constants of the above N-cleavage reactions were determined through kinetic analysis. A pseudo-first order reaction was achieved by using ~25-fold molar excess of the $I_CH$ protein relative to the precursor protein. The percentage of the N-cleavage, measured as the percentage of the precursor protein that had been cleaved, was followed over a period of 24 hours at a series of time points. The rate constant ($k_{obs}$) was calculated to be $(1.9±2.0)×10^{-5}$ s$^{-1}$ when the precursor protein was treated with the $I_CH$ protein alone, $(0.8±0.1)×10^{-4}$ s$^{-1}$ when the precursor protein was treated with the $I_CH$ protein plus 10 mM DTT, and $(2.0±0.5)×10^{-4}$ s$^{-1}$ when the precursor protein was treated with the $I_CH$ protein plus 100 mM DTT.

The success of our N-cleavage design revealed for the first time a structural flexibility of the Ic protein, as the Ic protein could functionally assemble with the 11-aa In sequence even when the In was sandwiched between two large protein domains. The crystal structure of the Ssp DnaB mini-intein, from which the S1 split-intein was derived, is shaped like a disk or closed-horseshoe [28], and the 11-aa In sequence runs almost perpendicularly through the center of the disk-like structure. Spatially it would appear impossible for the In sequence to simply insert or thread itself through the central cavity of the Ic protein, because the In sequence was sandwiched between two relatively large globular proteins (the 42-kDa maltose binding protein and the 12.5-kDa thioredoxin). A more likely scenario is that the Ic protein was structurally flexible enough to open up like a clamp, so that it could saddle onto the In sequence and then close around the In sequence to form the active intein. It is also possible that the Ic protein might preexist as open-clamp structure and could change to the closed-disk-like structure only upon association with the In sequence.

Compared to existing intein-based methods that use contiguous inteins, our methods using the S1 split-intein completely avoided any spontaneous cleavage during expression and purification of the precursor protein. This is a significant advantage, because spontaneous cleavages often result in lower yields of the purified protein and sometimes may not even be tolerated by the producing cell. In previous reports using contiguous inteins, unwanted spontaneous cleavages have been observed in vivo at various levels and could be as high as 90%. In our C-cleavage method, the 11-aa In peptide may not be overly expensive and laborious to use, due to the small size of the peptide. For example, cleavage of 100 mg of a 50 kDa-precursor protein may require as little as 20 mg of the In peptide, if the peptide is used at ~10 fold molar excess over the precursor protein to drive the cleavage reaction. The commercial cost of 20 mg In was estimated to be ~600 US dollars, and this peptide cost may easily be compensated by an increase in protein yield due to the prevention of spontaneous cleavage observed with other intein-based methods. This cost-effectiveness may be particularly true when producing high value proteins for research or pharmaceutical uses, when using more expensive producing cells (e.g. mammalian tissue culture), or when spontaneous cleavages are not tolerated. Costs for the In peptide may further be reduced by avoiding commercial synthesis; the 11-aa peptide is fairly easy to produce on a laboratory-scale peptide synthesizer with costs at about $50 US dollars. Lastly, the small In peptide can be stably stored and easily removed from the cleaved proteins through simple dialysis.

The recombinant precursor proteins in this study had either a maltose binding protein or a chitin-binding domain as the affinity binder for easy purification, but potentially one can use other affinity binders such as the His-tag and the glutathione S-transferase (GST-tag). We showed that the C-cleavage could also occur when the precursor protein was bound to chitin beads and incubated with the In peptide, therefore this C-cleavage method may be used in a single-step purification of recombinant proteins, using a process similar to that of the IMPACT method [37]. In such a process, cell lysate containing the precursor protein is passed through an affinity column, unbound proteins are washed away, the In peptide is added to the column to activate the C-cleavage, and the protein of interest is released (cleaved) from the column in a pure form. The C-cleavage reaction reached 88% efficiency, which is comparable to or higher than C-cleavage efficiencies of previous methods using contiguous inteins. The N-cleavage method in this study also showed a much higher (~95%) cleavage efficiency compared to the previously reported IMPACT method using contiguous intein [37], probably because the shorter In sequence imbedded in the precursor protein was less likely to cause protein misfolding.

Example 10

Experimental Procedures of Example 9

Plasmid construction—To construct plasmid $pMI_CT$ for C-cleavage, the Ic coding sequence of Ssp DnaB intein and the thioredoxin coding sequence were PCR-amplified from the pMST plasmid [23], and these coding sequences were fused into the pMAL-c2X plasmid (New England Biolabs) between Xmn I and Hind III sites. Plasmid $pMI_CCT$ was constructed by PCR-amplification of the Chitin Binding Domain coding sequence from the pTWIN1 plasmid (New England Biolabs) and insertion of this sequence at the unique Age I site of $pMI_C$ T. Plasmid $pMI_NT$ for N-cleavage was constructed by deleting the Ic coding sequence from the pMST-S1 plasmid [42] through inverse PCR. Plasmid $pTI_CH$ was constructed by PCR amplification of the Ic coding sequence (with an Asn154Ala mutation and a C-terminal His-tag) and insertion of this sequence in the pTWIN1 plasmid between engineered Nde I and Hind III sites. Plasmid $pTCI_CT'$ was constructed by fusing the coding sequences of the first 20 residues of maltose binding protein, the chitin binding domain, the Ic, and thioredoxin, in this order. The resulting fusion gene was introduced into the pTWIN1 plasmid between engineered Nde I and Hind III sites.

Protein expression and purification—Precursor proteins MU and $MI_NT$ were purified using amylose resin (New England Biolabs) affinity chromatography according to manufacturer's instructions. Briefly, E. coli DH5α cells harboring a specified plasmid were grown in 75 mL Luria Broth (LB) to an OD of 0.6, and 0.8 mM IPTG was added to induce protein expression for 3 h at 37° C. Cells were harvested by centrifugation, resuspended in Amylose Column Buffer (ACB: 20 mM Tris-HCl, pH 7.4, 200 mM NaCl), and lysed by passing through a French Press (14,000 PSI), all at 4° C. After removing cell debris by centrifugation (10,000 rpm, 25 min), the cell lysate was mixed with 1 mL amylose resin (pre-equilibrated with ACB) for 1 h at 4° C. The resin was then poured into a disposable column (Biorad) and washed with 20 mL ACB. The bound protein was eluted with ACB containing 10 mM maltose and collected in 500 μL-fractions. Purity of the eluted protein was assessed by SDS-PAGE and protein concentration was determined using the Bradford assay (Bio-rad). The His-tagged $I_CH$ protein was expressed in *E. coli* BL21(DE3) cells (GeneChoice) as described above, except that protein expression was induced with 0.4 mM IPTG at room temperature for 16-18 hours. Cells were harvested by centrifugation, resuspended in a Binding Buffer (20 mM Tris-HCl, pH 7.9, 500 mM NaCl, 5 mM imidazole), and lysed using French Press (14,000 PSI). After removing cell debris by centrifugation, the soluble fraction was filtered (0.45 μm) and incubated with 1 mL Ni-NTA resin (QIAGEN) for 1 h at 4° C. The resin was poured into a disposable column and washed with 20 mL Binding Buffer, followed by washing with 15 mL Wash Buffer (Binding Buffer plus 60 mM imidazole). Elution was performed with 10 mL Strip Buffer (20 mM Tris-HCl, pH 7.9, 500 mM NaCl, 100 mM EDTA). The eluted protein was dialyzed extensively against optimized Splicing Buffer (oSB: 20 mM Tris-HCl, pH 8.5, 250 mM NaCl, 1 mM EDTA), and proteins were concentrated by centrifugation using Amicon Ultra Centrifugal Filter Devices (Millipore). Assessment of protein purity and concentration was done as above.

In vitro C-cleavage—Standard reactions for In peptide-induced C-cleavage contained ~5 μM $MI_CT$ protein and 200 μM In peptide in Cleavage Buffer (CB: 100 mM Tris-HCl, pH 7.0, 500 mM NaCl), with or without 50 mM DTT, at 37° C. For kinetic analysis, samples were removed at specific time points, and the reaction was stopped by addition of reducing SDS-PAGE sample buffer. Samples were analyzed by SDS-PAGE on a 12.5% NEXT gel (Mandel Scientific) in combination with a conventional 4% Laemmli stacking gel, followed by staining with Coomassie Blue or Western blotting. Amounts of the precursor protein $MI_CT$ and the cleavage fragment $MI_C$ were estimated from the anti-M Western blots through densitometry analysis using ImageJ 1.342. Cleavage efficiencies were defined as the percentage of $MI_C$ over the total ($MI_C$+$MI_CT$). Efficiencies were plotted as a function of time, and rate constants ($k_{obs}$) were determined as described [43] using KaleidaGraph 4.02.

Production of thioredoxin with N-terminal Cys—The $CI_CT$' precursor protein was expressed in liquid culture of *E. coli* strain BL21(DE3)pLysS harboring plasmid $pTCI_CT$', which was induced with 0.8 mM IPTG for 3 h at 37° C. Cells were harvested and lysed in 2 mL CB as above. The soluble cell lysate was added to an equal volume of Chitin resin (New England Biolabs) on a column. After washing with 18 mL CB, a small sample of the resin was taken, and the remaining resin was soaked with a CB solution containing 40 mM In peptide and 50 mM DTT overnight at 14° C. The released proteins were eluted from the resin into 10 mL CB, passed through 500 μL fresh resin, and concentrated as described above.

In vitro N-cleavage—Standard reactions for Ic protein-induced N-cleavage contained ~5 μM $MI_NT$ protein and ~100 μM $I_CH$ protein in oSB, with or without DTT ($c_{final}$=10 or 100 mM), at room temperature. Kinetic analysis was performed as described above by measuring the amount of $MI_NT$ precursor and the $I_NT$ fragment, which were visualized by Western blotting using rabbit anti-T antibody (Sigma) in combination with a secondary mouse anti-rabbit antibody (Sigma) and the Enhanced Chemi-Luminescence detection kit (GE Healthcare).

```
                         SEQUENCES

Sequence M: maltose binding protein [SEQ ID NO: 1], used as model N-extein
MKTEEGKLVIWINGDKGYNGLAEVGKKFEKDTGIKVTVEHPDKLEEKFPQVAATGDGPDIIFWAHDR

FGGYAQSGLLAEITPDKAFQDKLYPFTWDAVRYNGKLIAYPIAVEALSLIYNKDLLPNPPKTWEEIPAL

DKELKAKGKSALMFNLQEPYFTWPLIAADGGYAFKYENGKYDIKDVGVDNAGAKAGLTFLVDLIKNK

HMNADTDYSIAEAAFNKGETAMTINGPWAWSNIDTSKVNYGVTVLPTFKGQPSKPFVGVLSAGINA

ASPNKELAKEFLENYLLTDEGLEAVNKDKPLGAVALKSYEEELAKDPRIAATMENAQKGEIMPNIPQ

MSAFWYAVRTAVINAASGRQTVDEALKDAQTNSSSNNNNNNNNNNNLGIEGRGTLE

Sequence T [SEQ ID NO: 2]: thioredoxin, used as model C-extein
TGMSDKIIHLTDDSFDTDVLKADGAILVDFWAEWCGPCKMIAPILDEIADEYQGKLTVAKLNIDQNPG

TAPKYGIRGIPTLLLFKNGEVAATKVGALSKGQLKEFLDANLA pMSG-Sl1 N-precursor [SEQ ID NO: 1 linked to SEQ ID NO: 3]
(Sequence M)-GGCFSGDTLVALTDGRSVSFEQLVEEEKQGKQNFCYTIRHDGSIGVEKIINARKTK

TNAKVIKVTLDNGESIICTPDHKFMLRDGSYKCAMDLTLDDSLMPLHRKISTTEDSGHMEAVLNYNH

RIVNIEAVSETIDVYDIEVPHTHNFALASHHHHHH pMSG-Sl1 C-precursor [SEQ ID NO: 4 linked to SEQ ID NO: 2]
MGVFVHNSAGE-(Sequence T)

pMSX-Sl1 N-precursor [SEQ ID NO: 1 linked to SEQ ID NO: 5]
(Sequence M)-IDECLTGDSQVLTRNGLMSIDNPQIKGREVLSYNETLQQWEYKKVLRWLDRGEKQ

TLSIKTKNSTVRCTANHLIRTEQGWTRAENITPGMKILSPASGHHHHHHGGSGSPQWHTNFEEVES

VTKGQVEKVYDLEVEDNHNFVAN pMSX-Sl1 C-precursor [SEQ ID NO: 6 linked to SEQ ID NO: 2]
MGLLVHNCH-(Sequence T)
```

SEQUENCES pMTE3-S11 N-precursor [SEQ ID NO: 1 linked to SEQ ID NO: 7]
(Sequence M)-KFAEYCLTYETEIMTVEYGPLPIGKIVEYRIECTVYTVDKNGYIYTQPIAQWHNRGMQ

EVYEYSLEDGTVIRATPEHKFMTEDGQMLPIDEIFERNLDLKCLGTLELEASGHHHHHGGSGSVKI

VSRKLAKTENVYDIGVTKDHNFVLAN pMTE3-S11 C-precursor [SEQ ID NO: 8 linked to SEQ ID NO: 2]
MGLIASNCFNKS-(Sequence T)

pMTX-S11 N-precursor [SEQ ID NO: 1 linked to SEQ ID NO: 9]
(Sequence M)-HRIGCCLSGNTKVRFRYSSSSQEAKYYEETIEKLANLWHYGSKNQYTSKDAKCMQE

NISSRNIFTLDTQTNQIVSSKITNIYINGEKETYTIKTVSGKEIRATLEHQFWTNQGWKRLKDFNNSTQ

LCEVQLASGHHHHHGGSGSGVFVEIESIEKFGKEITYDLEVEHPEHNFIAN pMTX-S11 C-precursor [SEQ ID NO: 10 linked to SEQ ID NO: 2]
MGLVVHNSFDVQ-(Sequence T)

pMSG-S1 N-precursor [SEQ ID NO: 1 linked to SEQ ID NO: 11]
(Sequence M)-GGCFSGDTLVALTD pMSG-S1 C-precursor [SEQ ID NO: 12 linked to SEQ ID NO: 2]
MGRSVSFEQLVEEEKQGKQNFCYTIRHDGSIGVEKIINARKTKTNAKVIKVTLDNGESIICTPDHKFM

LRDGSYKCAMDLTLDDSLMPLHRKISTTEDSGHSHHHHHHSMEAVLNYNHRIVNIEAVSETIDVYDI

EVPHTHNFALASGVFVHNSAGE-(Sequence T)

pMRT-S1 N-precursor [SEQ ID NO: 1 linked to SEQ ID NO: 13]
(Sequence M)-LRESGCLAGDTLITLAS pMRT-S1 C-precursor [SEQ ID NO: 14 linked to SEQ ID NO: 2]
MDGRRVPIRELVSQQNFSVWALNPQTYRLERARVSRAFCTGIKPVYRLTTRLGRSIRATANHRFLT

PQGWKRVDELQPGDYLALPRRIPSHHHHHHPRVLASMAAQSDVYWDPIVSIEPDGVEEVFDLTVP

GPHNFVANDIIAHNSIENIVD-(Sequence T)

pMCP-S1 N-precursor [SEQ ID NO: 1 linked to SEQ ID NO: 15]
(Sequence M)-fwekaCLQNGTRLLR pMCP-S1 C-precursor [SEQ ID NO: 16 linked to SEQ ID NO: 2]
MADGSEVLVEDVQEGDQLLGPDGTSRTASKIVRGEERLYRIKTHEGLEDLVCTHNHILSMYKERSG

SERAHSPSADLSLTDSHERVDVTVDDFVRLPQQEQQKYQLFRSTASGHHHHHGGSGSVRHERP

STSKLDTTLLRINSIELEDEPTKWSGFVVDKDSLYLRHDYLVLHNsgfee-(Sequence T)

pMSX-S1 N-precursor [SEQ ID NO: 1 linked to SEQ ID NO: 17]
(Sequence M)-IDECLTGDSQVLTR pMSX-S1 C-precursor [SEQ ID NO: 18 linked to SEQ ID NO: 2]
MNGLMSIDNPQIKGREVLSYNETLQQWEYKKVLRWLDRGEKQTLSIKTKNSTVRCTANHLIRTEQG

WTRAENITPGMKILSPASGHHHHHGGSGSPQWHTNFEEVESVTKGQVEKVYDLEVEDNHNFVA

NGLLVHNCH-(Sequence T)

pMTE3-S1 N-precursor [SEQ ID NO: 1 linked to SEQ ID NO: 19]
(Sequence M)-KFAEYCLTYETEIMTV pMTE3-S1 C-precursor [SEQ ID NO: 20 linked to SEQ ID NO: 2]
MEYGPLPIGKIVEYRIECTVYTVDKNGYIYTQPIAQWHNRGMQEVYEYSLEDGTVIRATPEHKFMTE

DGQMLPIDEIFERNLDLKCLGTLELEASGHHHHHGGSGSVKIVSRKLAKTENVYDIGVTKDHNFVL

ANGLIASNCFNKS-(Sequence T)

pMTX-S1 N-precursor [SEQ ID NO: 1 linked to SEQ ID NO: 21]
(Sequence M)-HRIGCCLSGNTKVRFRY pMTX-S1 C-precursor [SEQ ID NO: 22 linked to SEQ ID NO: 2]
MSSSSQEAKYYEETIEKLANLWHYGSKNQYTSKDAKCMQENISSRNIFTLDTQTNQIVSSKITNIYIN

GEKETYTIKTVSGKEIRATLEHQFWTNQGWKRLKDFNNSTQLCEVQLASGHHHHHGGSGSGVFV

| SEQUENCES |
|---|

EIESIEKFGKEITYDLEVEHPEHNFIANGLVVHNSFDVQ-(Sequence T)

pMTE3-S2 N-precursor [SEQ ID NO: 1 linked to SEQ ID NO: 23]
(Sequence M)-KFAEYCLTY pMTE3-S2 C-precursor [SEQ ID NO: 24 linked to SEQ ID NO: 2]
METEIMTVEYGPLPIGKIVEYRIECTVYTVDKNGYIYTQPIAQWHNRGMQEVYEYSLEDGTVIRATPE

HKFMTEDGQMLPIDEIFERNLDLKCLGTLELEASGHHHHHHGGSGSVKIVSRKLAKTENVYDIGVTK

DHNFVLANGLIASNCFNKS-(Sequence T)

pMSX M-intein [SEQ ID NO: 25]
MNGLMSIDNPQIKGREVLSYNETLQQWEYKKVLRWLDRGEKQTLSIKTKNSTVRCTANHLIRTEQG

WTRAENITPGMKILSPASGHHHHHGGSGSPQWHTNFEEVESVTKGQVEKVYDLEVEDNHNFVAN pMTX M-intein [SEQ ID NO: 26]
MSSSSQEAKYYEETIEKLANLWHYGSKNQYTSKDAKCMQENISSRNIFTLDTQTNQIVSSKITNIYIN

GEKETYTIKTVSGKEIRATLEHQFWTNQGWKRLKDFNNSTQLCEVQLASGHHHHHHGGSGSGVFV

EIESIEKFGKEITYDLEVEHPEHNFIAN pM3T N-precursor [SEQ ID NO: 1 linked to SEQ ID NO: 27]
(Sequence M)-GGCFSGDTLVALTDGRSVSFEQLVEEEKQGKQNFCYTIRHDGSIGVEKIINARKTKT

NAKVIKVILDNGESIICTPDHKFMLRDGSYKCAMDLTLDDSLMPLHRKISTTEDSGHMEAVLNYNHRI

VNIEAVSETIDVYDIEVPHTHNFALAS pM3T H-peptide [SEQ ID NO: 28]:
MGVFVHNSAGETGHHHHHHLELRESGCLAGDTLITLAS pM3T C-precursor [SEQ ID NO: 29 linked to SEQ ID NO: 2]
MDGRRVPIRELVSQQNFSVWALNPQTYRLERARVSRAFCTGIKPVYRLTTRLGRSIRATANHRFLT

PQGWKRVDELQPGDYLALPRRIPRVLASMAAQSDVYWDPIVSIEPDGVEEVFDLTVPGPHNFVAND

IIAHNSIENIVD-(Sequence T)

pMTF precursor [SEQ ID NO: 1 linked to SEQ ID NO: 30 linked to SEQ ID NO: 2]
(Sequence M)-GGCFSGDTLVALTDGRSVSFEQLVEEEKQGKQNFCYTIRHDGSIGVEKIINARKTKT

NAKVIKVTLDNGESIICTPDHKFMLRDGSYKCAMDLTLDDSLMPLHRKISTTEDSGHMEAVLNYNHRI

VNIEAVSETIDVYDIEVPHTHNFALASGGGSGGGSGGHHHHHGGSGGGSGGSGMDGRRVPIREL

VSQQNFSVWALNPQTYRLERARVSRAFCTGIKPVYRLTTRLGRSIRATANHRFLTPQGWKRVDELQ

PGDYLALPRRIPRVLASMAAQSDVYWDPIVSIEPDGVEEVFDLTVPGPHNFVANDIIAHNSIENIVD- (Sequence T)

pMTE1-S11 N-precursor [SEQ ID NO: 1 linked to SEQ ID NO: 31]
(Sequence M)-TYGVLCLPKGTLIDQPDGSREAIENIKSGEVILTSDGRKVWEAKVAKQWRSGVREIL

KITLSSGTVIYSGKNHRFLTPEGDKFAWELQPQVGRVKNALIYGSASGHHHHHGGSGSQDVRVV

HVVSVEEVGEAECFDLEMEDQSSPYFLAE pMTE1-S11 C-precursor [SEQ ID NO: 32 linked to SEQ ID NO: 2]
MGVVVHNCYQEQ-(Sequence T)

pMTE1-S1 N-precursor [SEQ ID NO: 1 linked to SEQ ID NO: 33]
(Sequence M)-TYGVLCLPKGTLIDQPD pMTE1-S1 C-precursor [SEQ ID NO: 34 linked to SEQ ID NO: 2]
MGSREAIENIKSGEVILTSDGRKVWEAKVAKQWRSGVRE1LKITLSSGTVIYSGKNHRFLTPEGDKFA

WELQPQVGRVKNALIYGSASGHHHHHHGGSGSQDVRVVHVVSVEEVGEAECFDLEMEDQSSPYF

LAEMGVVVHNCYQEQ-(Sequence T)

pMTE2-S11 N-precursor [SEQ ID NO: 1 linked to SEQ ID NO: 35]
(Sequence M)-DLLRRCLSGSTKVIDAATGNLFSLKEIAAQPEYWLSRKVFSLDLKSQQVVQQPITE

| SEQUENCES |
|---|
| IHPNGVRDVWQITTRTNRKVCATDDHLFYTVLGWKPLKDFSVGDRLGLPNKASGHHHHHGGSGS DVFWDEIISIEYIGKEEVFDLTIPETHNFIAN |
| pMTE2-S11 C-precursor [SEQ ID NO: 36 linked to SEQ ID NO: 2] MDFIVHNCMGKK-(Sequence T) |
| pMTE2-S1 N-precursor [SEQ ID NO: 1 linked to SEQ ID NO: 37] (Sequence M)-DLLRRCLSGSTKVIDA |
| pMTE2-S1 C-precursor [SEQ ID NO: 38 linked to SEQ ID NO: 2] ATGNLFSLKEIAAQPEYWLSRKVFSLDLKSQQVVQQPITEIHPNGVRDVWQITTRTNRKVCATDDHL FYTVLGWKPLKDFSVGDRLGLPNKASGHHHHHGGSGSDVFWDEIISIEYIGKEEVFDLTIPETHNFI ANDFIVHNCMGKK-(Sequence T) |
| pMTR1-S11 N-precursor [SEQ ID NO: 1 linked to SEQ ID NO: 39] (Sequence M)-GNIRRCLPEGALVHTASGLVAIEKIRIGDRVLTSQGFYPVTNFFDQGIQSLCRIQTED GYFECTPDHKVAVLQDLYGNYKMIKAKDLQEGDRLIFVPQASGHHHHHGGSGSDATDLIPVKVKK VEMDVREASTYDIEVASIHEFVCQ |
| pMTR1-S11 C-precursor [SEQ ID NO: 40 linked to SEQ ID NO: 2] MGILVSNSAGIR-(Sequence T) |
| pMTR1-S1 N-precursor [SEQ ID NO: 1 linked to SEQ ID NO: 41] (Sequence M)-GNIRRCLPEGALVHTA |
| pMTR1-S1 C-precursor [SEQ ID NO: 42 linked to SEQ ID NO: 2] MSGLVAIEKIRIGDRVLTSQGFYPVINFFDQGIQSLCRIQTEDGYFECTPDHKVAVLQDLYGNYKMIK AKDLQEGDRLIFVPQASGHHHHHGGSGSDATDLIPVKVKKVEMDVREASTYDIEVASIHEFVCQGI LVSNSAGIR-(Sequence T) |
| pMTR2-S11 N-precursor [SEQ ID NO: 1 linked to SEQ ID NO: 43] (Sequence M)-LGLNPCHSGDTLVSTDQGLIAIQDLVGKQFQALVDLRSIGLSGVRLTDAIAFATGVK TTYQVILNNGMQMRCTGDHQHFTSRGWVSTRDLTDDDNIYIQGGASGHHHHHGGSGSKFISKVK KVEEFGEEVVYDLHVPLTNSFIAN |
| pMTR2-S11 C-precursor [SEQ ID NO: 44 linked to SEQ ID NO: 2] MGCLTHNCGEII-(Sequence T) |
| pMTR2-S1 N-precursor [SEQ ID NO: 1 linked to SEQ ID NO: 45] (Sequence M)-LGLNPCHSGDTLVSTDQ |
| pMTR2-S1 C-precursor [SEQ ID NO: 46 linked to SEQ ID NO: 2] MGLIAIQDLVGKQFQALVDLRSIGLSGVRLTDAIAFATGVKTTYQVILNNGMQMRCTGDHQHFTSRG WVSTRDLTDDDNIYIQGGASGHHHHHGGSGSKFISKVKKVEEFGEEVVYDLHVPLTNSFIANGCL THNCGEII-(Sequence T) |
| pMTR4-S11 N-precursor [SEQ ID NO: 1 linked to SEQ ID NO: 47] (Sequence M)-VQPSGCLDKTALRIFNQGLLYADEVVTPGSGETVGLGLTVRNGIGASTAIANQPME LVEIKLANGRKLRMTPNHRMSVKGKWIHACNLKPGMLLDYSIGEASGHHHHHGGSGSPYKIESVN IGAVCDYSYDFAIEGINDNDSWYWQG |
| pMTR4-S11 C-precursor [SEQ ID NO: 48 linked to SEQ ID NO: 2] MALKSHNTKSLLTNASP-(Sequence T) |
| pMTR4-S1 N-precursor [SEQ ID NO: 1 linked to SEQ ID NO: 49] (Sequence M)-VQPSGCLDKTALRIFNQ |
| pMTR4-S1 C-precursor [SEQ ID NO: 50 linked to SEQ ID NO: 2] MGLLYADEVVTPGSGETVGLGLTVRNGIGASTAIANQPMELVEIKLANGRKLRMTPNHRMSVKGKW IHACNLKPGMLLDYSIGEASGHHHHHGGSGSPYKIESVNIGAVCDYSYDFAIEGINDNDSWYWQG ALKSHNTKSLLTNASP-(Sequence T) |
| pMTHE1-S11 N-precursor [SEQ ID NO: 1 linked to SEQ ID NO: 51] |

| SEQUENCES |
|---|
| (Sequence M)-GGCLAEGSLVLDAATGQRVPIEKVRPGMEVFSLGPDYRLYRVPVLEVLESGVREV VRLRTRSGRTLVLTPDHPLLTPEGWKPLCDLPLGTPIAVPAELPVAGHLAPPEDRHMAEGQVLWDP IVAVEPAGKARTFDLRVPPFANFVSE |
| pMTHE1-S11 C-precursor [SEQ ID NO: 52 linked to SEQ ID NO: 2] MDLVVHNSAGE-(Sequence T) |
| pMTHE1-S1 N-precursor [SEQ ID NO: 1 linked to SEQ ID NO: 53] (Sequence M)-GGCLAEGSLVLDA |
| pMTHE1-S1 C-precursor [SEQ ID NO: 54 linked to SEQ ID NO: 2] MATGQRVPIEKVRPGMEVFSLGPDYRLYRVPVLEVLESGVREVVRLRTRSGRTLVLTPDHPLLTPE GWKPLCDLPLGTPIAVPAELPVAGHLAPPEDRHMAEGQVLWDPIVAVEPAGKARTFDLRVPPFANF VSEDLVVHNSAGE-(Sequence T) |
| pMTHE2-S11 N-precursor [SEQ ID NO: 1 linked to SEQ ID NO: 55] (Sequence M)-GGCLPARARVVDWCTGRVVRVGEIVRGEAKGVWVVSLDEARLRLVPRPVVAAFPS GKAQVYALRTATGRVLEATANHPVYTPEGWRPLGTLAPGDYVALPRHLSYRPSLHLEGHEHMAEA EVYWDRVEAVEPLGEEEVFDLTVEGTHTFVAE |
| pMTHE2-S11 C-precursor [SEQ ID NO: 56 linked to SEQ ID NO: 2] MDVIVHNSAGE-(Sequence T) |
| pMTHE2-S1 N-precursor [SEQ ID NO: 1 linked to SEQ ID NO: 57] (Sequence M)-GGCLPARARVVD |
| pMTHE2-S1 C-precursor [SEQ ID NO: 58 linked to SEQ ID NO: 2] MWCTGRVVRVGEIVRGEAKGVWVVSLDEARLRLVPRPVVAAFPSGKAQVYALRTATGRVLEATAN HPVYTPEGWRPLGTLAPGDYVALPRHLSYRPSLHLEGHEHMAEAEVYWDRVEAVEPLGEEEVFDL TVEGTHTFVAEDVIVHNSAGE-(Sequence T) |
| pMTHR-S11 N-precursor [SEQ ID NO: 1 linked to SEQ ID NO: 59] (Sequence M)-GGCLHPDTLVHTDRGTLRLRELVDPFRRGWQPHTLSVATDEGWRPSPEGYNNGV APTLRVVLENGLEVQGTLNHKLKVLREDGTREWVELQDLRPGDWVIWVLDEHTGTPVQLAPLDEH MAEPFPFNEYYVRVASVEPGGEILTLDLSVEGNHTYLAN |
| pMTHR-S11 C-precursor [SEQ ID NO: 60 linked to SEQ ID NO: 2] MGLVSHNSAGE-(Sequence T) |
| pMTHR-S1 N-precursor [SEQ ID NO: 1 linked to SEQ ID NO: 61] (Sequence M)-GGCLHPDTLVHTDR |
| pMTHR-S1 C-precursor [SEQ ID NO: 62 linked to SEQ ID NO: 2] MGTLRLRELVDPFRRGWQPHTLSVATDEGWRPSPEGYNNGVAPTLRVVLENGLEVQGTLNHKLK VLREDGTREWVELQDLRPGDWVIWVLDEHTGTPVQLAPLDEHMAEPFPFNEYYVRVASVEPGGEI LTLDLSVEGNHTYLANGLVSHNSAGE-(Sequence T) |
| SCI from Ssp GyrB GVFVHN (SEQ ID NO: 63) |
| SCI from Ssp DnaX GLLVHN (SEQ ID NO: 64) |
| SCI from Ter DnaE3 GLIASN (SEQ ID NO: 65) |
| SCI from Ter ThyX GLVVHN (SEQ ID NO: 66) |
| SNI from Ssp Gyr B CFSGDTLVALTD (SEQ ID NO: 67) |
| SNI from Rma DnaB CLAGDTLITLA (SEQ ID NO: 68) |
| SNI from Cne Prp8 CLQNGTRLLR (SEQ ID NO: 69) |
| SNI from Ssp DnaX CLTGDSQVLTR (SEQ ID NO: 70) |
| SNI from Ter DnaE3 CLTYETEIMTV (SEQ ID NO: 71) |
| SNI from Ter ThyX CLSGNTKVRFRY (SEQ ID NO: 72) |

-continued

SEQUENCES

Synthetic peptide IcF GVFVHNSADYKDDDDKSGCLAGDTLITLAS [SEQ ID NO: 73]

FLAG epitope DYKDDDDK (SEQ ID NO: 74)

primer 5'- CTC GAG GGC GGT TGT TTT TCT GGA GAT ACA TTA GTC GC- 3'
(SEQ ID NO: 75)

primer 5'-CAT ATG ACC AGA ATC TTC CGT AGT CGA AAT-3' (SEQ ID NO: 76)

primer 5'-CAT ATG GAA GCA GTA TTA AAT TAC AAT CAC AG-3' (SEQ ID NO: 77)

primer 5'-GAC CGG TCT CGC CAG CGC TGT TAT GGA CAA ACA CTC-3' (SEQ ID NO: 78)

spacer DNA 5'-TAA TTA ACT TAT AAG GAG GAA AAA CAT ATG (SEQ ID NO: 79)

primer 5'-CAT CAC CAC CAT CAC CAT TAA TTA ACT TAT AAG GAG GAA AAA CAT ATG-3'
(SEQ ID NO: 80)

primer 5'-CGT TGC CAA AGC AAA ATT GTG-3' (SEQ ID NO: 81)

synthetic peptide GVFVHNSAGSGK (SEQ ID NO: 82)

linker SAGSGK (SEQ ID NO: 83)

peptide GTLEGGSAGSGK (SEQ ID NO: 84)

synthetic peptide GVFVHNSAGSK (SEQ ID NO: 85)

synthetic peptide GVFVHASG (SEQ ID NO: 86)

primer 5'-GGG CTC GAG GGC GGT TGT TTT TCT GGA GAT AC-3' (SEQ ID NO: 87)

primer 5'-GGG AAG CTT CAA TGG TGG TGA TGG TGA TGG CTT GC-3' (SEQ ID NO: 88)

primer 5'-GGG CTC GAG GGC GGT TGT TTT TCT GGA GAT AC-3' (SEQ ID NO: 89)

primer 5'-GGG AAG CTT TCA TGA TGC CAA AGC AAA ATT GTG G-3' (SEQ ID NO: 90)

primer 5'-GGG ACC GGT ATG ACC AGA ATC TTC CGT AGT CG-3' (SEQ ID NO: 91)

primer 5'-GGG ACC GGT GTG GGG AAC CTC AAT ATC ATA AAC-3' (SEQ ID NO: 92)

synthetic peptide CISGDSLISLA (SEQ ID NO: 93)

TABLE 1

| Name of split intein | Name of natural intein [18] | Sequences of precursor proteins/peptides (SEQ ID NO) | Trans-splicing efficiency |
|---|---|---|---|
| Ssp GyrB S11 | Ssp GyrB | pMSG-S11 N-precursor (3) pMSG-S11 C-precursor (4) | >90% |
| Ssp DnaX S11 | Ssp DnaX | pMSX-S11 N-precursor (5) pMSX-S11 C-precursor (6) | >95% |
| Ter DnaE3 S11 | Ter DnaE-3 | pMTE3-S11 N-precursor (7) pMTE3-S11 C-precursor (8) | >80% |
| Ter ThyX S11 | Ter ThyX | pMTX-S11 N-precursor (9) pMTX-S11 C-precursor (10) | ~60% |
| Ssp GyrB S1 | Ssp GyrB | pMSG-S1 N-precursor (11) pMSG-S1 C-precursor (12) | >90% |
| Rma DnaB S1 | Rma DnaB | pMRT-S1 N-precursor (13) pMRT-S1 C-precursor (14) | >95% |
| Cne Prp8 S1 | Cne Prp8 | pMCP-S1 N-precursor (15) pMCP-S1 C-precursor (16) | ~60% |
| Ssp DnaX S1 | Ssp DnaX | pMSX-S1 N-precursor (17) pMSX-S1 C-precursor (18) | >95% |
| Ter DnaE3 S1 | Ter DnaE-3 | pMTE3-S1 N-precursor (19) pMTE3-S1 C-precursor (20) | >90% |
| Ter ThyX S1 | Ter ThyX | pMTX-S1 N-precursor (21) pMTX-S1 C-precursor (22) | >90% |
| Ter DnaE3 S2 | Ter DnaE-3 | pMTE3-S2 N-precursor (23) pMTE3-S2 C-precursor (24) | ~30% |

TABLE 1-continued

| Name of split intein | Name of natural intein [18] | Sequences of precursor proteins/peptides (SEQ ID NO) | Trans-splicing efficiency |
|---|---|---|---|
| Ssp DnaX 3-piece | Ssp DnaX | pMSX-S1 N-precursor (17)<br>pMSX M-intein (25)<br>pMSX-S11 C-precursor (6) | ~25% |
| Ter ThyX 3-piece | Ter ThyX | pMTX-S1 N-precursor (21)<br>pMTX M-intein (26)<br>pMTX-S11 C-precursor (10) | ~20% |
| Ter DnaE1 S11 | Ter DnaE-1 | pMTE1-S11 N-precursor (31)<br>pMTE1-S11 C-precursor (32) | <5% |
| Ter DnaE1 S1 | Ter DnaE-1 | pMTE1-S1 N-precursor (33)<br>pMTE1-S1 C-precursor (34) | <5% |
| Ter DnaE2 S11 | Ter DnaE-2 | pMTE2-S11 N-precursor (35)<br>pMTE2-S11 C-precursor (36) | <5% |
| Ter DnaE2 S1 | Ter DnaE-2 | pMTE2-S1 N-precursor (37)<br>pMTE2-S1 C-precursor (38) | <10% |
| Ter RIR1 S11 | Ter RIR-1 | pMTR1-S11 N-precursor (39)<br>pMTR1-S11 C-precursor (40) | <5% |
| Ter RIR1 S1 | Ter RIR-1 | pMTR1-S1 N-precursor (41)<br>pMTR1-S1 C-precursor (42) | <5% |
| Ter RIR2 S11 | Ter RIR-2 | pMTR2-S11 N-precursor (43)<br>pMTR2-S11 C-precursor (44) | <5% |
| Ter RIR2 S1 | Ter RIR-2 | pMTR2-S1 N-precursor (45)<br>pMTR2-S1 C-precursor (46) | <5% |
| Ter RIR4 S11 | Ter RIR-4 | pMTR4-S11 N-precursor (47)<br>pMTR4-S11 C-precursor (48) | <5% |
| Ter RIR4 S1 | Ter RIR-4 | pMTR4-S1 N-precursor (49)<br>pMTR4-S1 C-precursor (50) | <5% |
| Tth DnaE1 S11 | Tth DnaE-1 | pMTHE1-S11 N-precursor (51)<br>pMTHE1-S11 C-precursor (52) | <5% |
| Tth DnaE1 S1 | Tth DnaE-1 | pMTHE1-S1 N-precursor (53)<br>pMTHE1-S1 C-precursor (54) | <5% |
| Tth DnaE2 S11 | Tth DnaE-2 | pMTHE2-S11 N-precursor (55)<br>pMTHE2-S11 C-precursor (56) | <5% |
| Tth DnaE2 S1 | Tth DnaE-2 | pMTHE2-S1 N-precursor (57)<br>pMTHE2-S1 C-precursor (58) | <5% |
| Tth RIR1 S11 | Tth RIR-1 | pMTHR-S11 N-precursor (59)<br>pMTHR-S11 C-precursor (60) | <5% |
| Tth RIR1 S1 | Tth RIR-1 | pMTHR-S1 N-precursor (61)<br>pMTHR-S1 C-precursor (62) | <5% |

The description of the embodiment of the invention has been presented for the purpose of illustration; it is not intended to be exhaustive or to limit the invention to the precise forms disclosed. Persons skilled in the relevant art can appreciate that many modifications and variations are possible in light of the embodiment teachings.

It should be noted that the language used in the specification has been principally selected for readability and instructional purposes, and it may not have been selected to delineate or circumscribe the inventive subject matter. Accordingly, the disclosure of the embodiment of the invention is intended to be illustrative, but not limiting, of the scope of the invention.

The singular forms "a," "an" and "the" used throughout herein, include plural referents unless the context clearly dictates otherwise.

Any terms not directly defined herein shall be understood to have the meanings commonly associated with them as understood within the protein splicing and intein art. Certain terms are discussed herein as a guidance to the practitioner in describing the invention. It will be appreciated that the same thing may be said in more than one way. Consequently, alternative language and synonyms may be used for any one or more of the terms discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments of the invention.

References

[1] O'Hare, H. M., et al., (2007) Curr Opin Struct Biol. 17, 488-494.
[2] Miller, L. W., et al., (2005) Curr Opin Chem. Biol. 9, 56-61.
[3] Walsh, C. T., et al., (2005) Angew Chem Int Ed Engl. 44, 7342-7372.
[4] Xie, J., et al., (2005) Curr Opin Chem. Biol. 9, 548-554.
[5] Guignet, E. G., et al., (2004) Nat Biotechnol 22, 440-444.
[6] McCann, C. M., et al., (2005) Biotechniques 38, 945-952.
[7] Muir, T. W., (2008) Biopolymers. 90, 743-750
[8] Pellois, J. P., et al., (2006) Curr Opin Chem. Biol. 10, 487-91.
[9] Muralidharan, V., et al. (2006) Nat Methods 3, 429-38.
[10] Muir, T. W., (2003) Annu Rev Biochem, 72, 249-289.
[11] Foley, T. L., et al. (2007) Curr Opin Chem. Biol. 11, 12-9.
[12] Evans, T. C., Jr., et al., (1999) J Biol Chem 274, 18359-18363.
[13] Lew, B. M., et al., (1999) Biopolymers 51, 355-362.
[14] Mathys, S., et al., (1999) Gene 231, 1-13.
[15] Scott, C. P., et al., (1999) Proc Natl Acad Sci U.S.A. 96, 13638-13643.
[16] Xu, M. Q., et al., (2001) Methods 24, 257-277.
[17] Perler, F. B., et al., (1994) Nucleic Acids Res 22, 1125-1127
[18] Perler, F. B. (2002) Nucleic Acids Res 30, 383-384.
[19] Saleh, L., et al. (2006) Chem Rec 6, 183-193.
[20] Liu, X. Q., et al. (2003) J Biol Chem 278, 26315-26318.
[21] Yang, J., et al. (2004) Mol Microbiol 51, 1185-1192.

[22] Telenti, A., et al. (1997) J Bacteriol 179, 6378-6382.
[23] Wu, H., Xu, M. Q., et al. (1998) Biochim Biophys Acta 1387, 422-432.
[24] Derbyshire, V., et al. (1997) Proc Natl Acad Sci USA 94, 11466-11471.
[25] Duan, X., et al. (1997) Cell 89, 555-564.
[26] Ichiyanagi, K., et al. (2000) J Mol Biol 300, 889-901.
[27] Klabunde, T., et al. (1998) Nat Struct Biol 5, 31-36.
[28] Ding, Y., et al. (2003) J Biol Chem 278, 39133-39142.
[29] Xu, M. Q., et al. (1996) Embo J 15, 5146-5153.
[30] Paulus, H. (2000) Annu Rev Biochem 69, 447-496.
[31] Wu, H., et al. (1998) Proc Natl Acad Sci USA 95, 9226-9231.
[32] Liu, X. Q. (2000) Annu Rev Genet. 34, 61-76.
[33] Caspi, J., et al. (2003) Mol Microbiol 50, 1569-1577.
[34] Mills, K. V., et al. (1998) Proc Natl Acad Sci USA 95, 3543-3548
[35] Southworth, M. W., et al. (1998) Embo J 17, 918-926.
[36] Evans, T. C., Jr., et al. (2000) J Biol Chem 275, 9091-9094.
[37] Chong, S., et al., (1997) Gene 192, 271-281.
[38] Cui, C., et al., (2006) Protein Expr Purif 50, 74-81.
[39] Evans, T. C., Jr., et al., (1998) Protein Sci 7, 2256-2264.
[40] Pietrokovski, S. (1998) Protein Sci 7, 64-71.
[41] Dalgaard, J. Z., et al. (1997) J Comput Biol 4, 193-214.
[42] Sun, W., et al. (2004) J Biol Chem 279, 35281-35286.
[43] Martin, D. D., et al. (2001) Biochemistry 40, 1393-1402.
[44] Appleby, J. H., et al., (2009) J Biol Chem, 284, 6194-6199.
[45] Ciechanover, A., et al., (1983) J Biol Chem, 258, 9681.
[46] Dautry-Varsat, A., et al., (1983) Proc Natl Acad Sci U.S.A. 80, 2258.
[47] Ludwig, C., et al. (2006) Angew Chem Int Ed 45, 5218-5221.
[48] Ando, T., et al., (2007) Chem Commun (Camb), 4995-4997.
[49] Kwon, Y. et al., (2006) Angew Chem Int Ed 45, 1726-1729.

---

The invention claimed is:

1. A method for covalently linking the N-terminus of a peptide to the C-terminus of a peptide, the method comprising providing a C-terminus of a peptide, the C-terminus being covalently linked via a peptide bond to an N-terminal split intein (In);

providing an N-terminus of a peptide, the N-terminus being covalently linked via a peptide bond to a C-terminal split intein (Ic); wherein the Ic is from 4 to 7 contiguous amino acids, at least 4 of which are from the last beta-strand of the C-terminal region of the Ssp GyrB intein, the Ssp DnaX intein, the Ter DnaE3 intein, or the Ter ThyX intein; and wherein the Ic is split from the intein at a site between the penultimate beta-strand and the last beta-strand of the C-terminal region of the intein; and contacting the In-linked C-terminus with the Ic-linked N-terminus in the presence of an intein-splicing polypeptide (ISP) under conditions allowing splicing of the In and the Ic and linking of the C-terminus to the N-terminus; wherein the In, the Ic and the ISP are of the same or cross-reacting intein (I); and wherein the In is from 11 to 20 contiguous amino acids of the N-terminal region of the intein (I); and is split from the intein (I) at a site next to the first or the second beta-strand;

wherein the N-terminus and the C-terminus belong to the same peptide, thereby resulting in a cyclic peptide.

2. The method of claim 1 wherein the In comprises the ISP.

3. A method for covalently linking the N-terminus of a peptide to the C-terminus of a peptide, the method comprising providing a C-terminus of a first peptide, the C-terminus being covalently linked via a peptide bond to a first N-terminal split intein (In1);

providing an N-terminus of a second peptide, the N-terminus being covalently linked via a peptide bond to a first C-terminal split intein (Ic1); wherein the second peptide is also covalently linked at its C-terminus via a peptide bond to a second N-terminal split intein (In2);

wherein the Ic1 is from 4 to 7 contiguous amino acids, at least 4 of which are from the last beta-strand of the C-terminal region of the Ssp GyrB intein, the Ssp DnaX intein, the Ter DnaE3 intein, the Ter ThyX intein, the Rma DnaB intein, or the Cne Prp8 intein; and wherein the Ic1 is split from the intein at a site between the penultimate beta-strand and the last beta-strand of the C-terminal region of the intein;

providing a third peptide covalently linked at its N-terminus via a peptide bond to a second C-terminal split intein (Ic2);

contacting the In1-linked C-terminus of the first peptide with the Ic1-linked N-terminus of the second peptide in the presence of a first intein-splicing polypeptide (ISP1) under conditions allowing splicing of the In1 and the Ic1 and linking of the C-terminus of the first peptide to the N-terminus of the second peptide; wherein the In1, the Ic1 and the ISP1 are of the same or cross-reacting first intein (I1); and contacting the Ic1-linked and In2-linked second peptide with the Ic2-linked third peptide in the presence of a second intein-splicing domain (ISP2) under conditions allowing splicing of the In2 and the Ic2 and linking of the second peptide to the third peptide to produce a fusion of the first peptide, the second peptide and the third peptide; wherein the In2, the Ic2 and the ISP2 are of the same or cross-reacting second intein (I2) which is different from the first intein (I1) and wherein split inteins of I1 and I2 do not cross-react.

4. The method of claim 3 wherein the In1-linked first peptide is covalently linked to the Ic2-linked third peptide via a peptide linker, before being placed in contact with the Ic1-linked and In2-linked second peptide.

5. The method of claim 3 wherein the In2 is from 11 to 20 contiguous amino acids of the N-terminal region of the intein (I2); and is split from the intein (I2) at a site next to the first or the second beta-strand; wherein I2 is the Ssp GyrB intein, the Ssp DnaX intein, the Ter DnaE3 intein, the Ter ThyX intein, the Rma DnaB intein, or the Cne Prp8 intein.

6. A method for covalently linking the N-terminus of a peptide to the C-terminus of a peptide, the method comprising providing a C-terminus of a first peptide, the C-terminus being covalently linked via a peptide bond to an N-terminal split intein (In1); wherein the first peptide is also covalently linked at its N-terminus via a peptide bond to a second C-terminal split intein (Ic2);

providing an N-terminus of a second peptide, the N-terminus being covalently linked via a peptide bond to a first C-terminal split intein (Ic1); wherein the Ic1 is from 4 to 7 contiguous amino acids, at least 4 of which are from the last beta-strand of the C-terminal region of the Ssp GyrB intein, the Ssp DnaX intein, the Ter DnaE3 intein, the Ter ThyX intein, the Rma DnaB intein, or the Cne Prp8 intein; and wherein the Ic1 is split from the intein at a site between the penultimate beta-strand and the last beta-strand of the C-terminal region of the intein; wherein the second peptide is also covalently linked at its C-terminus via a peptide bond to a second N-terminal split intein (In2);

contacting the In1-linked and Ic2-linked first peptide with the Ic1-linked and In2-linked second peptide in the presence of a first intein-splicing polypeptide (ISP1) and a second intein-splicing polypeptide (ISP2) under conditions allowing splicing of the In1 and the Ic1 and linking of the C-terminus of the first peptide to the N-terminus of the second peptide, wherein the In1, the Ic1 and the ISP1 are of the same or cross-reacting first intein (I1); and allowing splicing of the In2 and the Ic2 and linking of the C-terminus of the second peptide to the N-terminus of the first peptide to produce a cyclic fusion of the first peptide and the second peptide, wherein the In2, the Ic2 and the ISP2 are of the same or cross-reacting second intein (I2) which is different from the first intein (I1), and wherein split inteins of I1 and I2 do not cross-react.

7. The method of claim 6 wherein the In2 is from 11 to 20 contiguous amino acids of the N-terminal region of the intein (I2); and is split from the intein (I2) at a site next to the first or the second beta-strand; wherein I2 is the Ssp GyrB intein, the Ssp DnaX intein, the Ter DnaE3 intein, the Ter ThyX intein, the Rma DnaB intein, or the Cne Prp8 intein.

8. The method of claim 3 wherein the first peptide, the second peptide, or the third peptide, is 5 to 100 amino acids.

9. The method of claim 8 wherein the first peptide, the second peptide, or the third peptide, is chemically synthesized.

10. The method of claim 3 wherein the first peptide, the second peptide, or the third peptide, comprises an additional chemical moiety.

11. The method of claim 3 wherein the first peptide, the second peptide, or the third peptide, is provided by expressing a nucleic acid encoding the first peptide, the second peptide, or the third peptide, in a cell or in a cell-free lysate.

12. The method of claim 1 wherein the N-terminus of Ic or the C-terminus of In is fused to an affinity binder.

13. The method of claim 12 wherein the affinity binder is a His-tag.

14. The method of claim 1 wherein the peptide having the Ic-linked N-terminus, or the peptide having the In-linked C-terminus, is 5 to 100 amino acids.

15. The method of claim 1 wherein the peptide having the Ic-linked N-terminus, or the peptide having the In-linked C-terminus, is chemically synthesized.

16. The method of claim 1 wherein the peptide having the Ic-linked N-terminus, or the peptide having the In-linked C-terminus, comprises an additional chemical moiety.

17. The method of claim 1 wherein the peptide having the Ic-linked N-terminus, or the peptide having the In-linked C-terminus, is provided by expressing a nucleic acid encoding the peptide having the Ic-linked N-terminus, or the peptide having the In-linked C-terminus in a cell or in a cell-free lysate.

18. The method of claim 3 wherein In1 or Ic1 comprises ISP1 and In2 or Ic2 comprises ISP2.

19. The method of claim 5 wherein the In1 is from 11 to 20 contiguous amino acids of the N-terminal region of the intein (I1) and is split from the intein (I1) at a site next to the first or the second beta-strand; wherein I1 is the Ssp GyrB intein, the Ssp DnaX intein, the Ter DnaE3 intein, the Ter ThyX intein, the Rma DnaB intein, or the Cne Prp8 intein; wherein the Ic2 is from 4 to 7 contiguous amino acids, at least 4 of which are from the last beta-strand of the C-terminal region of the Ssp GyrB intein, the Ssp DnaX intein, the Ter DnaE3 intein, or the Ter ThyX intein; and wherein the Ic2 is split from the intein at a site between the penultimate beta-strand and the last beta-strand of the C-terminal region of the intein.

20. The method of claim 6 wherein In1 comprises ISP1 and Ic2 comprises ISP2.

21. The method of claim 6 wherein the second peptide is 5 to 100 amino acids.

22. The method of claim 6 wherein the second peptide is chemically synthesized.

23. The method of claim 1 wherein the second peptide comprises an additional chemical moiety.

24. The method of claim 1 wherein the second peptide is provided by expressing a nucleic acid encoding the second peptide in a cell or in a cell-free lysate.

25. The method of claim 7 wherein the In1 is from 11 to 20 contiguous amino acids of the N-terminal region of the intein (I1) and is split from I1 at a site next to the first or the second beta-strand; wherein I1 is the Ssp GyrB intein, the Ssp DnaX intein, the Ter DnaE3 intein, the Ter ThyX intein, the Rma DnaB intein, or the Cne Prp8 intein; wherein Ic2 is from 4 to 7 contiguous amino acids, at least 4 of which are from the last beta-strand of the C-terminal region of the Ssp GyrB intein, the Ssp DnaX intein, the Ter DnaE3 intein, or the Ter ThyX intein; and wherein Ic2 is split from the intein at a site between the penultimate beta-strand and the last beta-strand of the C-terminal region of the intein.

26. The method of claim 1 wherein the In is from 11 to 20 contiguous amino acids of the N-terminal region of the Ssp GyrB intein, the Ssp DnaX intein, the Ter DnaE3 intein, the Ter ThyX intein, the Rma DnaB intein, or the Cne Prp8 intein.

* * * * *

SEQUENCE LISTING

<160> NUMBER OF SEQ ID NOS: 93

<210> SEQ ID NO 1
<211> LENGTH: 391
<212> TYPE: PRT
<213> ORGANISM: Unknown
<220> FEATURE:
<223> OTHER INFORMATION: Bacterial origin

<400> SEQUENCE: 1

```
Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220
```

```
Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
        260                 265                 270

Asn Lys Glu Leu Ala Lys Glu Phe Leu Glu Asn Tyr Leu Leu Thr Asp
    275                 280                 285

Glu Gly Leu Glu Ala Val Asn Lys Asp Lys Pro Leu Gly Ala Val Ala
290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg Gly Thr Leu Glu
385                 390

<210> SEQ ID NO 2
<211> LENGTH: 111
<212> TYPE: PRT
<213> ORGANISM: Unknown
<220> FEATURE:
<223> OTHER INFORMATION: Bacterial origin

<400> SEQUENCE: 2

Thr Gly Met Ser Asp Lys Ile Ile His Leu Thr Asp Asp Ser Phe Asp
1               5                   10                  15

Thr Asp Val Leu Lys Ala Asp Gly Ala Ile Leu Val Asp Phe Trp Ala
            20                  25                  30

Glu Trp Cys Gly Pro Cys Lys Met Ile Ala Pro Ile Leu Asp Glu Ile
        35                  40                  45

Ala Asp Glu Tyr Gln Gly Lys Leu Thr Val Ala Lys Leu Asn Ile Asp
    50                  55                  60

Gln Asn Pro Gly Thr Ala Pro Lys Tyr Gly Ile Arg Gly Ile Pro Thr
65                  70                  75                  80

Leu Leu Leu Phe Lys Asn Gly Glu Val Ala Ala Thr Lys Val Gly Ala
                85                  90                  95

Leu Ser Lys Gly Gln Leu Lys Glu Phe Leu Asp Ala Asn Leu Ala
            100                 105                 110

<210> SEQ ID NO 3
<211> LENGTH: 158
<212> TYPE: PRT
<213> ORGANISM: Artificial sequence
<220> FEATURE:
<223> OTHER INFORMATION: pMSG-S11 N-precursor

<400> SEQUENCE: 3

Gly Gly Cys Phe Ser Gly Asp Thr Leu Val Ala Leu Thr Asp Gly Arg
1               5                   10                  15

Ser Val Ser Phe Glu Gln Leu Val Glu Glu Lys Gln Gly Lys Gln
            20                  25                  30
```

```
Asn Phe Cys Tyr Thr Ile Arg His Asp Gly Ser Ile Gly Val Glu Lys
            35                  40                  45

Ile Ile Asn Ala Arg Lys Thr Lys Thr Asn Ala Lys Val Ile Lys Val
 50                  55                  60

Thr Leu Asp Asn Gly Glu Ser Ile Ile Cys Thr Pro Asp His Lys Phe
 65                  70                  75                  80

Met Leu Arg Asp Gly Ser Tyr Lys Cys Ala Met Asp Leu Thr Leu Asp
                 85                  90                  95

Asp Ser Leu Met Pro Leu His Arg Lys Ile Ser Thr Thr Glu Asp Ser
                100                 105                 110

Gly His Met Glu Ala Val Leu Asn Tyr Asn His Arg Ile Val Asn Ile
            115                 120                 125

Glu Ala Val Ser Glu Thr Ile Asp Val Tyr Asp Ile Glu Val Pro His
130                 135                 140

Thr His Asn Phe Ala Leu Ala Ser His His His His His
145                 150                 155
```

<210> SEQ ID NO 4
<211> LENGTH: 11
<212> TYPE: PRT
<213> ORGANISM: Artificial sequence
<220> FEATURE:
<223> OTHER INFORMATION: pMSG-S11 C-precursor

<400> SEQUENCE: 4

```
Met Gly Val Phe Val His Asn Ser Ala Gly Glu
 1               5                  10
```

<210> SEQ ID NO 5
<211> LENGTH: 144
<212> TYPE: PRT
<213> ORGANISM: Artificial sequence
<220> FEATURE:
<223> OTHER INFORMATION: pMSX-S11 N-precursor

<400> SEQUENCE: 5

```
Ile Asp Glu Cys Leu Thr Gly Asp Ser Gln Val Leu Thr Arg Asn Gly
 1               5                  10                  15

Leu Met Ser Ile Asp Asn Pro Gln Ile Lys Gly Arg Glu Val Leu Ser
            20                  25                  30

Tyr Asn Glu Thr Leu Gln Gln Trp Glu Tyr Lys Lys Val Leu Arg Trp
            35                  40                  45

Leu Asp Arg Gly Glu Lys Gln Thr Leu Ser Ile Lys Thr Lys Asn Ser
 50                  55                  60

Thr Val Arg Cys Thr Ala Asn His Leu Ile Arg Thr Glu Gln Gly Trp
 65                  70                  75                  80

Thr Arg Ala Glu Asn Ile Thr Pro Gly Met Lys Ile Leu Ser Pro Ala
                 85                  90                  95

Ser Gly His His His His His Gly Gly Ser Gly Ser Pro Gln Trp
                100                 105                 110

His Thr Asn Phe Glu Glu Val Glu Ser Val Thr Lys Gly Gln Val Glu
            115                 120                 125

Lys Val Tyr Asp Leu Glu Val Glu Asp Asn His Asn Phe Val Ala Asn
130                 135                 140
```

<210> SEQ ID NO 6
<211> LENGTH: 9
<212> TYPE: PRT
<213> ORGANISM: Artificial sequence

```
<220> FEATURE:
<223> OTHER INFORMATION: pMSX-S11 C-precursor

<400> SEQUENCE: 6

Met Gly Leu Leu Val His Asn Cys His
1               5

<210> SEQ ID NO 7
<211> LENGTH: 151
<212> TYPE: PRT
<213> ORGANISM: Artificial sequence
<220> FEATURE:
<223> OTHER INFORMATION: pMTE3-S11 N-precursor

<400> SEQUENCE: 7

Lys Phe Ala Glu Tyr Cys Leu Thr Tyr Glu Thr Glu Ile Met Thr Val
1               5                   10                  15

Glu Tyr Gly Pro Leu Pro Ile Gly Lys Ile Val Glu Tyr Arg Ile Glu
                20                  25                  30

Cys Thr Val Tyr Thr Val Asp Lys Asn Gly Tyr Ile Tyr Thr Gln Pro
            35                  40                  45

Ile Ala Gln Trp His Asn Arg Gly Met Gln Glu Val Tyr Glu Tyr Ser
    50                  55                  60

Leu Glu Asp Gly Thr Val Ile Arg Ala Thr Pro Glu His Lys Phe Met
65                  70                  75                  80

Thr Glu Asp Gly Gln Met Leu Pro Ile Asp Glu Ile Phe Glu Arg Asn
                85                  90                  95

Leu Asp Leu Lys Cys Leu Gly Thr Leu Glu Leu Glu Ala Ser Gly His
            100                 105                 110

His His His His His Gly Gly Ser Gly Ser Val Lys Ile Val Ser Arg
        115                 120                 125

Lys Leu Ala Lys Thr Glu Asn Val Tyr Asp Ile Gly Val Thr Lys Asp
    130                 135                 140

His Asn Phe Val Leu Ala Asn
145                 150

<210> SEQ ID NO 8
<211> LENGTH: 12
<212> TYPE: PRT
<213> ORGANISM: Artificial sequence
<220> FEATURE:
<223> OTHER INFORMATION: pMTE3-S11 C-precursor

<400> SEQUENCE: 8

Met Gly Leu Ile Ala Ser Asn Cys Phe Asn Lys Ser
1               5                   10

<210> SEQ ID NO 9
<211> LENGTH: 177
<212> TYPE: PRT
<213> ORGANISM: Artificial sequence
<220> FEATURE:
<223> OTHER INFORMATION: pMTX-S11 N-precursor

<400> SEQUENCE: 9

His Arg Ile Gly Cys Cys Leu Ser Gly Asn Thr Lys Val Arg Phe Arg
1               5                   10                  15

Tyr Ser Ser Ser Ser Gln Glu Ala Lys Tyr Tyr Glu Glu Thr Ile Glu
                20                  25                  30

Lys Leu Ala Asn Leu Trp His Tyr Gly Ser Lys Asn Gln Tyr Thr Ser
            35                  40                  45
```

```
Lys Asp Ala Lys Cys Met Gln Glu Asn Ile Ser Ser Arg Asn Ile Phe
         50                  55                  60
Thr Leu Asp Thr Gln Thr Asn Gln Ile Val Ser Ser Lys Ile Thr Asn
 65                  70                  75                  80
Ile Tyr Ile Asn Gly Glu Lys Glu Thr Tyr Thr Ile Lys Thr Val Ser
                 85                  90                  95
Gly Lys Glu Ile Arg Ala Thr Leu Glu His Gln Phe Trp Thr Asn Gln
            100                 105                 110
Gly Trp Lys Arg Leu Lys Asp Phe Asn Asn Ser Thr Gln Leu Cys Glu
        115                 120                 125
Val Gln Leu Ala Ser Gly His His His His His Gly Gly Ser Gly
    130                 135                 140
Ser Gly Val Phe Val Glu Ile Glu Ser Ile Glu Lys Phe Gly Lys Glu
145                 150                 155                 160
Ile Thr Tyr Asp Leu Glu Val Glu His Pro Glu His Asn Phe Ile Ala
                165                 170                 175
Asn

<210> SEQ ID NO 10
<211> LENGTH: 12
<212> TYPE: PRT
<213> ORGANISM: Artificial sequence
<220> FEATURE:
<223> OTHER INFORMATION: pMTX-S11 C-precursor

<400> SEQUENCE: 10

Met Gly Leu Val Val His Asn Ser Phe Asp Val Gln
 1               5                  10

<210> SEQ ID NO 11
<211> LENGTH: 14
<212> TYPE: PRT
<213> ORGANISM: Artificial sequence
<220> FEATURE:
<223> OTHER INFORMATION: pMSG-S1 N-precursor

<400> SEQUENCE: 11

Gly Gly Cys Phe Ser Gly Asp Thr Leu Val Ala Leu Thr Asp
 1               5                  10

<210> SEQ ID NO 12
<211> LENGTH: 157
<212> TYPE: PRT
<213> ORGANISM: Artificial sequence
<220> FEATURE:
<223> OTHER INFORMATION: pMSG-S1 C-precursor

<400> SEQUENCE: 12

Met Gly Arg Ser Val Ser Phe Glu Gln Leu Val Glu Glu Lys Gln
 1               5                  10                  15
Gly Lys Gln Asn Phe Cys Tyr Thr Ile Arg His Asp Gly Ser Ile Gly
             20                  25                  30
Val Glu Lys Ile Ile Asn Ala Arg Lys Thr Lys Thr Asn Ala Lys Val
         35                  40                  45
Ile Lys Val Thr Leu Asp Asn Gly Glu Ser Ile Ile Cys Thr Pro Asp
     50                  55                  60
His Lys Phe Met Leu Arg Asp Gly Ser Tyr Lys Cys Ala Met Asp Leu
 65                  70                  75                  80
Thr Leu Asp Asp Ser Leu Met Pro Leu His Arg Lys Ile Ser Thr Thr
                 85                  90                  95
```

```
Glu Asp Ser Gly His Ser His His His His Ser Met Glu Ala
            100                 105                 110

Val Leu Asn Tyr Asn His Arg Ile Val Asn Ile Ala Val Ser Glu
        115                 120                 125

Thr Ile Asp Val Tyr Asp Ile Glu Val Pro His Thr His Asn Phe Ala
        130                 135                 140

Leu Ala Ser Gly Val Phe Val His Asn Ser Ala Gly Glu
145                 150                 155

<210> SEQ ID NO 13
<211> LENGTH: 17
<212> TYPE: PRT
<213> ORGANISM: Artificial sequence
<220> FEATURE:
<223> OTHER INFORMATION: pMRT-S1 N-precursor

<400> SEQUENCE: 13

Leu Arg Glu Ser Gly Cys Leu Ala Gly Asp Thr Leu Ile Thr Leu Ala
1               5                   10                  15

Ser

<210> SEQ ID NO 14
<211> LENGTH: 152
<212> TYPE: PRT
<213> ORGANISM: Artificial sequence
<220> FEATURE:
<223> OTHER INFORMATION: pMRT-S1 C-precursor

<400> SEQUENCE: 14

Met Asp Gly Arg Arg Val Pro Ile Arg Glu Leu Val Ser Gln Gln Asn
1               5                   10                  15

Phe Ser Val Trp Ala Leu Asn Pro Gln Thr Tyr Arg Leu Glu Arg Ala
                20                  25                  30

Arg Val Ser Arg Ala Phe Cys Thr Gly Ile Lys Pro Val Tyr Arg Leu
            35                  40                  45

Thr Thr Arg Leu Gly Arg Ser Ile Arg Ala Thr Ala Asn His Arg Phe
        50                  55                  60

Leu Thr Pro Gln Gly Trp Lys Arg Val Asp Glu Leu Gln Pro Gly Asp
65                  70                  75                  80

Tyr Leu Ala Leu Pro Arg Arg Ile Pro Ser His His His His His His
                85                  90                  95

Pro Arg Val Leu Ala Ser Met Ala Ala Gln Ser Asp Val Tyr Trp Asp
            100                 105                 110

Pro Ile Val Ser Ile Glu Pro Asp Gly Val Glu Glu Val Phe Asp Leu
        115                 120                 125

Thr Val Pro Gly Pro His Asn Phe Val Ala Asn Asp Ile Ile Ala His
        130                 135                 140

Asn Ser Ile Glu Asn Ile Val Asp
145                 150

<210> SEQ ID NO 15
<211> LENGTH: 15
<212> TYPE: PRT
<213> ORGANISM: Artificial sequence
<220> FEATURE:
<223> OTHER INFORMATION: pMCP-S1 N-precursor

<400> SEQUENCE: 15

Phe Trp Glu Lys Ala Cys Leu Gln Asn Gly Thr Arg Leu Leu Arg
1               5                   10                  15
```

<210> SEQ ID NO 16
<211> LENGTH: 180
<212> TYPE: PRT
<213> ORGANISM: Artificial sequence
<220> FEATURE:
<223> OTHER INFORMATION: pMCP-S1 C-precursor

<400> SEQUENCE: 16

```
Met Ala Asp Gly Ser Glu Val Leu Val Glu Asp Val Gln Glu Gly Asp
1               5                   10                  15

Gln Leu Leu Gly Pro Asp Gly Thr Ser Arg Thr Ala Ser Lys Ile Val
            20                  25                  30

Arg Gly Glu Glu Arg Leu Tyr Arg Ile Lys Thr His Glu Gly Leu Glu
        35                  40                  45

Asp Leu Val Cys Thr His Asn His Ile Leu Ser Met Tyr Lys Glu Arg
    50                  55                  60

Ser Gly Ser Glu Arg Ala His Ser Pro Ser Ala Asp Leu Ser Leu Thr
65                  70                  75                  80

Asp Ser His Glu Arg Val Asp Val Thr Val Asp Asp Phe Val Arg Leu
                85                  90                  95

Pro Gln Gln Glu Gln Lys Tyr Gln Leu Phe Arg Ser Thr Ala Ser
            100                 105                 110

Gly His His His His His Gly Ser Gly Ser Val Arg His Glu
            115                 120                 125

Arg Pro Ser Thr Ser Lys Leu Asp Thr Thr Leu Leu Arg Ile Asn Ser
        130                 135                 140

Ile Glu Leu Glu Asp Glu Pro Thr Lys Trp Ser Gly Phe Val Val Asp
145                 150                 155                 160

Lys Asp Ser Leu Tyr Leu Arg His Asp Tyr Leu Val Leu His Asn Ser
                165                 170                 175

Gly Phe Glu Glu
            180
```

<210> SEQ ID NO 17
<211> LENGTH: 14
<212> TYPE: PRT
<213> ORGANISM: Artificial sequence
<220> FEATURE:
<223> OTHER INFORMATION: pMSX-S1 N-precursor

<400> SEQUENCE: 17

```
Ile Asp Glu Cys Leu Thr Gly Asp Ser Gln Val Leu Thr Arg
1               5                   10
```

<210> SEQ ID NO 18
<211> LENGTH: 139
<212> TYPE: PRT
<213> ORGANISM: Artificial sequence
<220> FEATURE:
<223> OTHER INFORMATION: pMSX-S1 C-precursor

<400> SEQUENCE: 18

```
Met Asn Gly Leu Met Ser Ile Asp Asn Pro Gln Ile Lys Gly Arg Glu
1               5                   10                  15

Val Leu Ser Tyr Asn Glu Thr Leu Gln Gln Trp Glu Tyr Lys Lys Val
            20                  25                  30

Leu Arg Trp Leu Asp Arg Gly Glu Lys Gln Thr Leu Ser Ile Lys Thr
        35                  40                  45

Lys Asn Ser Thr Val Arg Cys Thr Ala Asn His Leu Ile Arg Thr Glu
    50                  55                  60
```

```
Gln Gly Trp Thr Arg Ala Glu Asn Ile Thr Pro Gly Met Lys Ile Leu
 65                  70                  75                  80

Ser Pro Ala Ser Gly His His His His His Gly Gly Ser Gly Ser
             85                  90                  95

Pro Gln Trp His Thr Asn Phe Glu Glu Val Glu Ser Val Thr Lys Gly
            100                 105                 110

Gln Val Glu Lys Val Tyr Asp Leu Glu Val Glu Asp Asn His Asn Phe
            115                 120                 125

Val Ala Asn Gly Leu Leu Val His Asn Cys His
            130                 135

<210> SEQ ID NO 19
<211> LENGTH: 16
<212> TYPE: PRT
<213> ORGANISM: Artificial sequence
<220> FEATURE:
<223> OTHER INFORMATION: pMTE3-S1 N-precursor

<400> SEQUENCE: 19

Lys Phe Ala Glu Tyr Cys Leu Thr Tyr Glu Thr Glu Ile Met Thr Val
  1               5                  10                  15

<210> SEQ ID NO 20
<211> LENGTH: 147
<212> TYPE: PRT
<213> ORGANISM: Artificial sequence
<220> FEATURE:
<223> OTHER INFORMATION: pMTE3-S1 C-precursor

<400> SEQUENCE: 20

Met Glu Tyr Gly Pro Leu Pro Ile Gly Lys Ile Val Glu Tyr Arg Ile
  1               5                  10                  15

Glu Cys Thr Val Tyr Thr Val Asp Lys Asn Gly Tyr Ile Tyr Thr Gln
             20                  25                  30

Pro Ile Ala Gln Trp His Asn Arg Gly Met Gln Glu Val Tyr Glu Tyr
             35                  40                  45

Ser Leu Glu Asp Gly Thr Val Ile Arg Ala Thr Pro Glu His Lys Phe
 50                  55                  60

Met Thr Glu Asp Gly Gln Met Leu Pro Ile Asp Glu Ile Phe Glu Arg
 65                  70                  75                  80

Asn Leu Asp Leu Lys Cys Leu Gly Thr Leu Glu Leu Glu Ala Ser Gly
             85                  90                  95

His His His His His Gly Gly Ser Gly Ser Val Lys Ile Val Ser
            100                 105                 110

Arg Lys Leu Ala Lys Thr Glu Asn Val Tyr Asp Ile Gly Val Thr Lys
            115                 120                 125

Asp His Asn Phe Val Leu Ala Asn Gly Leu Ile Ala Ser Asn Cys Phe
            130                 135                 140

Asn Lys Ser
145

<210> SEQ ID NO 21
<211> LENGTH: 17
<212> TYPE: PRT
<213> ORGANISM: Artificial sequence
<220> FEATURE:
<223> OTHER INFORMATION: pMTX-S1 N-precursor

<400> SEQUENCE: 21

His Arg Ile Gly Cys Cys Leu Ser Gly Asn Thr Lys Val Arg Phe Arg
```

Tyr

<210> SEQ ID NO 22
<211> LENGTH: 172
<212> TYPE: PRT
<213> ORGANISM: Artificial sequence
<220> FEATURE:
<223> OTHER INFORMATION: pMTX-S1 C-precursor

<400> SEQUENCE: 22

```
Met Ser Ser Ser Gln Glu Ala Lys Tyr Tyr Glu Glu Thr Ile Glu
1               5                   10                  15

Lys Leu Ala Asn Leu Trp His Tyr Gly Ser Lys Asn Gln Tyr Thr Ser
                20                  25                  30

Lys Asp Ala Lys Cys Met Gln Glu Asn Ile Ser Ser Arg Asn Ile Phe
            35                  40                  45

Thr Leu Asp Thr Gln Thr Asn Gln Ile Val Ser Lys Ile Thr Asn
        50                  55                  60

Ile Tyr Ile Asn Gly Glu Lys Glu Thr Tyr Thr Ile Lys Thr Val Ser
65                  70                  75                  80

Gly Lys Glu Ile Arg Ala Thr Leu Glu His Gln Phe Trp Thr Asn Gln
                85                  90                  95

Gly Trp Lys Arg Leu Lys Asp Phe Asn Asn Ser Thr Gln Leu Cys Glu
            100                 105                 110

Val Gln Leu Ala Ser Gly His His His His His Gly Gly Ser Gly
        115                 120                 125

Ser Gly Val Phe Val Glu Ile Glu Ser Ile Glu Lys Phe Gly Lys Glu
    130                 135                 140

Ile Thr Tyr Asp Leu Glu Val Glu His Pro Glu His Asn Phe Ile Ala
145                 150                 155                 160

Asn Gly Leu Val Val His Asn Ser Phe Asp Val Gln
                165                 170
```

<210> SEQ ID NO 23
<211> LENGTH: 9
<212> TYPE: PRT
<213> ORGANISM: Artificial sequence
<220> FEATURE:
<223> OTHER INFORMATION: pMTE3-S2 N-precursor

<400> SEQUENCE: 23

```
Lys Phe Ala Glu Tyr Cys Leu Thr Tyr
1               5
```

<210> SEQ ID NO 24
<211> LENGTH: 154
<212> TYPE: PRT
<213> ORGANISM: Artificial sequence
<220> FEATURE:
<223> OTHER INFORMATION: pMTE3-S2 C-precursor

<400> SEQUENCE: 24

```
Met Glu Thr Glu Ile Met Thr Val Glu Tyr Gly Pro Leu Pro Ile Gly
1               5                   10                  15

Lys Ile Val Glu Tyr Arg Ile Glu Cys Thr Val Tyr Thr Val Asp Lys
                20                  25                  30

Asn Gly Tyr Ile Tyr Thr Gln Pro Ile Ala Gln Trp His Asn Arg Gly
            35                  40                  45

Met Gln Glu Val Tyr Glu Tyr Ser Leu Glu Asp Gly Thr Val Ile Arg
```

```
                50                  55                  60
Ala Thr Pro Glu His Lys Phe Met Thr Glu Asp Gly Gln Met Leu Pro
 65                  70                  75                  80

Ile Asp Glu Ile Phe Glu Arg Asn Leu Asp Leu Lys Cys Leu Gly Thr
                 85                  90                  95

Leu Glu Leu Glu Ala Ser Gly His His His His His His Gly Gly Ser
                100                 105                 110

Gly Ser Val Lys Ile Val Ser Arg Lys Leu Ala Lys Thr Glu Asn Val
                115                 120                 125

Tyr Asp Ile Gly Val Thr Lys Asp His Asn Phe Val Leu Ala Asn Gly
                130                 135                 140

Leu Ile Ala Ser Asn Cys Phe Asn Lys Ser
145                 150

<210> SEQ ID NO 25
<211> LENGTH: 131
<212> TYPE: PRT
<213> ORGANISM: Artificial sequence
<220> FEATURE:
<223> OTHER INFORMATION: pMSX M-intein

<400> SEQUENCE: 25

Met Asn Gly Leu Met Ser Ile Asp Asn Pro Gln Ile Lys Gly Arg Glu
  1               5                  10                  15

Val Leu Ser Tyr Asn Glu Thr Leu Gln Gln Trp Glu Tyr Lys Lys Val
                 20                  25                  30

Leu Arg Trp Leu Asp Arg Gly Glu Lys Gln Thr Leu Ser Ile Lys Thr
                 35                  40                  45

Lys Asn Ser Thr Val Arg Cys Thr Ala Asn His Leu Ile Arg Thr Glu
 50                  55                  60

Gln Gly Trp Thr Arg Ala Glu Asn Ile Thr Pro Gly Met Lys Ile Leu
 65                  70                  75                  80

Ser Pro Ala Ser Gly His His His His His Gly Gly Ser Gly Ser
                 85                  90                  95

Pro Gln Trp His Thr Asn Phe Glu Glu Val Glu Ser Val Thr Lys Gly
                100                 105                 110

Gln Val Glu Lys Val Tyr Asp Leu Glu Val Glu Asp Asn His Asn Phe
                115                 120                 125

Val Ala Asn
130

<210> SEQ ID NO 26
<211> LENGTH: 161
<212> TYPE: PRT
<213> ORGANISM: Artificial sequence
<220> FEATURE:
<223> OTHER INFORMATION: pMTX M-intein

<400> SEQUENCE: 26

Met Ser Ser Ser Gln Glu Ala Lys Tyr Tyr Glu Glu Thr Ile Glu
  1               5                  10                  15

Lys Leu Ala Asn Leu Trp His Tyr Gly Ser Lys Asn Gln Tyr Thr Ser
                 20                  25                  30

Lys Asp Ala Lys Cys Met Gln Glu Asn Ile Ser Ser Arg Asn Ile Phe
                 35                  40                  45

Thr Leu Asp Thr Gln Thr Asn Gln Ile Val Ser Ser Lys Ile Thr Asn
 50                  55                  60

Ile Tyr Ile Asn Gly Glu Lys Glu Thr Tyr Thr Ile Lys Thr Val Ser
```

```
                65                  70                  75                  80
Gly Lys Glu Ile Arg Ala Thr Leu Glu His Gln Phe Trp Thr Asn Gln
                    85                  90                  95
Gly Trp Lys Arg Leu Lys Asp Phe Asn Asn Ser Thr Gln Leu Cys Glu
                    100                 105                 110
Val Gln Leu Ala Ser Gly His His His His His Gly Gly Ser Gly
            115                 120                 125
Ser Gly Val Phe Val Glu Ile Glu Ser Ile Glu Lys Phe Gly Lys Glu
            130                 135                 140
Ile Thr Tyr Asp Leu Glu Val Glu His Pro Glu His Asn Phe Ile Ala
145                 150                 155                 160
Asn

<210> SEQ ID NO 27
<211> LENGTH: 152
<212> TYPE: PRT
<213> ORGANISM: Artificial sequence
<220> FEATURE:
<223> OTHER INFORMATION: pM3T N-precursor

<400> SEQUENCE: 27

Gly Gly Cys Phe Ser Gly Asp Thr Leu Val Ala Leu Thr Asp Gly Arg
1               5                   10                  15
Ser Val Ser Phe Glu Gln Leu Val Glu Glu Lys Gln Gly Lys Gln
            20                  25                  30
Asn Phe Cys Tyr Thr Ile Arg His Asp Gly Ser Ile Gly Val Glu Lys
            35                  40                  45
Ile Ile Asn Ala Arg Lys Thr Lys Thr Asn Ala Lys Val Ile Lys Val
50                  55                  60
Thr Leu Asp Asn Gly Glu Ser Ile Ile Cys Thr Pro Asp His Lys Phe
65                  70                  75                  80
Met Leu Arg Asp Gly Ser Tyr Lys Cys Ala Met Asp Leu Thr Leu Asp
                    85                  90                  95
Asp Ser Leu Met Pro Leu His Arg Lys Ile Ser Thr Thr Glu Asp Ser
                100                 105                 110
Gly His Met Glu Ala Val Leu Asn Tyr Asn His Arg Ile Val Asn Ile
            115                 120                 125
Glu Ala Val Ser Glu Thr Ile Asp Val Tyr Asp Ile Glu Val Pro His
            130                 135                 140
Thr His Asn Phe Ala Leu Ala Ser
145                 150

<210> SEQ ID NO 28
<211> LENGTH: 38
<212> TYPE: PRT
<213> ORGANISM: Artificial sequence
<220> FEATURE:
<223> OTHER INFORMATION: pM3T H-peptide

<400> SEQUENCE: 28

Met Gly Val Phe Val His Asn Ser Ala Gly Thr Gly His His His
1               5                   10                  15
His His His Leu Glu Leu Arg Glu Ser Gly Cys Leu Ala Gly Asp Thr
            20                  25                  30
Leu Ile Thr Leu Ala Ser
        35

<210> SEQ ID NO 29
```

```
<211> LENGTH: 144
<212> TYPE: PRT
<213> ORGANISM: Artificial sequence
<220> FEATURE:
<223> OTHER INFORMATION: pM3T C-precursor

<400> SEQUENCE: 29

Met Asp Gly Arg Arg Val Pro Ile Arg Glu Leu Val Ser Gln Gln Asn
1               5                   10                  15

Phe Ser Val Trp Ala Leu Asn Pro Gln Thr Tyr Arg Leu Glu Arg Ala
            20                  25                  30

Arg Val Ser Arg Ala Phe Cys Thr Gly Ile Lys Pro Val Tyr Arg Leu
        35                  40                  45

Thr Thr Arg Leu Gly Arg Ser Ile Arg Ala Thr Ala Asn His Arg Phe
    50                  55                  60

Leu Thr Pro Gln Gly Trp Lys Arg Val Asp Glu Leu Gln Pro Gly Asp
65                  70                  75                  80

Tyr Leu Ala Leu Pro Arg Arg Ile Pro Arg Val Leu Ala Ser Met Ala
                85                  90                  95

Ala Gln Ser Asp Val Tyr Trp Asp Pro Ile Val Ser Ile Glu Pro Asp
            100                 105                 110

Gly Val Glu Val Phe Asp Leu Thr Val Pro Gly Pro His Asn Phe
        115                 120                 125

Val Ala Asn Asp Ile Ile Ala His Asn Ser Ile Glu Asn Ile Val Asp
    130                 135                 140

<210> SEQ ID NO 30
<211> LENGTH: 323
<212> TYPE: PRT
<213> ORGANISM: Artificial sequence
<220> FEATURE:
<223> OTHER INFORMATION: pMTF precursor

<400> SEQUENCE: 30

Gly Gly Cys Phe Ser Gly Asp Thr Leu Val Ala Leu Thr Asp Gly Arg
1               5                   10                  15

Ser Val Ser Phe Glu Gln Leu Val Glu Glu Lys Gln Gly Lys Gln
            20                  25                  30

Asn Phe Cys Tyr Thr Ile Arg His Asp Gly Ser Ile Gly Val Glu Lys
        35                  40                  45

Ile Ile Asn Ala Arg Lys Thr Lys Thr Asn Ala Lys Val Ile Lys Val
    50                  55                  60

Thr Leu Asp Asn Gly Glu Ser Ile Ile Cys Thr Pro Asp His Lys Phe
65                  70                  75                  80

Met Leu Arg Asp Gly Ser Tyr Lys Cys Ala Met Asp Leu Thr Leu Asp
                85                  90                  95

Asp Ser Leu Met Pro Leu His Arg Lys Ile Ser Thr Thr Glu Asp Ser
            100                 105                 110

Gly His Met Glu Ala Val Leu Asn Tyr Asn His Arg Ile Val Asn Ile
        115                 120                 125

Glu Ala Val Ser Glu Thr Ile Asp Val Tyr Asp Ile Glu Val Pro His
    130                 135                 140

Thr His Asn Phe Ala Leu Ala Ser Gly Gly Ser Gly Gly Gly Ser
145                 150                 155                 160

Gly Gly His His His His His Gly Gly Ser Gly Gly Gly Ser Gly
                165                 170                 175

Gly Ser Gly Met Asp Gly Arg Arg Val Pro Ile Arg Glu Leu Val Ser
            180                 185                 190
```

```
Gln Gln Asn Phe Ser Val Trp Ala Leu Asn Pro Gln Thr Tyr Arg Leu
        195                 200                 205

Glu Arg Ala Arg Val Ser Arg Ala Phe Cys Thr Gly Ile Lys Pro Val
    210                 215                 220

Tyr Arg Leu Thr Thr Arg Leu Gly Arg Ser Ile Arg Ala Thr Ala Asn
225                 230                 235                 240

His Arg Phe Leu Thr Pro Gln Gly Trp Lys Arg Val Asp Glu Leu Gln
                245                 250                 255

Pro Gly Asp Tyr Leu Ala Leu Pro Arg Arg Ile Pro Arg Val Leu Ala
            260                 265                 270

Ser Met Ala Ala Gln Ser Asp Val Tyr Trp Asp Pro Ile Val Ser Ile
        275                 280                 285

Glu Pro Asp Gly Val Glu Val Phe Asp Leu Thr Val Pro Gly Pro
    290                 295                 300

His Asn Phe Val Ala Asn Asp Ile Ile Ala His Asn Ser Ile Glu Asn
305                 310                 315                 320

Ile Val Asp

<210> SEQ ID NO 31
<211> LENGTH: 151
<212> TYPE: PRT
<213> ORGANISM: Artificial sequence
<220> FEATURE:
<223> OTHER INFORMATION: pMTE1-S11 N-precursor

<400> SEQUENCE: 31

Thr Tyr Gly Val Leu Cys Leu Pro Lys Gly Thr Leu Ile Asp Gln Pro
1               5                   10                  15

Asp Gly Ser Arg Glu Ala Ile Glu Asn Ile Lys Ser Gly Glu Val Ile
            20                  25                  30

Leu Thr Ser Asp Gly Arg Lys Val Trp Glu Ala Lys Val Ala Lys Gln
        35                  40                  45

Trp Arg Ser Gly Val Arg Glu Ile Leu Lys Ile Thr Leu Ser Ser Gly
    50                  55                  60

Thr Val Ile Tyr Ser Gly Lys Asn His Arg Phe Leu Thr Pro Glu Gly
65                  70                  75                  80

Asp Lys Phe Ala Trp Glu Leu Gln Pro Gln Val Gly Arg Val Lys Asn
                85                  90                  95

Ala Leu Ile Tyr Gly Ser Ala Ser Gly His His His His His Gly
            100                 105                 110

Gly Ser Gly Ser Gln Asp Val Arg Val Val His Val Val Ser Val Glu
        115                 120                 125

Glu Val Gly Glu Ala Glu Cys Phe Asp Leu Glu Met Glu Asp Gln Ser
    130                 135                 140

Ser Pro Tyr Phe Leu Ala Glu
145                 150

<210> SEQ ID NO 32
<211> LENGTH: 12
<212> TYPE: PRT
<213> ORGANISM: Artificial sequence
<220> FEATURE:
<223> OTHER INFORMATION: pMTE1-S11 C-precursor

<400> SEQUENCE: 32

Met Gly Val Val Val His Asn Cys Tyr Gln Glu Gln
1               5                   10
```

<210> SEQ ID NO 33
<211> LENGTH: 17
<212> TYPE: PRT
<213> ORGANISM: Artificial sequence
<220> FEATURE:
<223> OTHER INFORMATION: pMTE1-S1 N-precursor

<400> SEQUENCE: 33

```
Thr Tyr Gly Val Leu Cys Leu Pro Lys Gly Thr Leu Ile Asp Gln Pro
1               5                   10                  15

Asp
```

<210> SEQ ID NO 34
<211> LENGTH: 147
<212> TYPE: PRT
<213> ORGANISM: Artificial sequence
<220> FEATURE:
<223> OTHER INFORMATION: pMTE1-S1 C-precursor

<400> SEQUENCE: 34

```
Met Gly Ser Arg Glu Ala Ile Glu Asn Ile Lys Ser Gly Glu Val Ile
1               5                   10                  15

Leu Thr Ser Asp Gly Arg Lys Val Trp Glu Ala Lys Val Ala Lys Gln
            20                  25                  30

Trp Arg Ser Gly Val Arg Glu Ile Leu Lys Ile Thr Leu Ser Ser Gly
        35                  40                  45

Thr Val Ile Tyr Ser Gly Lys Asn His Arg Phe Leu Thr Pro Glu Gly
    50                  55                  60

Asp Lys Phe Ala Trp Glu Leu Gln Pro Gln Val Gly Arg Val Lys Asn
65                  70                  75                  80

Ala Leu Ile Tyr Gly Ser Ala Ser Gly His His His His His His Gly
                85                  90                  95

Gly Ser Gly Ser Gln Asp Val Arg Val Val His Val Val Ser Val Glu
            100                 105                 110

Glu Val Gly Glu Ala Glu Cys Phe Asp Leu Glu Met Glu Asp Gln Ser
        115                 120                 125

Ser Pro Tyr Phe Leu Ala Glu Met Gly Val Val Val His Asn Cys Tyr
    130                 135                 140

Gln Glu Gln
145
```

<210> SEQ ID NO 35
<211> LENGTH: 153
<212> TYPE: PRT
<213> ORGANISM: Artificial sequence
<220> FEATURE:
<223> OTHER INFORMATION: pMTE2-S11 N-precursor

<400> SEQUENCE: 35

```
Asp Leu Leu Arg Arg Cys Leu Ser Gly Ser Thr Lys Val Ile Asp Ala
1               5                   10                  15

Ala Thr Gly Asn Leu Phe Ser Leu Lys Glu Ile Ala Ala Gln Pro Glu
            20                  25                  30

Tyr Trp Leu Ser Arg Lys Val Phe Ser Leu Asp Leu Lys Ser Gln Gln
        35                  40                  45

Val Val Gln Gln Pro Ile Thr Glu Ile His Pro Asn Gly Val Arg Asp
    50                  55                  60

Val Trp Gln Ile Thr Thr Arg Thr Asn Arg Lys Val Cys Ala Thr Asp
65                  70                  75                  80
```

```
Asp His Leu Phe Tyr Thr Val Leu Gly Trp Lys Pro Leu Lys Asp Phe
            85                  90                  95

Ser Val Gly Asp Arg Leu Gly Leu Pro Asn Lys Ala Ser Gly His His
            100                 105                 110

His His His His Gly Gly Ser Gly Ser Asp Val Phe Trp Asp Glu Ile
        115                 120                 125

Ile Ser Ile Glu Tyr Ile Gly Lys Glu Glu Val Phe Asp Leu Thr Ile
    130                 135                 140

Pro Glu Thr His Asn Phe Ile Ala Asn
145                 150

<210> SEQ ID NO 36
<211> LENGTH: 12
<212> TYPE: PRT
<213> ORGANISM: Artificial sequence
<220> FEATURE:
<223> OTHER INFORMATION: pMTE2-S11 C-precursor

<400> SEQUENCE: 36

Met Asp Phe Ile Val His Asn Cys Met Gly Lys Lys
1               5                   10

<210> SEQ ID NO 37
<211> LENGTH: 16
<212> TYPE: PRT
<213> ORGANISM: Artificial sequence
<220> FEATURE:
<223> OTHER INFORMATION: pMTE2-S1 N-precursor

<400> SEQUENCE: 37

Asp Leu Leu Arg Arg Cys Leu Ser Gly Ser Thr Lys Val Ile Asp Ala
1               5                   10                  15

<210> SEQ ID NO 38
<211> LENGTH: 148
<212> TYPE: PRT
<213> ORGANISM: Artificial sequence
<220> FEATURE:
<223> OTHER INFORMATION: pMTE2-S1 C-precursor

<400> SEQUENCE: 38

Ala Thr Gly Asn Leu Phe Ser Leu Lys Glu Ile Ala Ala Gln Pro Glu
1               5                   10                  15

Tyr Trp Leu Ser Arg Lys Val Phe Ser Leu Asp Leu Lys Ser Gln Gln
            20                  25                  30

Val Val Gln Gln Pro Ile Thr Glu Ile His Pro Asn Gly Val Arg Asp
        35                  40                  45

Val Trp Gln Ile Thr Thr Arg Thr Asn Arg Lys Val Cys Ala Thr Asp
    50                  55                  60

Asp His Leu Phe Tyr Thr Val Leu Gly Trp Lys Pro Leu Lys Asp Phe
65                  70                  75                  80

Ser Val Gly Asp Arg Leu Gly Leu Pro Asn Lys Ala Ser Gly His His
            85                  90                  95

His His His His Gly Gly Ser Gly Ser Asp Val Phe Trp Asp Glu Ile
            100                 105                 110

Ile Ser Ile Glu Tyr Ile Gly Lys Glu Glu Val Phe Asp Leu Thr Ile
        115                 120                 125

Pro Glu Thr His Asn Phe Ile Ala Asn Asp Phe Ile Val His Asn Cys
    130                 135                 140

Met Gly Lys Lys
145
```

<210> SEQ ID NO 39
<211> LENGTH: 148
<212> TYPE: PRT
<213> ORGANISM: Artificial sequence
<220> FEATURE:
<223> OTHER INFORMATION: pMTR1-S11 N-precursor

<400> SEQUENCE: 39

```
Gly Asn Ile Arg Arg Cys Leu Pro Glu Gly Ala Leu Val His Thr Ala
1               5                   10                  15

Ser Gly Leu Val Ala Ile Glu Lys Ile Arg Ile Gly Asp Arg Val Leu
            20                  25                  30

Thr Ser Gln Gly Phe Tyr Pro Val Thr Asn Phe Phe Asp Gln Gly Ile
        35                  40                  45

Gln Ser Leu Cys Arg Ile Gln Thr Glu Asp Gly Tyr Phe Glu Cys Thr
    50                  55                  60

Pro Asp His Lys Val Ala Val Leu Gln Asp Leu Tyr Gly Asn Tyr Lys
65                  70                  75                  80

Met Ile Lys Ala Lys Asp Leu Gln Glu Gly Asp Arg Leu Ile Phe Val
                85                  90                  95

Pro Gln Ala Ser Gly His His His His His Gly Gly Ser Gly Ser
            100                 105                 110

Asp Ala Thr Asp Leu Ile Pro Val Lys Val Lys Val Glu Met Asp
        115                 120                 125

Val Arg Glu Ala Ser Thr Tyr Asp Ile Glu Val Ala Ser Ile His Glu
    130                 135                 140

Phe Val Cys Gln
145
```

<210> SEQ ID NO 40
<211> LENGTH: 12
<212> TYPE: PRT
<213> ORGANISM: Artificial sequence
<220> FEATURE:
<223> OTHER INFORMATION: pMTR1-S11 C-precursor

<400> SEQUENCE: 40

```
Met Gly Ile Leu Val Ser Asn Ser Ala Gly Ile Arg
1               5                   10
```

<210> SEQ ID NO 41
<211> LENGTH: 16
<212> TYPE: PRT
<213> ORGANISM: Artificial sequence
<220> FEATURE:
<223> OTHER INFORMATION: pMTR1-S1 N-precursor

<400> SEQUENCE: 41

```
Gly Asn Ile Arg Arg Cys Leu Pro Glu Gly Ala Leu Val His Thr Ala
1               5                   10                  15
```

<210> SEQ ID NO 42
<211> LENGTH: 144
<212> TYPE: PRT
<213> ORGANISM: Artificial sequence
<220> FEATURE:
<223> OTHER INFORMATION: pMTR1-S1 C-precursor

<400> SEQUENCE: 42

```
Met Ser Gly Leu Val Ala Ile Glu Lys Ile Arg Ile Gly Asp Arg Val
1               5                   10                  15
```

```
Leu Thr Ser Gln Gly Phe Tyr Pro Val Thr Asn Phe Asp Gln Gly
            20                  25                  30

Ile Gln Ser Leu Cys Arg Ile Gln Thr Glu Asp Gly Tyr Phe Glu Cys
        35                  40                  45

Thr Pro Asp His Lys Val Ala Val Leu Gln Asp Leu Tyr Gly Asn Tyr
    50                  55                  60

Lys Met Ile Lys Ala Lys Asp Leu Gln Glu Gly Asp Arg Leu Ile Phe
65                  70                  75                  80

Val Pro Gln Ala Ser Gly His His His His His Gly Gly Ser Gly
            85                  90                  95

Ser Asp Ala Thr Asp Leu Ile Pro Val Lys Val Lys Lys Val Glu Met
            100                 105                 110

Asp Val Arg Glu Ala Ser Thr Tyr Asp Ile Glu Val Ala Ser Ile His
            115                 120                 125

Glu Phe Val Cys Gln Gly Ile Leu Val Ser Asn Ser Ala Gly Ile Arg
            130                 135                 140
```

<210> SEQ ID NO 43
<211> LENGTH: 146
<212> TYPE: PRT
<213> ORGANISM: Artificial sequence
<220> FEATURE:
<223> OTHER INFORMATION: pMTR2-S11 N-precursor

<400> SEQUENCE: 43

```
Leu Gly Leu Asn Pro Cys His Ser Gly Asp Thr Leu Val Ser Thr Asp
1               5                   10                  15

Gln Gly Leu Ile Ala Ile Gln Asp Leu Val Gly Lys Gln Phe Gln Ala
            20                  25                  30

Leu Val Asp Leu Arg Ser Ile Gly Leu Ser Gly Val Arg Leu Thr Asp
        35                  40                  45

Ala Ile Ala Phe Ala Thr Gly Val Lys Thr Thr Tyr Gln Val Ile Leu
    50                  55                  60

Asn Asn Gly Met Gln Met Arg Cys Thr Gly Asp His Gln His Phe Thr
65                  70                  75                  80

Ser Arg Gly Trp Val Ser Thr Arg Asp Leu Thr Asp Asp Asn Ile
            85                  90                  95

Tyr Ile Gln Gly Gly Ala Ser Gly His His His His His Gly Gly
            100                 105                 110

Ser Gly Ser Lys Phe Ile Ser Lys Val Lys Lys Val Glu Glu Phe Gly
            115                 120                 125

Glu Glu Val Val Tyr Asp Leu His Val Pro Leu Thr Asn Ser Phe Ile
            130                 135                 140

Ala Asn
145
```

<210> SEQ ID NO 44
<211> LENGTH: 12
<212> TYPE: PRT
<213> ORGANISM: Artificial sequence
<220> FEATURE:
<223> OTHER INFORMATION: pMTR2-S11 C-precursor

<400> SEQUENCE: 44

```
Met Gly Cys Leu Thr His Asn Cys Gly Glu Ile Ile
1               5                   10
```

<210> SEQ ID NO 45
<211> LENGTH: 17

```
<212> TYPE: PRT
<213> ORGANISM: Artificial sequence
<220> FEATURE:
<223> OTHER INFORMATION: pMTR2-S1 N-precursor

<400> SEQUENCE: 45

Leu Gly Leu Asn Pro Cys His Ser Gly Asp Thr Leu Val Ser Thr Asp
1               5                   10                  15

Gln

<210> SEQ ID NO 46
<211> LENGTH: 141
<212> TYPE: PRT
<213> ORGANISM: Artificial sequence
<220> FEATURE:
<223> OTHER INFORMATION: pMTR2-S1 C-precursor

<400> SEQUENCE: 46

Met Gly Leu Ile Ala Ile Gln Asp Leu Val Gly Lys Gln Phe Gln Ala
1               5                   10                  15

Leu Val Asp Leu Arg Ser Ile Gly Leu Ser Gly Val Arg Leu Thr Asp
                20                  25                  30

Ala Ile Ala Phe Ala Thr Gly Val Lys Thr Thr Tyr Gln Val Ile Leu
            35                  40                  45

Asn Asn Gly Met Gln Met Arg Cys Thr Gly Asp His Gln His Phe Thr
50                  55                  60

Ser Arg Gly Trp Val Ser Thr Arg Asp Leu Thr Asp Asp Asn Ile
65                  70                  75                  80

Tyr Ile Gln Gly Gly Ala Ser Gly His His His His Gly Gly
                85                  90                  95

Ser Gly Ser Lys Phe Ile Ser Lys Val Lys Val Glu Glu Phe Gly
                100                 105                 110

Glu Glu Val Val Tyr Asp Leu His Val Pro Leu Thr Asn Ser Phe Ile
                115                 120                 125

Ala Asn Gly Cys Leu Thr His Asn Cys Gly Glu Ile Ile
            130                 135                 140

<210> SEQ ID NO 47
<211> LENGTH: 148
<212> TYPE: PRT
<213> ORGANISM: Artificial sequence
<220> FEATURE:
<223> OTHER INFORMATION: pMTR4-S11 N-precursor

<400> SEQUENCE: 47

Val Gln Pro Ser Gly Cys Leu Asp Lys Thr Ala Leu Arg Ile Phe Asn
1               5                   10                  15

Gln Gly Leu Leu Tyr Ala Asp Glu Val Val Thr Pro Gly Ser Gly Glu
                20                  25                  30

Thr Val Gly Leu Gly Leu Thr Val Arg Asn Gly Ile Gly Ala Ser Thr
            35                  40                  45

Ala Ile Ala Asn Gln Pro Met Glu Leu Val Gly Ile Lys Leu Ala Asn
50                  55                  60

Gly Arg Lys Leu Arg Met Thr Pro Asn His Arg Met Ser Val Lys Gly
65                  70                  75                  80

Lys Trp Ile His Ala Cys Asn Leu Lys Pro Gly Met Leu Leu Asp Tyr
                85                  90                  95

Ser Ile Gly Glu Ala Ser Gly His His His His Gly Gly Ser
                100                 105                 110
```

```
Gly Ser Pro Tyr Lys Ile Glu Ser Val Asn Ile Gly Ala Val Cys Asp
            115                 120                 125

Tyr Ser Tyr Asp Phe Ala Ile Glu Gly Ile Asn Asp Asn Asp Ser Trp
        130                 135                 140

Tyr Trp Gln Gly
145

<210> SEQ ID NO 48
<211> LENGTH: 17
<212> TYPE: PRT
<213> ORGANISM: Artificial sequence
<220> FEATURE:
<223> OTHER INFORMATION: pMTR4-S11 C-precursor

<400> SEQUENCE: 48

Met Ala Leu Lys Ser His Asn Thr Lys Ser Leu Leu Thr Asn Ala Ser
1               5                   10                  15

Pro

<210> SEQ ID NO 49
<211> LENGTH: 17
<212> TYPE: PRT
<213> ORGANISM: Artificial sequence
<220> FEATURE:
<223> OTHER INFORMATION: pMTR4-S1 N-precursor

<400> SEQUENCE: 49

Val Gln Pro Ser Gly Cys Leu Asp Lys Thr Ala Leu Arg Ile Phe Asn
1               5                   10                  15

Gln

<210> SEQ ID NO 50
<211> LENGTH: 148
<212> TYPE: PRT
<213> ORGANISM: Artificial sequence
<220> FEATURE:
<223> OTHER INFORMATION: pMTR4-S1 C-precursor

<400> SEQUENCE: 50

Met Gly Leu Leu Tyr Ala Asp Glu Val Val Thr Pro Gly Ser Gly Glu
1               5                   10                  15

Thr Val Gly Leu Gly Leu Thr Val Arg Asn Gly Ile Gly Ala Ser Thr
            20                  25                  30

Ala Ile Ala Asn Gln Pro Met Glu Leu Val Glu Ile Lys Leu Ala Asn
        35                  40                  45

Gly Arg Lys Leu Arg Met Thr Pro Asn His Arg Met Ser Val Lys Gly
    50                  55                  60

Lys Trp Ile His Ala Cys Asn Leu Lys Pro Gly Met Leu Leu Asp Tyr
65                  70                  75                  80

Ser Ile Gly Glu Ala Ser Gly His His His His His Gly Gly Ser
                85                  90                  95

Gly Ser Pro Tyr Lys Ile Glu Ser Val Asn Ile Gly Ala Val Cys Asp
            100                 105                 110

Tyr Ser Tyr Asp Phe Ala Ile Glu Gly Ile Asn Asp Asn Asp Ser Trp
        115                 120                 125

Tyr Trp Gln Gly Ala Leu Lys Ser His Asn Thr Lys Ser Leu Leu Thr
    130                 135                 140

Asn Ala Ser Pro
145
```

```
<210> SEQ ID NO 51
<211> LENGTH: 147
<212> TYPE: PRT
<213> ORGANISM: Artificial sequence
<220> FEATURE:
<223> OTHER INFORMATION: pMTHE1-S11 N-precursor

<400> SEQUENCE: 51

Gly Gly Cys Leu Ala Glu Gly Ser Leu Val Leu Asp Ala Ala Thr Gly
1               5                   10                  15

Gln Arg Val Pro Ile Glu Lys Val Arg Pro Gly Met Glu Val Phe Ser
            20                  25                  30

Leu Gly Pro Asp Tyr Arg Leu Tyr Arg Val Pro Val Leu Glu Val Leu
        35                  40                  45

Glu Ser Gly Val Arg Glu Val Val Arg Leu Arg Thr Arg Ser Gly Arg
    50                  55                  60

Thr Leu Val Leu Thr Pro Asp His Pro Leu Leu Thr Pro Glu Gly Trp
65                  70                  75                  80

Lys Pro Leu Cys Asp Leu Pro Leu Gly Thr Pro Ile Ala Val Pro Ala
                85                  90                  95

Glu Leu Pro Val Ala Gly His Leu Ala Pro Pro Glu Asp Arg His Met
            100                 105                 110

Ala Glu Gly Gln Val Leu Trp Asp Pro Ile Val Ala Val Glu Pro Ala
        115                 120                 125

Gly Lys Ala Arg Thr Phe Asp Leu Arg Val Pro Pro Phe Ala Asn Phe
    130                 135                 140

Val Ser Glu
145

<210> SEQ ID NO 52
<211> LENGTH: 11
<212> TYPE: PRT
<213> ORGANISM: Artificial sequence
<220> FEATURE:
<223> OTHER INFORMATION: pMTHE1-S11 C-precursor

<400> SEQUENCE: 52

Met Asp Leu Val Val His Asn Ser Ala Gly Glu
1               5                   10

<210> SEQ ID NO 53
<211> LENGTH: 13
<212> TYPE: PRT
<213> ORGANISM: Artificial sequence
<220> FEATURE:
<223> OTHER INFORMATION: pMTHE1-S1 N-precursor

<400> SEQUENCE: 53

Gly Gly Cys Leu Ala Glu Gly Ser Leu Val Leu Asp Ala
1               5                   10

<210> SEQ ID NO 54
<211> LENGTH: 145
<212> TYPE: PRT
<213> ORGANISM: Artificial sequence
<220> FEATURE:
<223> OTHER INFORMATION: pMTHE1-S1 C-precursor

<400> SEQUENCE: 54

Met Ala Thr Gly Gln Arg Val Pro Ile Glu Lys Val Arg Pro Gly Met
1               5                   10                  15

Glu Val Phe Ser Leu Gly Pro Asp Tyr Arg Leu Tyr Arg Val Pro Val
            20                  25                  30
```

```
Leu Glu Val Leu Glu Ser Gly Val Arg Glu Val Arg Leu Arg Thr
            35                  40                  45

Arg Ser Gly Arg Thr Leu Val Leu Thr Pro Asp His Pro Leu Leu Thr
 50                  55                  60

Pro Glu Gly Trp Lys Pro Leu Cys Asp Leu Pro Leu Gly Thr Pro Ile
 65                  70                  75                  80

Ala Val Pro Ala Glu Leu Pro Val Ala Gly His Leu Ala Pro Pro Glu
                 85                  90                  95

Asp Arg His Met Ala Glu Gly Gln Val Leu Trp Asp Pro Ile Val Ala
                100                 105                 110

Val Glu Pro Ala Gly Lys Ala Arg Thr Phe Asp Leu Arg Val Pro Pro
            115                 120                 125

Phe Ala Asn Phe Val Ser Glu Asp Leu Val Val His Asn Ser Ala Gly
        130                 135                 140

Glu
145

<210> SEQ ID NO 55
<211> LENGTH: 152
<212> TYPE: PRT
<213> ORGANISM: Artificial sequence
<220> FEATURE:
<223> OTHER INFORMATION: pMTHE2-S11 N-precursor

<400> SEQUENCE: 55

Gly Gly Cys Leu Pro Ala Arg Ala Arg Val Val Asp Trp Cys Thr Gly
 1               5                  10                  15

Arg Val Val Arg Val Gly Glu Ile Val Arg Gly Glu Ala Lys Gly Val
                20                  25                  30

Trp Val Val Ser Leu Asp Glu Ala Arg Leu Arg Leu Val Pro Arg Pro
            35                  40                  45

Val Val Ala Ala Phe Pro Ser Gly Lys Ala Gln Val Tyr Ala Leu Arg
 50                  55                  60

Thr Ala Thr Gly Arg Val Leu Glu Ala Thr Ala Asn His Pro Val Tyr
 65                  70                  75                  80

Thr Pro Glu Gly Trp Arg Pro Leu Gly Thr Leu Ala Pro Gly Asp Tyr
                 85                  90                  95

Val Ala Leu Pro Arg His Leu Ser Tyr Arg Pro Ser Leu His Leu Glu
                100                 105                 110

Gly His Glu His Met Ala Glu Ala Glu Val Tyr Trp Asp Arg Val Glu
            115                 120                 125

Ala Val Glu Pro Leu Gly Glu Glu Val Phe Asp Leu Thr Val Glu
        130                 135                 140

Gly Thr His Thr Phe Val Ala Glu
145                 150

<210> SEQ ID NO 56
<211> LENGTH: 11
<212> TYPE: PRT
<213> ORGANISM: Artificial sequence
<220> FEATURE:
<223> OTHER INFORMATION: pMTHE2-S11 C-precursor

<400> SEQUENCE: 56

Met Asp Val Ile Val His Asn Ser Ala Gly Glu
 1               5                  10

<210> SEQ ID NO 57
```

```
<211> LENGTH: 12
<212> TYPE: PRT
<213> ORGANISM: Artificial sequence
<220> FEATURE:
<223> OTHER INFORMATION: pMTHE2-S1 N-precursor

<400> SEQUENCE: 57

Gly Gly Cys Leu Pro Ala Arg Ala Arg Val Val Asp
1               5                   10

<210> SEQ ID NO 58
<211> LENGTH: 151
<212> TYPE: PRT
<213> ORGANISM: Artificial sequence
<220> FEATURE:
<223> OTHER INFORMATION: pMTHE2-S1 C-precursor

<400> SEQUENCE: 58

Met Trp Cys Thr Gly Arg Val Val Arg Val Gly Glu Ile Val Arg Gly
1               5                   10                  15

Glu Ala Lys Gly Val Trp Val Val Ser Leu Asp Glu Ala Arg Leu Arg
                20                  25                  30

Leu Val Pro Arg Pro Val Val Ala Ala Phe Pro Ser Gly Lys Ala Gln
            35                  40                  45

Val Tyr Ala Leu Arg Thr Ala Thr Gly Arg Val Leu Glu Ala Thr Ala
    50                  55                  60

Asn His Pro Val Tyr Thr Pro Glu Gly Trp Arg Pro Leu Gly Thr Leu
65                  70                  75                  80

Ala Pro Gly Asp Tyr Val Ala Leu Pro Arg His Leu Ser Tyr Arg Pro
                85                  90                  95

Ser Leu His Leu Glu Gly His Glu His Met Ala Glu Ala Glu Val Tyr
            100                 105                 110

Trp Asp Arg Val Glu Ala Val Glu Pro Leu Gly Glu Glu Val Phe
            115                 120                 125

Asp Leu Thr Val Glu Gly Thr His Thr Phe Val Ala Glu Asp Val Ile
            130                 135                 140

Val His Asn Ser Ala Gly Glu
145                 150

<210> SEQ ID NO 59
<211> LENGTH: 158
<212> TYPE: PRT
<213> ORGANISM: Artificial sequence
<220> FEATURE:
<223> OTHER INFORMATION: pMTHR-S11 N-precursor

<400> SEQUENCE: 59

Gly Gly Cys Leu His Pro Asp Thr Leu Val His Thr Asp Arg Gly Thr
1               5                   10                  15

Leu Arg Leu Arg Glu Leu Val Asp Pro Phe Arg Arg Gly Trp Gln Pro
                20                  25                  30

His Thr Leu Ser Val Ala Thr Asp Glu Gly Trp Arg Pro Ser Pro Glu
            35                  40                  45

Gly Tyr Asn Asn Gly Val Ala Pro Thr Leu Arg Val Val Leu Glu Asn
    50                  55                  60

Gly Leu Glu Val Gln Gly Thr Leu Asn His Lys Leu Lys Val Leu Arg
65                  70                  75                  80

Glu Asp Gly Thr Arg Glu Trp Val Glu Leu Gln Asp Leu Arg Pro Gly
                85                  90                  95

Asp Trp Val Ile Trp Val Leu Asp Glu His Thr Gly Thr Pro Val Gln
```

```
Leu Ala Pro Leu Asp Glu His Met Ala Glu Pro Phe Pro Phe Asn Glu
            115                 120                 125

Tyr Tyr Val Arg Val Ala Ser Val Glu Pro Gly Gly Glu Ile Leu Thr
        130                 135                 140

Leu Asp Leu Ser Val Glu Gly Asn His Thr Tyr Leu Ala Asn
145                 150                 155

<210> SEQ ID NO 60
<211> LENGTH: 11
<212> TYPE: PRT
<213> ORGANISM: Artificial sequence
<220> FEATURE:
<223> OTHER INFORMATION: pMTHR-S11 C-precursor

<400> SEQUENCE: 60

Met Gly Leu Val Ser His Asn Ser Ala Gly Glu
1               5                   10

<210> SEQ ID NO 61
<211> LENGTH: 14
<212> TYPE: PRT
<213> ORGANISM: Artificial sequence
<220> FEATURE:
<223> OTHER INFORMATION: pMTHR-S1 N-precursor

<400> SEQUENCE: 61

Gly Gly Cys Leu His Pro Asp Thr Leu Val His Thr Asp Arg
1               5                   10

<210> SEQ ID NO 62
<211> LENGTH: 155
<212> TYPE: PRT
<213> ORGANISM: Artificial sequence
<220> FEATURE:
<223> OTHER INFORMATION: pMTHR-S1 C-precursor

<400> SEQUENCE: 62

Met Gly Thr Leu Arg Leu Arg Glu Leu Val Asp Pro Phe Arg Arg Gly
1               5                   10                  15

Trp Gln Pro His Thr Leu Ser Val Ala Thr Asp Glu Gly Trp Arg Pro
            20                  25                  30

Ser Pro Glu Gly Tyr Asn Asn Gly Val Ala Pro Thr Leu Arg Val Val
        35                  40                  45

Leu Glu Asn Gly Leu Glu Val Gln Gly Thr Leu Asn His Lys Leu Lys
    50                  55                  60

Val Leu Arg Glu Asp Gly Thr Arg Glu Trp Val Glu Leu Gln Asp Leu
65                  70                  75                  80

Arg Pro Gly Asp Trp Val Ile Trp Val Leu Asp Glu His Thr Gly Thr
                85                  90                  95

Pro Val Gln Leu Ala Pro Leu Asp Glu His Met Ala Glu Pro Phe Pro
            100                 105                 110

Phe Asn Glu Tyr Tyr Val Arg Val Ala Ser Val Glu Pro Gly Gly Glu
        115                 120                 125

Ile Leu Thr Leu Asp Leu Ser Val Glu Gly Asn His Thr Tyr Leu Ala
    130                 135                 140

Asn Gly Leu Val Ser His Asn Ser Ala Gly Glu
145                 150                 155

<210> SEQ ID NO 63
<211> LENGTH: 6
```

```
<212> TYPE: PRT
<213> ORGANISM: Artificial sequence
<220> FEATURE:
<223> OTHER INFORMATION: SCI from Ssp GyrB

<400> SEQUENCE: 63

Gly Val Phe Val His Asn
1               5

<210> SEQ ID NO 64
<211> LENGTH: 6
<212> TYPE: PRT
<213> ORGANISM: Artificial sequence
<220> FEATURE:
<223> OTHER INFORMATION: SCI from Ssp DnaX

<400> SEQUENCE: 64

Gly Leu Leu Val His Asn
1               5

<210> SEQ ID NO 65
<211> LENGTH: 6
<212> TYPE: PRT
<213> ORGANISM: Artificial sequence
<220> FEATURE:
<223> OTHER INFORMATION: SCI from Ter DnaE3

<400> SEQUENCE: 65

Gly Leu Ile Ala Ser Asn
1               5

<210> SEQ ID NO 66
<211> LENGTH: 6
<212> TYPE: PRT
<213> ORGANISM: Artificial sequence
<220> FEATURE:
<223> OTHER INFORMATION: SCI from Ter ThyX

<400> SEQUENCE: 66

Gly Leu Val Val His Asn
1               5

<210> SEQ ID NO 67
<211> LENGTH: 12
<212> TYPE: PRT
<213> ORGANISM: Artificial sequence
<220> FEATURE:
<223> OTHER INFORMATION: SNI from Ssp GyrB

<400> SEQUENCE: 67

Cys Phe Ser Gly Asp Thr Leu Val Ala Leu Thr Asp
1               5                   10

<210> SEQ ID NO 68
<211> LENGTH: 11
<212> TYPE: PRT
<213> ORGANISM: Artificial sequence
<220> FEATURE:
<223> OTHER INFORMATION: SNI from Rma DnaB

<400> SEQUENCE: 68

Cys Leu Ala Gly Asp Thr Leu Ile Thr Leu Ala
1               5                   10

<210> SEQ ID NO 69
<211> LENGTH: 10
<212> TYPE: PRT
<213> ORGANISM: Artificial sequence
```

```
<220> FEATURE:
<223> OTHER INFORMATION: SNI from Cne Prp8

<400> SEQUENCE: 69

Cys Leu Gln Asn Gly Thr Arg Leu Leu Arg
1               5                   10

<210> SEQ ID NO 70
<211> LENGTH: 11
<212> TYPE: PRT
<213> ORGANISM: Artificial sequence
<220> FEATURE:
<223> OTHER INFORMATION: SNI from Ssp DnaX

<400> SEQUENCE: 70

Cys Leu Thr Gly Asp Ser Gln Val Leu Thr Arg
1               5                   10

<210> SEQ ID NO 71
<211> LENGTH: 11
<212> TYPE: PRT
<213> ORGANISM: Artificial sequence
<220> FEATURE:
<223> OTHER INFORMATION: SNI from Ter DnaE3

<400> SEQUENCE: 71

Cys Leu Thr Tyr Glu Thr Glu Ile Met Thr Val
1               5                   10

<210> SEQ ID NO 72
<211> LENGTH: 12
<212> TYPE: PRT
<213> ORGANISM: Artificial sequence
<220> FEATURE:
<223> OTHER INFORMATION: SNI from Ter ThyX

<400> SEQUENCE: 72

Cys Leu Ser Gly Asn Thr Lys Val Arg Phe Arg Tyr
1               5                   10

<210> SEQ ID NO 73
<211> LENGTH: 30
<212> TYPE: PRT
<213> ORGANISM: Artificial sequence
<220> FEATURE:
<223> OTHER INFORMATION: Synthetic peptide IcF

<400> SEQUENCE: 73

Gly Val Phe Val His Asn Ser Ala Asp Tyr Lys Asp Asp Asp Lys
1               5                   10                  15

Ser Gly Cys Leu Ala Gly Asp Thr Leu Ile Thr Leu Ala Ser
            20                  25                  30

<210> SEQ ID NO 74
<211> LENGTH: 8
<212> TYPE: PRT
<213> ORGANISM: Artificial sequence
<220> FEATURE:
<223> OTHER INFORMATION: FLAG epitope

<400> SEQUENCE: 74

Asp Tyr Lys Asp Asp Asp Asp Lys
1               5

<210> SEQ ID NO 75
<211> LENGTH: 38
<212> TYPE: DNA
```

-continued

<213> ORGANISM: Artificial sequence
<220> FEATURE:
<223> OTHER INFORMATION: Primer

<400> SEQUENCE: 75
ctcgagggcg gttgtttttc tggagataca ttagtcgc                38

<210> SEQ ID NO 76
<211> LENGTH: 30
<212> TYPE: DNA
<213> ORGANISM: Artificial sequence
<220> FEATURE:
<223> OTHER INFORMATION: Primer

<400> SEQUENCE: 76
catatgacca gaatcttccg tagtcgaaat                          30

<210> SEQ ID NO 77
<211> LENGTH: 32
<212> TYPE: DNA
<213> ORGANISM: Artificial sequence
<220> FEATURE:
<223> OTHER INFORMATION: Primer

<400> SEQUENCE: 77
catatggaag cagtattaaa ttacaatcac ag                       32

<210> SEQ ID NO 78
<211> LENGTH: 36
<212> TYPE: DNA
<213> ORGANISM: Artificial sequence
<220> FEATURE:
<223> OTHER INFORMATION: Primer

<400> SEQUENCE: 78
gaccggtctc gccagcgctg ttatggacaa acactc                   36

<210> SEQ ID NO 79
<211> LENGTH: 30
<212> TYPE: DNA
<213> ORGANISM: Artificial sequence
<220> FEATURE:
<223> OTHER INFORMATION: Spacer

<400> SEQUENCE: 79
taattaactt ataaggagga aaaacatatg                          30

<210> SEQ ID NO 80
<211> LENGTH: 48
<212> TYPE: DNA
<213> ORGANISM: Artificial sequence
<220> FEATURE:
<223> OTHER INFORMATION: Primer

<400> SEQUENCE: 80
catcaccacc atcaccatta attaacttat aaggaggaaa aacatatg      48

<210> SEQ ID NO 81
<211> LENGTH: 21
<212> TYPE: DNA
<213> ORGANISM: Artificial sequence
<220> FEATURE:
<223> OTHER INFORMATION: Primer

<400> SEQUENCE: 81
cgttgccaaa gcaaaattgt g                                   21

```
<210> SEQ ID NO 82
<211> LENGTH: 12
<212> TYPE: PRT
<213> ORGANISM: Artificial sequence
<220> FEATURE:
<223> OTHER INFORMATION: Synthetic peptide

<400> SEQUENCE: 82

Gly Val Phe Val His Asn Ser Ala Gly Ser Gly Lys
1               5                   10

<210> SEQ ID NO 83
<211> LENGTH: 6
<212> TYPE: PRT
<213> ORGANISM: Artificial sequence
<220> FEATURE:
<223> OTHER INFORMATION: Linker

<400> SEQUENCE: 83

Ser Ala Gly Ser Gly Lys
1               5

<210> SEQ ID NO 84
<211> LENGTH: 12
<212> TYPE: PRT
<213> ORGANISM: Artificial sequence
<220> FEATURE:
<223> OTHER INFORMATION: Peptide

<400> SEQUENCE: 84

Gly Thr Leu Glu Gly Gly Ser Ala Gly Ser Gly Lys
1               5                   10

<210> SEQ ID NO 85
<211> LENGTH: 11
<212> TYPE: PRT
<213> ORGANISM: Artificial sequence
<220> FEATURE:
<223> OTHER INFORMATION: Synthetic peptide

<400> SEQUENCE: 85

Gly Val Phe Val His Asn Ser Ala Gly Ser Lys
1               5                   10

<210> SEQ ID NO 86
<211> LENGTH: 8
<212> TYPE: PRT
<213> ORGANISM: Artificial sequence
<220> FEATURE:
<223> OTHER INFORMATION: Synthetic peptide

<400> SEQUENCE: 86

Gly Val Phe Val His Ala Ser Gly
1               5

<210> SEQ ID NO 87
<211> LENGTH: 32
<212> TYPE: DNA
<213> ORGANISM: Artificial sequence
<220> FEATURE:
<223> OTHER INFORMATION: Primer

<400> SEQUENCE: 87
gggctcgagg gcggttgttt ttctggagat ac                                    32

<210> SEQ ID NO 88
<211> LENGTH: 35
```

```
-continued
<212> TYPE: DNA
<213> ORGANISM: Artificial sequence
<220> FEATURE:
<223> OTHER INFORMATION: Primer

<400> SEQUENCE: 88
gggaagcttc aatggtggtg atggtgatgg cttgc                              35

<210> SEQ ID NO 89
<211> LENGTH: 32
<212> TYPE: DNA
<213> ORGANISM: Artificial sequence
<220> FEATURE:
<223> OTHER INFORMATION: Primer

<400> SEQUENCE: 89
gggctcgagg gcggttgttt ttctggagat ac                                 32

<210> SEQ ID NO 90
<211> LENGTH: 34
<212> TYPE: DNA
<213> ORGANISM: Artificial sequence
<220> FEATURE:
<223> OTHER INFORMATION: Primer

<400> SEQUENCE: 90
gggaagcttt catgatgcca aagcaaaatt gtgg                               34

<210> SEQ ID NO 91
<211> LENGTH: 32
<212> TYPE: DNA
<213> ORGANISM: Artificial sequence
<220> FEATURE:
<223> OTHER INFORMATION: Primer

<400> SEQUENCE: 91
gggaccggta tgaccagaat cttccgtagt cg                                 32

<210> SEQ ID NO 92
<211> LENGTH: 33
<212> TYPE: DNA
<213> ORGANISM: Artificial sequence
<220> FEATURE:
<223> OTHER INFORMATION: Primer

<400> SEQUENCE: 92
gggaccggtg tggggaacct caatatcata aac                                33

<210> SEQ ID NO 93
<211> LENGTH: 11
<212> TYPE: PRT
<213> ORGANISM: Artificial sequence
<220> FEATURE:
<223> OTHER INFORMATION: synthetic peptide

<400> SEQUENCE: 93

Cys Ile Ser Gly Asp Ser Leu Ile Ser Leu Ala
1               5                   10
```